United States Patent
Meyer-Kobbe et al.

(10) Patent No.: US 11,793,911 B2
(45) Date of Patent: Oct. 24, 2023

(54) STENT MADE OF A BIO-DEGRADABLE MAGNESIUM ALLOY WITH A MAGNESIUM FLUORIDE COATING AND AN ORGANIC COATING

(71) Applicant: MeKo Laserstrahl-Materialbearbeitungen e.K., Sarstedt (DE)

(72) Inventors: Clemens Meyer-Kobbe, Sarstedt (DE); Michael Stekker, Aurich (DE); Roman Menze, Hannover (DE)

(73) Assignee: MeKo Laserstrahl-Materialbearbeitungen e.K., Sarstedt (DE)

( * ) Notice: Subject to any disclaimer, the term of this patent is extended or adjusted under 35 U.S.C. 154(b) by 0 days.

(21) Appl. No.: 16/473,267

(22) PCT Filed: Jan. 2, 2018

(86) PCT No.: PCT/EP2018/050084
§ 371 (c)(1),
(2) Date: Jun. 25, 2019

(87) PCT Pub. No.: WO2018/122418
PCT Pub. Date: Jul. 5, 2018

(65) Prior Publication Data
US 2020/0139017 A1    May 7, 2020

(30) Foreign Application Priority Data

Dec. 27, 2016 (EP) .................... 16207023

(51) Int. Cl.
| | |
|---|---|
| A61L 31/02 | (2006.01) |
| A61L 31/14 | (2006.01) |
| A61L 31/08 | (2006.01) |
| A61L 31/10 | (2006.01) |
| A61L 31/16 | (2006.01) |
| A61L 33/00 | (2006.01) |

(52) U.S. Cl.
CPC ........... *A61L 31/022* (2013.01); *A61L 31/088* (2013.01); *A61L 31/10* (2013.01); *A61L 31/148* (2013.01); *A61L 31/16* (2013.01); *A61L 33/0005* (2013.01); *A61L 2300/216* (2013.01); *A61L 2300/416* (2013.01); *A61L 2420/08* (2013.01)

(58) Field of Classification Search
CPC ........... A61L 2300/416; A61L 2420/08; A61L 31/022; A61L 31/028; A61L 31/16; A61L 33/0005; A61L 31/088; A61L 31/148; A61L 2300/216
See application file for complete search history.

(56) References Cited

U.S. PATENT DOCUMENTS

| | | | |
|---|---|---|---|
| 2010/0057188 A1 | 3/2010 | Weber | |
| 2010/0145436 A1* | 6/2010 | Weber | A61F 2/82 623/1.38 |
| 2010/0161053 A1* | 6/2010 | Bayer | A61F 2/02 623/11.11 |
| 2014/0199365 A1* | 7/2014 | Stekker | C22C 1/02 424/426 |
| 2016/0129162 A1 | 5/2016 | Pulugurtha et al. | |

FOREIGN PATENT DOCUMENTS

| | | |
|---|---|---|
| CN | 101468216 | 7/2009 |
| WO | 2010025078 | 3/2010 |
| WO | 2016073851 | 5/2016 |

OTHER PUBLICATIONS

Liu et al. (Journal of Materials Science & Technology 31, 2015, 733-243) (Year: 2015).*
Wang et al. (Russian Journal of Non-Ferrous Metals vol. 57, No. 4 381-388 2016) (Year: 2016).*
International Search Report for International Patent Application No. PCT/EP2018/050084 dated Mar. 20, 2018, 6 pages.
Conceicao, et al. "Corrosion protection of magnesium AZ31 alloy sheets by polymer coatings", PhD Thesis, Berlin 2011.

* cited by examiner

*Primary Examiner* — Anna R Falkowitz
(74) *Attorney, Agent, or Firm* — AMIN, TUROCY & WATSON, LLP

(57) ABSTRACT

The present invention relates to stents made of a magnesium alloy degradable under physiological conditions having an inorganic coating comprising magnesium fluoride and having an organic coating. The stents according the invention can additionally be coated with at least one antiinflammatory, antiproliferative, antiangiogenic, antirestenotic, and/or antithrombogenic active agent.

11 Claims, 16 Drawing Sheets

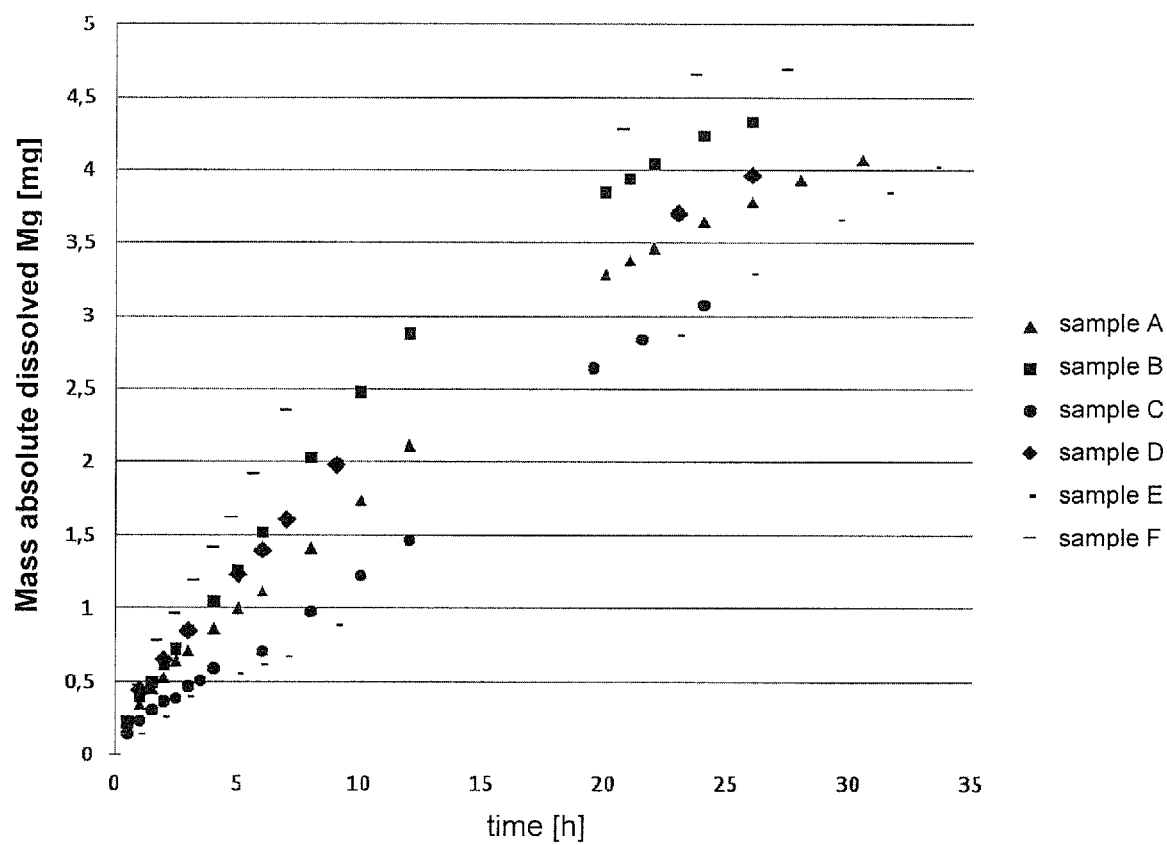
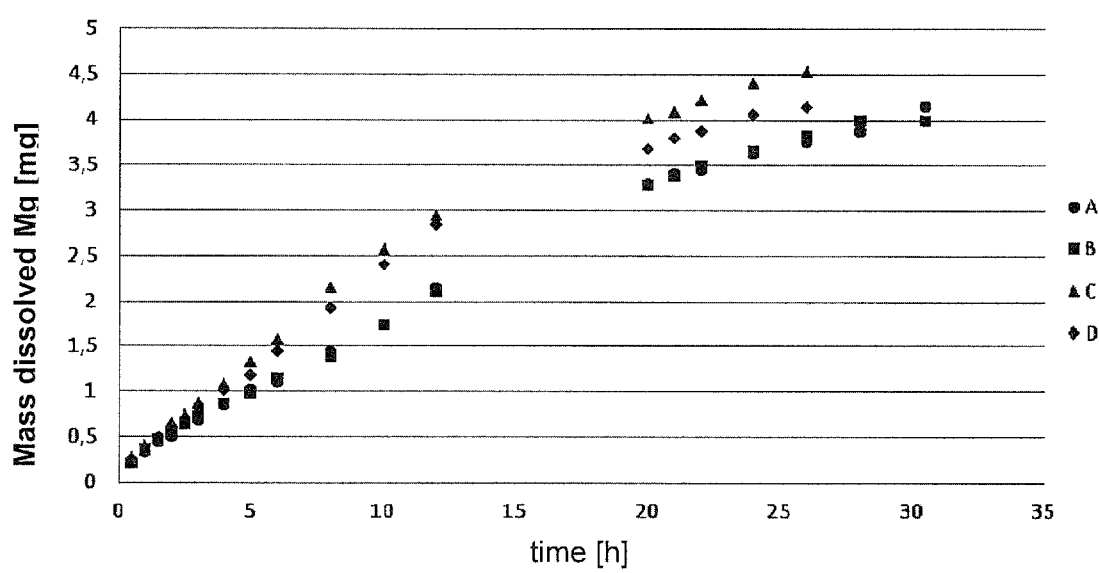

STENT MADE OF A BIO-DEGRADABLE MAGNESIUM ALLOY WITH A MAGNESIUM FLUORIDE COATING AND AN ORGANIC COATING

The present invention relates to stents made of a magnesium alloy degradable under physiological conditions having an inorganic coating comprising magnesium fluoride and having an organic coating. The stents according the invention can additionally be coated with at least one antiinflammatory, antiproliferative, antiangiogenic, antirestenotic, and/or antithrombogenic active agent.

Nowadays, the implantation of vessel grafts such as stents is a common surgical intervention for the treatment of stenoses. They are usually made of metal alloys such as stainless steel or nitinol. Such metal stents are known in large numbers and have proven to work in practice. Due to their metallic structure and load capacity such metal stents should ensure that the vessels remain open after implantation and that the blood flow through the vessels will be ensured permanently.

However, recent investigations have shown that vascular stenoses do not have to be dilated permanently by means of an endoprosthesis, particularly in form of a stent. It is absolutely sufficient to support the blood vessel temporarily as the traumatized tissue of the vessel heals and the smooth muscle cells of the vessel regenerate and resume the task of keeping the blood vessel open, and thus the stent does not need to remain longer than is necessary in the vessel lumen.

Stents are currently divided into two basic types, permanent as well as degradable or resorbable stents. Permanent stents are designed such that they can remain in the vessel for an indefinite period of time. Resorbable stents, however, are degraded in the vessel over a predetermined period of time.

Currently, one tries to solve the problem of restenosis after stent implantation by attempting to locally inhibit the growth of the smooth muscle cells. This is for example attempted with stents, which release pharmaceutically active agents, preferably having an antiproliferative effect. These active agents are mostly released from an active agent-containing coating, which may be applied both to permanent and to resorbable stents.

The supporting effect by the metal structure is often only required for short periods of time as the body tissue can recover after the implantation of the stent and the supporting function is no longer necessary. Preferably, degradable and resorbable stents are only degraded when the traumatized tissue of the vessel has healed and the vessel re-stabilized, so that the stent does no longer have to remain in the vessel lumen. Especially in the case of stents coming in contact with blood, these cause as being a material foreign to the body a reaction of the surrounding tissue which can result in the formation of restenosis through proliferation. Efforts in the development of stents to an improved biocompatibility of the stent material, greater flexibility with decreasing material fatigue and reduction of the foreign surface should minimize the risk of stent-induced restenosis rate further and further. Here, resorbable stents have the advantage that the material foreign to the body does not permanently remain in the vessel and the risk of restenosis is therefore temporally limited. A use of resorbable stents is advantageous for children too, since vascular growth is not adversely affected, or the stent does not need to be removed again after a while during which the child has grown.

For said reason, stents consisting of bioresorbable materials, such as for example of polymers such as polyhydroxybutyrate or of metals such as magnesium or iron are increasingly developed in recent times and used in clinical trials.

The large restoring forces of vessels in the first days after dilation are a major cause of restenoses. Therefore, resorbable vessel grafts must consist of a material which can be degraded well by the body, but also has a sufficiently high retention force to prevent re-stenosis of the vessel.

Once inserted, a stent must maintain its size and shape despite the different forces acting on it such as the pulsating load by the beating heart. In addition, the stent must have sufficient flexibility to be crimped onto a balloon, and later to be expanded in the vessel.

Resorbable polymers which are used for the production of stents have lower mechanical strength than those non-resorbable metal alloys used hitherto. A compensation of this disadvantage can be achieved by greater strut widths of the stent. However, this increases the mechanical irritation of the vessel wall during stent implantation, and thus also the risk of restenosis. Resorbable stents from iron or an iron-based alloy have the disadvantage that the residence time in the vessel up to the full degradation is longer than necessary and desired. For resorbable stents the desired period of resorption is between 3 and 12 months, wherein the mechanical load capacity needs to be ensured before. Magnesium is a trace element present in the body and therefore suitable as a basis for a resorbable stent. Further, alloying elements were selected from the group of the rare earths, as these do not naturally occur in the body. This allows a detection of the degradation products in the tissue and in the organs.

Magnesium and magnesium alloys have excellent mechanical and physical properties for a wide range of applications. Their low weight along with high strength qualifies magnesium and magnesium alloys as appropriate materials also for endoprostheses. Magnesium and magnesium alloys are very reactive and therefore susceptible to corrosion. Nevertheless these properties are desirable for absorbable implants. However, the following problems exist in the prior art: Although in principle the objective of resorption of the implanted stent is achieved, the problem of a temporally non-defined degradation of the stent exists. Depending on the choice of material, the degradation of the material is subjected to strong fluctuations, cannot be controlled, and is generally too fast to ensure a safe ingrowth of the stent into the vessel walls. When resorption occurs too fast the resorbable stent cannot grow into the vessel wall and take over the supporting function until the regeneration of the vessel segment. It can rather detach or fragments of the stent may be detached and be swept away in the blood flow and cause life-threatening problems for the patient.

A bioresorbable metal stent of magnesium and yttrium is disclosed in the European patent EP 1 419 793 B1. A magnesium alloy with yttrium, neodymium and further optional components suitable for the production of stents is described in the European patent EP 2 169 090. These stents have the disadvantage that they dissolve too fast and also uncontrolled. Since the dissolution process usually starts before the stent is grown into the vessel wall, fragments may be detached, transported through the bloodstream and cause a heart attack. Further, it has been found that these stents of a magnesium-yttrium alloy promote the deposition of calcium phosphate on the luminal surface of the stents and thereby leading to a re-occlusion of the stent (in-stent restenosis) and thus also of the vessel, which is precisely what should be prevented.

The European patent applications EP 2 213 314 A1 and EP 1 842 507 A1 also disclose stents of a magnesium alloy containing gadolinium. To obtain the desired mechanical properties such as strength, tension force and ductility, gadolinium is required in quantities greater than 5% by weight. At quantities greater than 5% by weight gadolinium, however, the problem arises that the processability of the alloy into a tube suitable for laser processing, and the homogeneity of the alloy is no longer guaranteed. The poorer processability leads to thicker stent struts which are a problem since the bloodstream was obstructed, which has led to thrombi.

An influence on the kinetics of resorption as well as degradation can also be achieved by matching of an optimized material for the basic scaffold and a coating, which positively affects the dissolution kinetics, i.e. slowing down. Such a coating has also to be sufficiently resistant for example to withstand the stresses that a stent is exposed to during implantation without damage.

Magnesium fluoride coatings for stents made of bioresorbable magnesium alloys are well known in the art. Lin et al. describe a protective effect of the magnesium fluoride film on the JBDM alloy Mg2.5Nd0.2Zn0.4Zr (ACS Applied Materials & Interfaces 2015, 7, p. 5320-5330). The magnesium fluoride film was produced by treating the alloy with a potassium fluoride solution. In vitro studies showed that the degradation rate could be reduced by 20% compared to the uncoated alloy.

Nan et al. investigated the influence of a magnesium fluoride and a collagen coating on the formation of endothelial cells on bioabsorbable magnesium struts (International Journal of Molecular Sciences 2014, 15, p. 5263-5276). The endothelial cell deposition and proliferation were significantly more pronounced on a magnesium fluoride coating than on a collagen coating.

The international patent application WO 2014/143521 A1 discloses stents of bioabsorbable magnesium alloys for which their corrosion was decelerated by passivation using hydrothermal treatment. The corrosion resistance increases with increasing layer thickness. However, layer thicknesses of over 150 μm are necessary for sufficiently long resistance, which can lead to increased crack appearance in the coating due to the dynamic load of the stent. The stents may also have a polymer coating to shield the stent body from the external environment and thus decelerate corrosion.

The international patent application WO 2016/073851 A2 also disclosed stents of a bioabsorbable magnesium alloy, the corrosion of which has been slowed down by passivation by hydrothermal treatment and which have a moisture barrier layer. This additional layer consists of a metal, an organometallic derivative or a polymeric alkoxide such as polyaluminium ethylene glycol (Alucon).

The publication of patent application US 2010/145436 A1 discloses biodegradable stent of metal or bioabsorbable or biostable polymer having a degradation retardant magnesium fluoride coating or polymer coating. The polymer coating detaches from the stent during expansion so that the stent comes into contact with the vessel wall.

Biostable metallic stents having a porous surface containing an active agent and a non-polymeric biodegradable coating are described in WO 2010/025078 A2. The biodegradable coating of magnesium fluoride, calcium phosphate, apatite, calcium carbonate or calcium fluoride serves for the delayed controlled release of the active agent.

For this reason, there is a need to develop a suitable material for resorbable stents and to combine it with a coating that allows to control the degradation of the stent. The object of the present invention is to provide a vessel graft only acting as a support until the regenerated tissue is able to take over this function again and to avoid the disadvantages of the state of the art.

More specific, the object of the present invention is to provide a stent of a magnesium alloy and a coating matched to it, the dissolution kinetics of which are delayed to significantly decelarated than those of the known stents.

Said objective is solved by the technical teaching of the independent claims of the present invention. Further advantageous embodiments of the invention result from the dependent claims, the description and the examples.

Surprisingly, it has been shown that stents of magnesium alloy are characterized by advantageous corrosion behaviour, desirable resorption kinetics and a high biocompatibility when provided with a magnesium fluoride coating and an organic coating as disclosed herein.

The use of a magnesium fluoride coating and a second organic coating allows to avoid crack formation at small layer thicknesses of few micrometers and therefore to avoid an early degradation of the stent.

Therefore, the present invention relates to stents consisting of a biologically degradable magnesium alloy having an inorganic coating comprising magnesium fluoride and an organic coating, wherein the magnesium alloy contains at least 80% by weight magnesium.

The inorganic magnesium fluoride coating of the stent can be produced by transformation of the base material on the surface area/edge zone area or as an applied substrate. Thereby, the magnesium fluoride coating of the stent by transformation of the base material on the surface area/edge zone area means the formation of an inorganic layer of the stent material itself. For transformation of the base material on the surface area/edge zone area, ion implantation or chemical transformation such as reaction with hydrofluoric acid, potassium fluoride, etc. can be used. For production of an inorganic coating of a stent as an applied substrate, the coating comprises magnesium fluoride, which can be applied by using the various chemical and physical methods as described herein.

The application of the inorganic coating is not limited to the surface of a stent, but can also be generated within the stent if required. Depending on the test parameters used, an ion-implanted edge zone can be created by using an ion implantation process. The layer thickness of the edge zone can be modified by the choice of the experimental parameters.

The inorganic coating or the surface modification by ion implantation of the stents according to the invention preferably affects the stent struts of the basic scaffold itself or the entire stent scaffold, i.e. the entire stent. The stent can be coated on both sides the abluminal as well as the luminal side of the stent body or only on one side. The coatings on the luminal or abluminal side of the stent may also be different, e.g. in the amount of active agent or in the composition of the organic compounds.

Surprisingly, it has been found that the inorganic coating comprising or consisting of magnesium alloy enhances the adhesion of an overlying organic coating in comparison to the stent surface and at the same time the organic coating increases the strength of the intermediate layer of magnesium fluoride. Thus, early detaching of the organic coating due to the adhesive intermediate layer of magnesium fluoride is prevented and a rupture and/or spalling of the intermediate layer of magnesium fluoride is prevented due to the overlying organic coating after crimping or during dilatation.

According to the invention, the organic coating prevents the early and inhomogeneous degradation of the stent consisting of a magnesium alloy having an inorganic coating by applying the organic layer to the inorganic coating. Thus, the present invention relates to stents of a basic scaffold of a biodegradable magnesium alloy having at least 80% by weight magnesium, as described herein, an inorganic coating comprising or consisting of magnesium fluoride and an organic coating, wherein the organic coating covers the inorganic coating. Thus, it is preferred that the inorganic coating of magnesium fluoride preferably fully covers the stent of magnesium alloy, i.e. without gaps on its luminal and abluminal surface and the organic coating, which preferably consists of organic polymers, in turn fully covers the inorganic coating of magnesium fluoride as a layer.

With other words, the stents according to the invention have two coatings, wherein the first coating is referred to as that one which is directly applied to the stent. The second coating is referred to as the coating that is applied to this first inorganic coating after it has already been applied to the stent. Thus, the first coating is also referred to as intermediate layer as it is located between the stent surface and the organic second coating.

This two-layer system of a layer of magnesium fluoride and an outer layer of an organic polymer or polymer mixture is essential with respect to the invention. The inventive effect of the degradation delay is not achieved if the layers are reversed, i.e. the lower layer is the organic polymer or polymer mixture and the outer layer consist of magnesium fluoride. Also, the inventive effect is not achieved if no two-layer system is formed, i.e. magnesium fluoride and organic polymer or polymer mixture are applied to the stent of magnesium alloy as a single homogeneous or also heterogeneous layer. Therefore it is preferred, if not even mandatory, that the inorganic coating of magnesium fluoride is applied directly to the stent surface. The stent surface should not have another coating such as a carbide layer, nitride layer, magnesium oxide layer or a layer of DLC (diamond like carbon) or the like.

On the contrary, it is possible to apply a further preferably organic coating to the organic coating of organic polymer or organic polymer mixture. Such an additional outer and preferably organic layer coating can serve, for example, to improve the lubrication properties of the stent surface or serve as a matrix for an active agent such as an antirestenotic active agent as described herein.

Magnesium Alloy

The inner scaffold or the body of the vessel graft or the stent according to the invention consists of a magnesium alloy. This alloy consists of 0.1 to 15.5% by wt. Dy and 0.01 to 1.5% by wt. Nd or 0.01 to 1.5% by wt. Eu or 0.01 to 1.5% by wt. Nd and Eu together, 0.0% by wt.-2.0% by wt. zinc and 0.0% by wt.-1.0% by wt. zirconium, the remainder being up to 100% by weight of Mg. This means that these alloys contain 80.0% by wt. to 99.89% by wt. magnesium and preferably 80.0% by wt. to 97.0% by wt. magnesium and further preferably 85.0% by wt. to 95.0% by wt. magnesium. This alloy may also contain other metals and unavoidable impurities. Preferred ranges for the components Dy, Nd, Eu, Zn and Zr are described in detail below.

With other words, the magnesium alloy of which the inner scaffold or the body of the vessel graft or of the stent according to the invention consists comprises

| | |
|---|---|
| 0.1% by wt. to 15.5% by wt. | Dy and |
| 0.01% by wt. to 1.5% by wt. | Nd or |
| 0.01% by wt. to 1.5% by wt. | EU or |
| 0.01% by wt. to 1.5% by wt. | Nd and Eu together |
| 0.0% by wt. to 2.0% by wt. | zinc and |
| 0.0% by wt. to 1.0% by wt. | zirconium and |
| at least 80.0% by wt. | magnesium. |

The inner scaffold of the vessel graft is preferably of magnesium alloys comprising 0.1 to 15.5% by wt. Dy and 0.01 to 1.5% by wt. Nd or 0.01 to 1.5% by wt. Eu or 0.01 to 1.5% by wt. Nd and Eu together, 0.0% by wt.-2.0% by wt., preferably to 1.5% by wt. zinc and further comprising 0.1% by wt.-0.75% by wt. zirconium. Also these alloys may further contain unavoidable impurities.

Particularly preferred is if the inner scaffold of a stent according to the invention consists of magnesium alloy, which in relation to the total weight of the alloy (in % by wt.) contains following components:

| | |
|---|---|
| 81.25% by wt-99.89% by wt | magnesium |
| 0.1% by wt.-15.0% by wt. | dysprosium |
| 0.01% by wt.-1.5% by wt. | neodymium and/or europium |
| 0.0% by wt.-1.5% by wt. | zinc |
| 0.0% by wt.-0.75% by wt. | zirconium | wherein the stent has an inorganic coating comprising magnesium fluoride and an organic coating.

Magnesium (Mg) as main component of the alloy has been chosen as Mg is biologically degradable and an essential element of the body which does not accumulate in the body in a way that it is harmful. Excessive magnesium is generally excreted naturally. The magnesium alloys of the inventive vessel grafts consist of at least 80% by wt. of magnesium.

For the production of stents, especially strength characteristics and the corrosion behavior have been taken into consideration to provide an alloy being as strong and corrosion-resistant as possible, wherein the control of the corrosion behavior is adjusted via the inorganic coating and the organic coating.

It has been found that the minimum level of corrosion of the magnesium alloys, as described herein, occurs at a content of 10% by weight Dy. Thus, it is especially preferred if the content of dysprosium in the respective alloys is approximately 10% by weight ±2% by weight. The corrosion is the crucial property for the degradation rate of the stent in the vessel. It is important that a biodegradable stent does not lose its stability too early, so that no fragments are detached and the stability is ensured by the stent until it can be reapplied by the vessel alone and until the stent has grown into the vessel wall. The inorganic coating and the organic coating serve in particular to adjust the resorption kinetics and to control the degradation rate of the stent, so that the stent is not dissolved before it has grown into the vessel wall. Furthermore, dysprosium together with magnesium form intermetallic precipitates. The high solubility of dysprosium in magnesium ensures that the required heat treatments in the production of stents can be performed successfully, that the precipitates are dissolved and precisely precipitated again and that properties such as strength, ductility and corrosion behavior can be adjusted over a wide range in this way.

Neodymium and europium have also shown no negative effects on cells in vitro. Europium was even better tolerated than neodymium. Both elements are practically insoluble in magnesium and form intermetallic phases with magnesium, which are also not dissolved by the heat treatments required for the production of stents. These precipitates are localized on the grain boundaries and stabilize these so that the fine grain of the forming is retained. According to the invention, it has been shown that 1% by weight of neodymium or 1% by weight of europium or 1% by weight of europium and neodymium together are sufficient.

Zinc improves the casting characteristics of the magnesium alloy and has a strengthening effect. Thus, the fatigue behavior and tensile strength can be increased by addition of zinc up to 3% by weight. The tensile strength should preferably be as high as possible and preferably more than 180 MPa (≥180 MPa), further preferred more than 200 MPa (≥200 MPa). However, the tendency for hot crack formation increases with more than 1% by weight Zn (see FIG. 8). Thereby, micropores are formed, which negatively affect tensile strength and ductility of an alloy. They act as inner notches so that in tensile tests a material fails generally clearly below the maximal achievable strength at a fractional amount of the theoretical ductility. In general, a disadvantageous effect on the processing behavior and the mechanical properties of the alloys described herein is shown with more than 2% by weight zinc. Zinc is an essential element for human beings, which is part of many enzymes and has many functions. Among others, zinc has an anti-inflammatory effect. Nevertheless, with high doses acute poisoning can occur and a long-term supply causes disorders, especially of the iron and copper metabolism (cf. Guidelines for drinking-water quality, World Health Organization, 1996). Therefore, toxic side effects cannot be excluded at a content of 4% by weight zinc and more. Thus, the amount of zinc should be below 2.0% by weight, preferred below 1.8% by weight, more preferred below 1.6% by weight, even more preferred below 1.4% by weight and especially preferred below 1.2% by weight. In several embodiments of the present invention the magnesium alloys of the inventive stents are free of zinc.

Zirconium (Zr) may be present in the magnesium alloy in addition to zinc or also instead of zinc. Here, Zr is used as grain refiner. For a magnesium alloy one can alloy Zr in a range up to approximately 0.75% by weight for the production of the inventive stents. Also larger amounts of Zr of 2% by weight or also 3% by weight result in a similar well grain refinement, but increase the price of the alloy remarkably and, in addition, lead to an embrittlement of the alloy, which in turn leads to a decrease of the ductility. Since, in regard to grain refinement, the results achieved with significantly smaller quantities of Zr of 0.0% by weight to 0.50% by weight were as good as with 1% by weight, 2% by weight or 3% by weight and in addition with an amount of Zr below 0.75% by weight no embrittlement occurs, 0.0% by weight to 0.1% by weight and further preferred 0.1% by weight to 0.75% by weight zirconium are used according to the invention.

The influence of Zr has been exemplarily examined with the magnesium alloy containing 10% by weight Dy and 1% by weight Nd. Permanent molt direct chill casting ("Tütengußverfahren") has been used as production process. For materials produced by permanent molt direct chill casting, one can assume that a cast part shows a homogenous microstructure and that the alloying elements are homogenously distributed too. However, the structure is comparatively rough and the grain size is in the range of several millimeters (FIG. 1). The inventors could show that addition of only 0.6% by weight Zr led to a clear reduction of grain size (FIG. 2). Therefore, three differently large proportions of Zr (0.2, 0.4, 0.6% by weight) and their influence to the forming structure have been examined. For determining the grain size the linear intercept method has been applied. Surprisingly, already a small proportion of 0.2% by weight results in a significant grain refinement (FIG. 2) and the grain size is in the range of about 102 μm. Addition of 0.4 or 0.6% by weight results in grain sizes of about 68 μm, respectively 64 μm (FIGS. 4 and 5). One can therefore conclude that already an addition of 0.2% by weight Zr causes an effective grain refinement and that surprisingly the total amount of Zr can be activated for grain refinement. This reduces the costs for Zr alone by about 50%.

Therefore, it is preferred, if an alloy according to the invention has further 0.02-0.80% by weight, preferred 0.04-0.60% by weight, preferred 0.05-0.55% by weight, further preferred 0.06-0.50% by weight, even more preferred 0.07-0.45% by weight, even more preferred 0.08-0.40% by weight, even more preferred 0.09-0.35% by weight, even more preferred 0.10-0.30% by weight, even more preferred 0.12-0.28% by weight and especially preferred 0.15-0.25% by weight zirconium.

The present invention further relates to stents of biologically degradable magnesium alloys, which contain the following components based on the total weight of the alloy (given in % per wt.):

| | |
|---|---|
| 80% by wt-94.9% by wt | magnesium |
| 5.0% by wt.-13.0% by wt. | dysprosium |
| 0.1% by wt.-2.0% by wt. | neodymium |
| 0.0% by wt.-2.0% by wt. | zinc |
| 0.0% by wt.-3.0% by wt. | zirconium | wherein the stent has an inorganic coating comprising magnesium fluoride and an organic coating.

Optionally, the amount of neodymium in this alloy may be substituted by europium, or one may add further 0.1% by wt.-2.0% by wt europium.

It goes without saying that all components of an alloy must add up to 100% by wt. Unless not explicitly mentioned, the herein disclosed alloys may contain unavoidable impurities, which are in the range of the lower detection limit or in the range of 1 ppm up to 0.4% by wt., preferably up to 0.3% by wt., further preferably up to 0.2% by wt., and in particular preferably up to 0.1% by wt. Silicon as main ingredient of the impurities may reach already 0.3% by weight. Silicon (Si) should not be present in an amount over 0.4% by wt., preferably over 0.3% by wt., and more preferably over 0.2% by wt., in the alloy. It is therefore especially preferred if the unavoidable impurities except silicon represent in total less than 0.3% by weight, preferred less than 0.2% by weight, further preferred less than 0.1% by weight, further preferred less than 0.05% by weight and especially preferred less than 300 ppm. These impurities (including silicon) may also be present in the alloy, if they are not explicitly listed as an alloying element and, in the case not being mentioned, are added to the weight proportion of that component of the alloy, through which they have been introduced into the alloy.

The invention further comprises stents consisting of magnesium alloys composed of the following components based on the total weight of the alloy:

| | |
|---|---|
| 80.0% by wt.-99.9% by wt. | magnesium |
| 0.1% by wt.-13.0% by wt. | dysprosium |
| 0.0% by wt.-3.0% by wt. | neodymium |
| 0.0% by wt.-1.0% by wt. | zinc |

-continued

| | |
|---|---|
| 0.0% by wt.-1.0% by wt. | zirconium |
| 0.0% by wt.-2.0% by wt. | other metals, metal salts and non metals, which are commonly referred to as impurities, | wherein the stent has an inorganic coating comprising magnesium fluoride and an organic coating.

It is preferred, when the alloy of the invention has 0.1-20.0% by wt., preferably 0.15-19.0% by wt., preferably 0.16-18.0% by wt., preferably 0.17-17.0% by wt., preferably 0.18-17.0% by wt., preferably 0.19-16.5% by wt., preferably 2.0-16.0% by wt., preferably 2.1-16.0% by wt., preferably 2.2-15.0% by wt., preferably 2.2-14.0% by wt., preferably 2.3-13.0% by wt., preferably 2.4-13.5% by wt., preferably 2.5-13.0% by wt., preferably 2.6-12.5% by wt., preferably 2.7-12.7% by wt., preferably 2.8-12.4% by wt., preferably 2.9-12.0% by wt., preferably 3.0-12.2% by wt., preferably 3.1-12.0% by wt., preferably 3.2-11.5% by wt., preferably 3.3-11.5% by wt., preferably 3.4-11.0% by wt., and more preferred 0.35-11.0% by wt. dysprosium.

Preferably, the amount of neodymium is in the range of 0.0-8.0% by wt., more preferably from 0.1-5.0% by wt., still more preferably 0.2-4.0% by wt., even more preferably 0.3-3.5% by wt. and especially preferably of 0.5 to 3.2% by wt.

Together with neodymium (Nd) or instead of Nd also europium (Eu) in the alloy in proportions from 0.0-8.0% by wt., more preferably 0.1-5.0% by wt., even more preferably 0.2-4.0% by wt., still more preferably 0.3-3.5% by wt., especially preferably from 0.5-3.2% by wt.

It is further preferred that the sum of the weight proportions of Nd and Eu in the alloy is from 0.01-8.0% by wt., more preferably from 0.1 to 5.0% by wt., still more preferably 0.2-4.0% by wt., and especially preferably from 0.5-3.2% by wt.

The sum of the weight proportions of dysprosium and neodymium is preferably in the range of 1.1-18.0% by wt., more preferably between 1.6 to 15.5% by wt., even more preferably, and particularly preferably from 2.1 to 13.0% by wt.

It is further preferred that the alloy has furthermore 0.0-4.0% by wt., more preferably 0.0-3.0% by wt., still more preferably 0.0-2.0% by wt., even more preferably 0.1-1.5% by wt. and especially preferably 0.2-1.3% by wt. zinc (Zn).

In addition to the aforementioned components a magnesium alloy from which the basic scaffold of the inventive stent was made may also contain 0.0% by wt.-5.0% by wt., preferably 0.1% by wt.-4.0% by wt., more preferably 0.2% by wt.-3.0% by wt. and especially preferred in total not more than 2.5% by wt. other metals, metal salts, non-metals, carbon, sulfur, silicon, nitrogen, oxygen, and/or hydrogen.

Furthermore it is preferred that the elements beryllium, aluminium and manganese are each present below 300 ppm, preferably below 200 ppm and more preferably below 150 ppm in the magnesium alloys from which the basic scaffold of the inventive stent was made.

The maximum amount of 2.5% by wt. impurities includes the other metals or non-metals such as for example silicon, carbon, oxygen, nitrogen, hydrogen or sulfur, also if they are additionally explicitly listed. The term "impurities" as used herein refers to all alloy components except of magnesium, dysprosium, neodymium, europium, zinc and zirconium irrespective of explicitly mentioning these or not.

A preferred embodiment of the invention relates to stents consisting of a biologically degradable magnesium alloy comprising or consisting of the following components:

| | |
|---|---|
| 80.0% by wt.-99.5% by wt. | magnesium |
| 0.1% by wt.-13.0% by wt. | dysprosium |
| 0.2% by wt.-4.0% by wt. | neodymium |
| 0.2% by wt.-3.0% by wt. | zinc | wherein the stent has an inorganic coating comprising magnesium fluoride and an organic coating.

A preferred embodiment of the invention relates to stents consisting of a biologically degradable magnesium alloy comprising or consisting of the following components:

| | |
|---|---|
| 88% by wt. | magnesium |
| 10% by wt. | dysprosium |
| 1% by wt. | neodymium |
| 1% by wt. | zinc | wherein the stent has an inorganic coating comprising magnesium fluoride and an organic coating.

A preferred embodiment of the invention relates to stents consisting of a biologically degradable magnesium alloy comprising or consisting of the following components:

| | |
|---|---|
| 80.0% by wt.-99.65% by wt. | magnesium |
| 0.1% by wt.-14.0% by wt. | dysprosium |
| 0.2% by wt.-4.0% by wt. | neodymium |
| 0.05% by wt.-2.0% by wt. | zirconium | wherein the stent has an inorganic coating comprising magnesium fluoride and an organic coating.

A further preferred embodiment of the invention relates to stents consisting of a biologically degradble magnesium alloy comprising or consisting of the following components:

| | |
|---|---|
| 88% by wt. | magnesium |
| 10% by wt. | dysprosium |
| 1% by wt. | neodymium |
| 1% by wt. | zirconium | wherein the stent has an inorganic coating comprising magnesium fluoride and an organic coating.

A preferred embodiment of the invention relates to stents consisting of a biologically degradable magnesium alloy comprising or consisting of the following components:

| | |
|---|---|
| 80.0% by wt.-99.45% by wt. | magnesium |
| 0.1% by wt.-13.0% by wt. | dysprosium |
| 0.2% by wt.-4.0% by wt. | neodymium |
| 0.2% by wt.-2.0% by wt. | zinc |
| 0.05% by wt.-1.0% by wt. | zirconium | wherein the stent has an inorganic coating comprising magnesium fluoride and an organic coating.

A particularly preferred embodiment of the invention relates to stents consisting of a biologically degradable magnesium alloy comprising or consisting of the following components:

| | |
|---|---|
| 87% by wt. | magnesium |
| 10% by wt. | dysprosium |
| 1% by wt. | neodymium |
| 1% by wt. | zinc |
| 1% by wt. | zirconium | wherein the stent has an inorganic coating comprising magnesium fluoride and an organic coating.

A preferred embodiment of the invention relates to stents consisting of a biologically degradable magnesium alloy comprising or consisting of the following components:

| | |
|---|---|
| 80.0% by wt.-99.4% by wt. | magnesium |
| 0.1% by wt.-13.0% by wt. | dysprosium |
| 0.2% by wt.-3.5% by wt. | neodymium |
| 0.2% by wt.-1.0% by wt. | zinc |
| 0.1% by wt.-2.5% by wt. | impurities such as other metals, metal salts and non metals, | wherein the stent has an inorganic coating comprising magnesium fluoride and an organic coating.

A preferred embodiment of the invention relates to stents consisting of a biologically degradable magnesium alloy comprising or consisting of the following components:

| | |
|---|---|
| 80.0% by wt.-99.6% by wt. | magnesium |
| 0.1% by wt.-13.0% by wt. | dysprosium |
| 0.1% by wt.-3.0% by wt. | neodymium |
| 0.1% by wt.-2.0% by wt. | zinc |
| 0.1% by wt.-2.0% by wt. | impurities such as other metals, metal salts and non metals, | wherein the stent has an inorganic coating comprising magnesium fluoride and an organic coating.

A further preferred embodiment of the invention relates to stents consisting of a biologically degradable magnesium alloy comprising or consisting of the following components:

| | |
|---|---|
| 80.55% by wt.-99.6% by wt. | magnesium |
| 0.1% by wt.-13.0% by wt. | dysprosium |
| 0.1% by wt.-3.0% by wt. | neodymium |
| 0.1% by wt.-0.75% by wt. | zirconium |
| 0.1% by wt.-2.0% by wt. | impurities such as other metals, metal salts and non metals, | wherein the stent has an inorganic coating comprising magnesium fluoride and an organic coating.

A further preferred embodiment of the invention relates to stents consisting of a biologically degradable magnesium alloy comprising or consisting of the following components:

| | |
|---|---|
| 80.55% by wt.-99.5% by wt. | magnesium |
| 0.1% by wt.-11.0% by wt. | dysprosium |
| 0.1% by wt.-3.2% by wt. | neodymium |
| 0.1% by wt.-2.0% by wt. | zinc |
| 0.1% by wt.-0.75% by wt. | zirconium |
| 0.1% by wt.-2.5% by wt. | impurities such as other metals, metal salts and non metals, | wherein the stent has an inorganic coating comprising magnesium fluoride and an organic coating.

A further preferred embodiment of the invention relates to stents consisting of a biologically degradable magnesium alloy comprising or consisting of the following components:

| | |
|---|---|
| 80.25% by wt.-94.6% by wt. | magnesium |
| 5.0% by wt.-12.5% by wt. | dysprosium |
| 0.1% by wt.-2.0% by wt. | europium |
| 0.1% by wt.-2.0% by wt. | zinc |
| 0.1% by wt.-0.75% by wt. | zirconium |
| 0.1% by wt.-2.5% by wt. | impurities such as other metals, metal salts and non metals, | wherein the stent has an inorganic coating comprising magnesium fluoride and an organic coating.

A further preferred embodiment of the invention relates to stents consisting of a biologically degradable magnesium alloy comprising or consisting of the following components:

| | |
|---|---|
| 80.0% by wt.-99.4% by wt. | magnesium |
| 0.1% by wt.-11.0% by wt. | dysprosium |
| 0.1% by wt.-2.0% by wt. | europium |
| 0.1% by wt.-3.0% by wt. | neodymium |
| 0.1% by wt.-2.0% by wt. | zinc |
| 0.1% by wt.-1.0% by wt. | zirconium |
| 0.1% by wt.-1.0% by wt. | impurities such as other metals, metal salts and non metals, | wherein the stent has an inorganic coating comprising magnesium fluoride and an organic coating.

A further preferred embodiment of the invention relates to stents consisting of a biologically degradable magnesium alloy comprising or consisting of the following components:

| | |
|---|---|
| 80.0% by wt.-99.65% by wt. | magnesium |
| 0.1% by wt.-15.0% by wt. | dysprosium |
| 0.2% by wt.-3.0% by wt. | europium |
| 0.05% by wt.-2.0% by wt. | zirconium | wherein the stent has an inorganic coating comprising magnesium fluoride and an organic coating.

A further preferred embodiment of the invention relates to stents consisting of a biologically degradable magnesium alloy comprising or consisting of the following components:

| | |
|---|---|
| 88% by wt. | magnesium |
| 10% by wt. | dysprosium |
| 1% by wt. | europium |
| 1% by wt. | zirconium | wherein the resorbable stent is surrounded by an inorganic biologically degradable coating and an organic coating.

A further preferred embodiment of the invention relates to stents consisting of a biologically degradable magnesium alloy comprising or consisting of the following components:

| | | |
|---|---|---|
| 80.0% by wt. - | 99.75% by wt. | magnesium |
| 0.1% by wt. - | 15.0% by wt. | dysprosium |
| 0.2% by wt. - | 4.0% by wt. | europium |
| 0.05% by wt. - | 4.0% by wt. | zinc | wherein the stent has an inorganic coating comprising magnesium fluoride and an organic coating.

A further preferred embodiment of the invention relates to stents consisting of a biologically degradable magnesium alloy comprising or consisting of the following components:

| | |
|---|---|
| 88% by wt. | magnesium |
| 10% by wt. | dysprosium |
| 1% by wt. | europium |
| 1% by wt. | zinc | wherein the stent has an inorganic coating comprising magnesium fluoride and an organic coating.

A further preferred embodiment of the invention relates to stents consisting of a biologically degradable magnesium alloy comprising or consisting of the following components:

| | | |
|---|---|---|
| 80.0% by wt. - | 99.6% by wt. | magnesium |
| 0.1% by wt. - | 14.0% by wt. | dysprosium |
| 0.2% by wt. - | 2.0% by wt. | europium |
| 0.05% by wt. - | 2.0% by wt. | zinc |
| 0.05% by wt. - | 2.0% by wt. | zirconium | wherein the stent has an inorganic coating comprising magnesium fluoride and an organic coating.

A further preferred embodiment of the invention relates to stents consisting of a biologically degradable magnesium alloy comprising or consisting of the following components:

| | |
|---|---|
| 87% by wt. | magnesium |
| 10% by wt. | dysprosium |
| 1% by wt. | europium |
| 1% by wt. | zinc |
| 1% by wt. | zirconium | wherein the stent has an inorganic coating comprising magnesium fluoride and an organic coating.

A particularly preferred embodiment of the invention relates to stents consisting of a biologically degradable magnesium alloy comprising or consisting of the following components:

| | |
|---|---|
| 87.8% by wt. | magnesium |
| 10% by wt. | dysprosium |
| 1.0% by wt. | europium |
| 1.0% by wt. | zinc |
| 0.2% by wt. | zirconium | wherein the stent has an inorganic coating comprising magnesium fluoride and an organic coating.

A further particularly preferred embodiment of the invention relates to stents consisting of a biologically degradable magnesium alloy comprising or consisting of the following components:

| | |
|---|---|
| 86.8% by wt. | magnesium |
| 10% by wt. | dysprosium |
| 1.0% by wt. | europium |
| 1.0% by wt. | zinc |
| 0.2% by wt. | zirconium | wherein the stent has an inorganic coating comprising magnesium fluoride and an organic coating.

A further particularly preferred embodiment of the invention relates to stents consisting of a biologically degradable magnesium alloy comprising or consisting of the following components:

| | |
|---|---|
| 87.8% by wt. | magnesium |
| 10% by wt. | dysprosium |
| 1.0% by wt. | neodymium |
| 1.0% by wt. | europium |
| 1.0% by wt. | zinc |
| 0.2% by wt. | zirconium | wherein the stent has an inorganic coating comprising magnesium fluoride and an organic coating.

All percentages by weight specified in this disclosure refer to the total weight of the corresponding alloy. Thus it applies to all compositions, mentioned herein, that the sum of all components in total must add up to 100.00% by wt. That means, after addition of all listed components of the magnesium alloy, the difference to 100% by wt. is magnesium as the main component.

Furthermore, the present invention comprises preferably stents, which basic scaffold consists of biologically degradable magnesium alloys, which comprise yttrium (Y), gadolinium (Gd), calcium (Ca), manganese (Mn), cerium (Ce), scandium (Sc), Indium (In), lithium (Li) or erbium (Er) as further components besides 80% by wt. magnesium, dysprosium, neodymium, europium, zinc, zirconium and unavoidable, production-related impurities. That is, it is preferred, if the components of the alloy, besides the magnesium as basis, are selected from the following group consisting or comprising of: dysprosium, neodymium, europium, zinc, zirconium, yttrium, gadolinium, erbium, calcium, manganese, cerium, scandium, indium, lithium and unavoidable, production-related impurities. In several embodiments of the present invention the magnesium alloys of the stents are free of yttrium.

Consequently, a further preferred embodiment of the invention relates to stents consisting of a biologically degradable magnesium alloy comprising or consisting of the following components:

| | | |
|---|---|---|
| 93.0% by wt. - | 94.0% by wt. | magnesium |
| 0.3% by wt. - | 0.4% by wt. | dysprosium |
| 2.0% by wt. - | 2.1% by wt. | neodymium |
| 0.3% by wt. - | 0.5% by wt. | gadolinium |
| 0.3% by wt. - | 0.4% by wt. | zirconium |
| 3.4% by wt. - | 3.8% by wt. | yttrium |
| 0.0% by wt. - | 0.02% by wt. | erbium | wherein the stent has an inorganic coating comprising magnesium fluoride and an organic coating.

A further preferred embodiment of the invention relates to stents consisting of a biologically degradable magnesium alloy comprising or consisting of the following components:

| | | |
|---|---|---|
| 92.0% by wt. - | 93.0% by wt. | magnesium |
| 0.9% by wt. - | 1.1% by wt. | dysprosium and gadolinium together |
| 2.1% by wt. - | 2.3% by wt. | neodymium |
| 0.4% by wt. - | 0.6% by wt. | zirconium |
| 3.9% by wt. - | 4.3% by wt. | yttrium | wherein the stent has an inorganic coating comprising magnesium fluoride and an organic coating.

A further preferred embodiment of the invention relates to stents consisting of a biologically degradable magnesium alloy comprising or consisting of the following components:

| | | |
|---|---|---|
| 91.0% by wt. - | 92.0% by wt. | magnesium |
| 0.7% by wt. - | 0.8% by wt. | dysprosium |
| 0.6% by wt. - | 0.8% by wt. | gadolinium |
| 1.9% by wt. - | 2.1% by wt. | neodymium |
| 0.6% by wt. - | 0.8% by wt. | zirconium |
| 3.9% by wt. - | 4.2% by wt. | yttrium | wherein the stent has an inorganic coating comprising magnesium fluoride and an organic coating.

A further preferred embodiment of the invention relates to stents consisting of a biologically degradable yttrium free magnesium alloy comprising or consisting of the following components:

| | | |
|---|---|---|
| 93.7% by wt. - | 96.2% by wt. | magnesium |
| 1.0% by wt. - | 1.5% by wt. | gadolinium |
| 2.0% by wt. - | 3.1% by wt. | neodymium |
| 0.5% by wt. - | 0.7% by wt. | zirconium |
| 0.1% by wt. - | 0.5% by wt. | calcium |
| 0.2% by wt. - | 0.5% by wt. | zinc | wherein the stent has an inorganic coating comprising magnesium fluoride and an organic coating.

A further preferred embodiment of the invention relates to stents consisting of a biologically degradable magnesium alloy comprising or consisting of the following components:

| | |
|---|---|
| 96.9% by wt. | magnesium |
| 2.5% by wt. | neodymium |
| 0.4% by wt. | zirconium |
| 0.2% by wt. | zinc | wherein the stent has an inorganic coating comprising magnesium fluoride and an organic coating.

A further preferred embodiment of the invention relates to stents consisting of a biologically degradable magnesium alloy comprising or consisting of the following components:

| | |
|---|---|
| 97.45% by wt. | magnesium |
| 0.75% by wt. | neodymium |
| 1.80% by wt. | manganese | wherein the stent has an inorganic coating comprising magnesium fluoride and an organic coating.

A further preferred embodiment of the invention relates to stents consisting of a biologically degradable magnesium alloy comprising or consisting of the following components:

| | |
|---|---|
| 97.45% by wt. | magnesium |
| 0.75% by wt. | cerium |
| 1.80% by wt. | manganese | wherein the stent has an inorganic coating comprising magnesium fluoride and an organic coating.

A further preferred embodiment of the invention relates to stents consisting of a biologically degradable magnesium alloy comprising or consisting of the following components:

| | |
|---|---|
| 90.0% by wt. | magnesium |
| 3.0% by wt. | gadolinium |
| 2.4% by wt. | yttrium |
| 0.4% by wt. | zirconium |
| 4.2% by wt. | scandium | wherein the stent has an inorganic coating comprising magnesium fluoride and an organic coating.

A further preferred embodiment of the invention relates to stents consisting of a biologically degradable magnesium alloy comprising or consisting of the following components:

| | |
|---|---|
| 90.0% by wt. | magnesium |
| 3.0% by wt. | neodymium |
| 2.4% by wt. | yttrium |
| 0.4% by wt. | zirconium |
| 5.2% by wt. | scandium |
| 2.0% by wt. | indium | wherein the stent has an inorganic coating comprising magnesium fluoride and an organic coating.

A further preferred embodiment of the invention relates to stents consisting of a biologically degradable magnesium alloy comprising or consisting of the following components:

| | |
|---|---|
| 96.0% by wt. | magnesium |
| 4.0% by wt. | lithium | wherein the stent has an inorganic coating comprising magnesium fluoride and an organic coating.

The resorbable stent according to the invention is preferably a stent for blood vessels, urinary tracts, respiratory tracts, biliary tracts or the digestive tract. In turn, among these stents the vascular implants or stents for blood vessels or more generally for the cardiovascular system are preferred.

The herein disclosed magnesium alloys are selected in such a way that they are particularly suitable for production of resorbable or degradable endoprotheses and particularly of vascular implants or stents respectively.

Furthermore, the present invention comprises a resorbable stent or a resorbable vascular implant consisting of a magnesium alloy as disclosed herein, wherein the stent has an inorganic coating comprising magnesium fluoride and an organic coating. The inorganic coating of the stents according to the invention is a coating, which was applied on the surface of the stent, comprising at least 50%, preferably at least 80%, and even more preferably at least 90% magnesium fluoride. The inorganic coating may further also be biodegradable. Also the organic coating may be biodegradable.

The terms "bioresorbable" or "biodegradable", as used herein, means that the implant slowly dissolves in a human or animal organism over a certain time and at some point only its degradation products are present in the body in a dissolved form. At this point in time, solid components or fragments of the implant are not present anymore. The degradation products should be substantially harmless in physiological terms and lead to ions or molecules which occur in the organism anyway, or can be degraded by the organism to harmless substances, or can be excreted.

This means that a stent is biodegradable if the stent exhibits a significant weight reduction or chemical transformation after being inserted into a patient. Weight reduction may occur, e.g. by dissolution of the material. Preferred chemical transformations are oxidation/reduction, hydrolysis, substitution, and/or addition. Erosion can be the result of a chemical interaction of the stent with the body (the body itself or body fluids). Preferably, erosion occurs to a desired extent in a time frame that ensures that the essential functions of the stent such as lumen support are maintained for as long as needed. Stents of the biologically biodegradable magnesium alloys having inorganic coatings as disclosed herein are resorbed within a period of 8 to 50 weeks, preferably 10 to 30 weeks, under physiological conditions.

Stents are hereby grid-shaped or net-shaped endoprostheses which are inserted into a hollow organ or a body cavity to keep it open. The basic scaffold of a stent, which is herein referred to metallic struts without coating, is not a solid tube but a mesh. If, for example, the basic scaffold of a vascular stent is considered, it is cut from a solid tube, e.g. by a laser, so that as thin as possible individual struts are formed, which are interconnected. The arrangement and shaping of the struts and nodal points is called stent design. In the sense of the present invention, all common stent geometries can be used as magnesium stent according to the invention.

In addition, a method for producing resorbable stents is disclosed comprising the following steps:
a) providing a bioresorbable magnesium alloy as disclosed herein,
b) producing a wire or rod or tube from the alloy obtained in step a) by extrusion,
c) producing a tube from the wire or rod obtained according to step b),
d) cutting stents from the tube obtained according to step b) or c); and
e) applying an inorganic coating comprising magnesium fluoride to at least a portion of the surface of the stent obtained according to step d),
(f) applying an organic coating to at least part of the inorganic coating applied in accordance with step e).

The invention also comprises resorbable stents obtained according to the previous method. In step d), a laser is preferably used to cut the stents obtained from the tube according to step b) or c). In order to produce a resorbable stent according to the invention, a wire or rod made of the alloy can initially be produced after step a), before a tube made of the wire or rod is obtained in step c). An embodiment of the present invention therefore relates to a method for the production of resorbable stents comprising the following steps:
a) providing a bioresorbable magnesium alloy as disclosed herein,
b) producing a wire or rod from the alloy obtained according to step a) by extrusion,
c) producing a tube from the wire or rod obtained according to step b),
d) cutting stents from the tube obtained according to step c); and
e) applying an inorganic coating to at least a portion of the surface of the stent obtained according to step d),
f) applying an organic coating to at least part of the inorganic coating applied in accordance with step e).

The invention also includes resorbable stents obtained according to the aforementioned method.

Furthermore, the tube can already be obtained in step b), so that a rod or wire does not have to be produced first. The stent is then cut out of the tube according to step b). Thus, a further embodiment of the present invention is a method for the production of resorbable stents, comprising the following steps:
a) providing a bioresorbable magnesium alloy as disclosed herein,
b) production of a tube from the alloy obtained according to step a) by extrusion,
c) cutting stents from the tube obtained according to step b) and
d) applying an inorganic coating to at least a portion of the surface of the stent obtained according to step c),
e) applying an organic coating to at least part of the inorganic coating applied in accordance with step d).

The invention also comprises resorbable stents obtained according to the aforementioned method.

In order to obtain a magnesium alloy according to the invention further steps may be carried out prior to step a). In these steps, the components of the magnesium alloys are melted in a smoothed steel crucible by sequential addition in form of pure elements or as master alloys at a molten bath temperature of 660-740° C. in a smoothed steel crucible. All melting operations are carried out under inert gas. After addition of the alloying elements the melt is stirred mechanically. In a next step, the melt is transferred into a thin-walled coquille, which was preheated to a temperature of 600° C. In a last step, the coquille is immersed in a water bath having a temperature of 15-20° C.

The invention also relates to magnesium alloys which are melted in a vacuum furnace or a protective gas furnace before step a). Generally, melting takes place in a melting or casting furnace. In case of melting in a vacuum furnace; the alloy is melted under reduced pressure. In case of an inert gas furnace, an inert gas is used to protect the alloy from undesired gases during the melting of the alloy.

In an animal experiment study (see example 7) on effectiveness and harmlessness of stents of magnesium alloys as disclosed herein it could be shown that the stents according to the invention or vascular implants of the magnesium alloys as disclosed herein can be crimped on a balloon without any problems. The implantation of the stents was made without occurrence of known complications, like stent malapposition, thromboses or dissection. Already after 4 weeks, a complete re-endothelialization of the stented vessel segments has been observed. This indicates that no excessive inflammation reactions occurred and the magnesium alloys according to the invention have caused no intolerance reactions in the tissue of the vessel. The rate of restenosis was in the range of values of common bare metal stents (BMS) of the prior art, respectively in the range of the "worser" drug-eluting stents (DES) (cf. figures to the talk of R.A. Costa: given within the Euro-PCR, Paris, May 2011).

Furthermore, the inner metallic scaffold of the inventive stents of a biologically degradable magnesium alloy as described herein, has preferably the property to dissolves more rapidly than the polymeric coating, i.e. the inner structure of the vessel graft is degraded more rapidly under physiological conditions than the polymeric coating. When using different organic compounds or different mixtures of organic compounds for an organic coating of a stent, there is further the possibility of using organic compounds which differ in degradation time or biostability.

The organic coating for all herein disclosed magnesium stents may comprise or consists of one or more biostable or biodegradable substances. Preferably, the organic coating consists or comprises one or more organic polymers. Therefore, the present invention relates to stents of biologically degradable magnesium alloys consisting of a basic scaffold of a biodegradable magnesium alloy having at least 80% by wt. magnesium as disclosed herein, an inorganic coating comprising magnesium fluoride and an organic coating comprising or consisting of one or more substances selected from the group comprising or consisting of: polyvinyl pyrrolidone, glycerine, polyhydroxyethyl methacrylates, polyethylene glycole, polypropylene glycole, polyvinyl alcohol, polydioxanone, polycaprolactone, polygluconate, poly(lactic acid)-polyethylene oxide-copolymer, modified cellulose, polyhydroxybutyrate, polyamino acids, polyphosphate esters, polyvalerolactones, poly-ε-decalactones, polylactonic acid, polyglycolic acid, polylactides, preferably poly(L-lactide), poly(D,L-lactide), and copolymers as well as blends such as poly(L-lactide-co-glycolide), poly(D,L-lactide-co-glycolide), poly(L-lactide-co-D,L-lactide), poly(L-lactide-co-trimethylene carbonate) (PTMC), polyglycolides, copolymers of the polylactides and polyglycolides, poly-ε-caprolactone, polyhydroxybutyric acid, polyhydroxybutyrates, polyhydroxyvalerates, polyhydroxybutyrate-co-valerates, poly(1,4-dioxane-2,3-dione), poly(1,3-dioxane-2-one), poly-para-dioxanones, polyanhydrides, polymaleic acid anhydrides, polyhydroxy methacrylates, fibrin, polycyanoacrylates, polycaprolactone dimethylacrylates, poly-b-maleic acid, polycaprolactone butyl acrylates, multiblock polymers from oligocaprolactonediols and oligodioxanonediols, polyether ester multiblock polymers from PEG and polybutylene terephthalate, polypivotolactones, polyglycolic acid trimethyl carbonates, polycaprolactone glycolides, poly(g-ethyl glutamate), poly(DTH-iminocarbonate), poly(DTE-co-DT-carbonate), poly(bisphenol A-iminocarbonate), polyorthoesters, polyglycolic acid trimethyl carbonates, polytrimethyl carbonates, polyiminocarbonates, polyvinyl alcohols, polyester amides, glycolized polyesters, polyphosphoesters, polyphosphazenes, poly[p-carboxyphenoxy)propane], polyhydroxy pentanoic acid, polyanhydrides, polyethylene oxide propylene oxide, soft polyurethanes, polyurethanes having amino acid residues in the backbone, polyetheresters such as polyethylene oxide, polyalkene oxalates, polyorthoesters as well as copolymers thereof, lipids, waxes, oils, polyunsaturated fatty acids, eicosapentaenoic acid, timnodonic acid, docosahexaenoic acid, arachidonic acid, linoleic acid, α-linolenic acid, γ-linolenic acid, carrageenans, fibrinogen, agar-agar, starch, collagen, protein based polymers, polyamino acids, synthetic polyamino acids, zein, polyhydroxyalkanoates, pectic acid, actinic acid, carboxymethyl sulfate, albumin, hyaluronic acid, chitosan and its derivatives, heparan sulfates and its derivates, heparins, chondroitin sulfate, dextran, ß-cyclodextrins, copolymers with PEG and polypropylene glycol, gum arabic, guar, gelatin, collagen, collagen N-hydroxysuccinimide, lipids, phospholipids, polyacrylic acid, polyacrylates, polymethyl methacrylate, polybutyl methacrylate, polyacrylamide, polyacrylonitriles, polyamides, polyetheramides, polyethylene amine, polyimides, polycarbonates, polycarbourethanes, polyvinyl ketones, polyvinyl halides, polyvinylidene halides, polyvinyl ethers, polyisobutylenes, polyvinyl aromatic compounds, polyvinyl esters, polyoxymethylenes, polytetramethylene oxide, polyethylene, polypropylene, polytetrafluoroethylene, polyurethanes, polyether urethanes, silicone polyether urethanes, silicone polyurethanes, silicone polycarbonate urethanes, polyolefin elastomers, polyisobutylenes, fluorosilicones, carboxymethyl chitosans, polyaryletheretherketones, polyetheretherketones, polyethylene terephthalate, polyvalerates, carboxymethylcellulose, cellulose, rayon, rayon triacetates, cellulose nitrates, cellulose acetates, hydroxyethyl cellulose, cellulose butyrates, cellulose acetate butyrates, ethyl vinyl acetate copolymers, polysulfones, epoxy resins, ABS resins, EPDM gums, silicones such as polysiloxanes, polydimethylsiloxanes, polyvinyl halogens, cellulose ethers, cellulose triacetates, shellac, poly-para-xylylenes (Parylenes) such as Parylene N, Parylene C and/or Parylene D, and copolymers and/or mixtures of the aforementioned polymers.

Preferred polymers for the outer organic coating are: polyvinyl pyrrolidone, polyhydroxyethyl methacrylates, polyethylene glycole, polypropylene glycole, polyvinyl alcohol, polydioxanone, polycaprolactone, poly(lactic acid)-polyethylene oxide-copolymer, polyvalerolactones, poly-ε-decalactones, polylactonic acid, polyglycolic acid, polylactides, preferably poly(L-lactide), poly(D,L-lactide), and copolymers as well as blends such as poly(L-lactide-co-glycolide), poly(D,L-lactide-co-glycolide), poly(L-lactide-co-D,L-lactide), poly(L-lactide-co-trimethylene carbonate) (PTMC), polyglycolides, copolymers of the polylactides and polyglycolides, caprolactone, polyhydroxybutyric acid, polyhydroxybutyrates, polyhydroxyvalerates, polyhydroxybutyrate-co-valerates, poly(1,4-dioxane-2,3-dione), poly(1,3-dioxane-2-one), poly-para-dioxanones, polymaleic acid anhydrides, polyhydroxy methacrylates, fibrin, polycaprolactone dimethylacrylates, polycaprolactone butyl acrylates, polycaprolactone glycolides, poly(g-ethyl glutamate), polyorthoesters, polyvinyl alcohols, polyester amides, polyurethanes polyacrylates, polymethyl methacrylate, polybutyl methacrylate, polyacrylamide, polyamides, polyetheramides, polyethylene amine, polyimides, polycarbonates, polycarbourethanes, polyvinyl ketones, polyvinyl ethers, polyisobutylenes, polyvinyl aromatic compounds, polyvinyl esters, polyoxymethylenes, polytetramethylene oxide, polyethylene, polypropylene, polytetrafluoroethylene, polyurethanes, polyether urethanes, silicone polyether urethanes, silicone polyurethanes, silicone polycarbonate urethanes, polyolefin elastomers, polyisobutylenes, fluorosilicones, polyaryletheretherketones, polyetheretherketones, polyethylene terephthalate, polyvalerates, polysulfones, polysiloxanes, polydimethylsiloxanes, poly-para-xylylenes (Parylenes) such as Parylene N, Parylene C and/or Parylene D. and copolymers and/or mixtures of the aforementioned polymers.

The organic coating of the stents according to the invention is metal-free, i.e. it does not contain any metal-containing compounds such as sodium, aluminium, magnesium, iron, zircon or titanium. The organic coating preferably contains no organometallic compounds, metal alkoxides or polymeric metal alkoxides. In particular the organic coating should not consist of titanium ethylene glycol, titanium propylene glycol, zircon ethylene glycol, zircon propylene glycol, hafnium ethylene glycol, hafnium propylene glycol or polyaluminium ethylene glycol. Organometallic compounds are referred to as compounds having a metal-carbon bond.

Thus, the present invention relates to a stent of a biologically degradable magnesium alloy having an inorganic coating comprising magnesium fluoride and having an organic coating, wherein the magnesium alloy contains at least 80% by wt. magnesium and the organic coating does not contain organometallic compounds, metal alkoxides or polymeric metal alkoxides.

Parylene is mostly the designation for completely linear, semi-crystalline, non-crosslinked aromatic polymers. The different polymers have different properties and can be divided into four basic types, namely parylene C, parylene D, parylene N and parylene F, the structure of which is shown in the following:

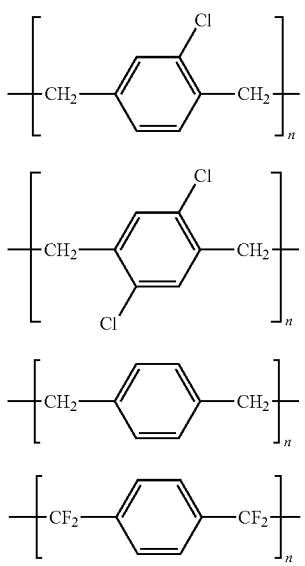

Parylen C

Parylen D

Parylen N

Parylen F

The simplest monomer in the parylene group is parylene N (poly-para-xylylene). There exist also two chlorinated polymers: parylene C (chloropoly-para-xylylene) and parylene D (di-chloro-poly-para-xylylene). In case of parylene F (poly(tetrafluoropara-xylylene)), the methylene units are fluorinated.

Parylene C has the lowest melting point of only 290° C. of the aforementioned parylenes, is characterized by good mechanical properties and corrosion resistance to corrosive gases as well as very low permeability to moisture. Parylene C is a biocompatible polymer and therefore suitable for use in physiological environments.

In a preferred embodiment of the present invention, the organic coating comprises one or more substances of the following group: poly-ε-caprolactone (PCL), poly(L-lactide-co-glycolide) (PLGA), poly(L-lactide) and parylene.

Therefore, the present invention relates particularly preferred to stents consisting of a biologically degradable magnesium alloy containing the following components based on the total weight of the alloy:

| | |
|---|---|
| 0.1% by wt.-15.5% by wt. | dysprosium |
| 0.01% by wt.-1.5% by wt. | neodymium and/or europium |
| 0.0% by wt.-2.0% by wt. | zinc |
| 0.0% by wt.-1.0% by wt. | zirconium |
| at least 80.0% by wt. comprising. | magnesium. |

A magnesium fluoride (MgF$_2$) having a layer thickness of 0.01 μm to 100 μm is applied to the stent of the aforementioned or herein disclosed magnesium alloys and on this magnesium fluoride layer an organic coating of polyvinyl pyrrolidone, polyhydroxyethyl methacrylates, polyethylene glycole, polypropylene glycole, polyvinyl alcohol, polydioxanone, polycaprolactone, polylactic acid)-polyethylene oxide-copolymer, polyhydroxybutyrates, polyvalerolactones, poly-ε-decalactones, polylactonic acid, polyglycolic acid, polylactides, preferably poly(L-lactide), poly(D,L-lactide), and copolymers as well as blends such as poly(L-lactide-co-glycolide), poly(D,L-lactide-co-glycolide), poly(L-lactide-co-D,L-lactide), poly(L-lactide-co-trimethylene carbonate) (PTMC), polyglycolides, copolymers of the polylactides and polyglycolides, poly-ε-caprolactone, polyhydroxybutyrates, polyhydroxyvalerates, polyhydroxybutyrate-co-valerates, poly(1,4-dioxane-2,3-dione), poly(1,3-dioxane-2-one), poly-para-dioxanones, polymaleic acid anhydrides, polyhydroxy methacrylates, fibrin, polycaprolactone dimethylacrylates, polycaprolactone butyl acrylates, polycaprolactone glycolides, poly(g-ethyl glutamate), polyorthoesters, polyvinyl alcohols, polyester amides, polyurethanes polyacrylates, polymethyl methacrylate, polybutyl methacrylate, polyacrylamide, polyamides, polyetheramides, polyethylene amine, polyimides, polycarbonates, polycarbourethanes, polyvinyl ketones, polyvinyl ethers, polyisobutylenes, polyvinyl aromatic compounds, polyvinyl esters, polyoxymethylenes, polytetramethylene oxide, polyethylene, polypropylene, polytetrafluoroethylene, polyurethanes, polyether urethanes, silicone polyether urethanes, silicone polyurethanes, silicone polycarbonate urethanes, polyolefin elastomers, polyisobutylenes, fluorosilicones, polyaryletheretherketones, polyetheretherketones, polyethylene terephthalate, polyvalerates, polysulfones, polysiloxanes, polydimethylsiloxanes, poly-para-xylylenes (Parylenes) such as Parylene N, Parylene C and/or Parylene D, and copolymers and/or mixtures of the aforementioned polymers having a layer thickness of 0.01 μm to 100 μm is applied.

Further preferred are stents consisting of a biologically degradable magnesium alloy containing the following components based on the total weight of the alloy:

| | |
|---|---|
| 0.1% by wt.-15.5% by wt. | dysprosium |
| 0.01% by wt.-1.5% by wt. | neodymium and/or europium |
| 0.0% by wt.-2.0% by wt. | zinc |
| 0.0% by wt.-1.0% by wt. | zirconium |
| rest up to 100.0% by wt. | magnesium. | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

Particular preferred is if the inner scaffold of a stent according to the invention consists of magnesium alloys containing the following components based on the total weight of the alloy (in % by wt.):

| | |
|---|---|
| 81.25% by wt.-98.8% by wt. | magnesium |
| 0.1% by wt.-15.0% by wt. | dysprosium |
| 0.5% by wt.-1.5% by wt. | neodymium and/or europium |
| 0.5% by wt.-1.5% by wt. | zinc |
| 0.1% by wt.-0.75% by wt. | zirconium | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

The present invention relates further preferably to stents of biologically degradable magnesium alloys containing the following components based on the total weight of the alloy (in % by wt.):

| | |
|---|---|
| 80.25% by wt.-99.4% by wt. | magnesium |
| 0.3% by wt.-15.0% by wt. | dysprosium |
| 0.1% by wt.-2.0% by wt. | neodymium |
| 0.1% by wt.-2.5% by wt. | zinc |
| 0.1% by wt.-0.75% by wt. | zirconium | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

The invention comprises further stents consisting of biologically degradable magnesium alloys consisting of the following components based on the total weight of the alloy (in % by wt.):

| | |
|---|---|
| 80.0% by wt.-99.7% by wt. | magnesium |
| 0.3% by wt.-13.0% by wt. | dysprosium |
| 0.0% by wt.-3.0% by wt. | neodymium |
| 0.0% by wt.-3.0% by wt. | zinc |
| 0.0% by wt.-1.0% by wt. | zirconium |
| 0.0% by wt.-2.0% by wt. | other metals, metal salts and non metals, which are commonly referred to as impurities, | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A preferred embodiment of the invention relates to stents consisting of a biologically degradable magnesium alloy comprising or consisting of the following components:

| | |
|---|---|
| 80.0% by wt.-99.5% by wt. | magnesium |
| 0.1% by wt.-13.0% by wt. | dysprosium |
| 0.2% by wt.-4.0% by wt. | neodymium |
| 0.2% by wt.-3.0% by wt. | zinc | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A preferred embodiment of the invention relates to stents consisting of a biologically degradable magnesium alloy comprising or consisting of the following components:

| | |
|---|---|
| 88% by wt. | magnesium |
| 10% by wt. | dysprosium |
| 1% by wt. | neodymium |
| 1% by wt. | zinc | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A preferred embodiment of the invention relates to stents consisting of a biologically degradable magnesium alloy comprising or consisting of the following components:

| | |
|---|---|
| 80.0% by wt.-99.65% by wt. | magnesium |
| 0.1% by wt.-14.0% by wt. | dysprosium |
| 0.2% by wt.-4.0% by wt. | neodymium |
| 0.05% by wt.-2.0% by wt. | zirconium | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A further preferred embodiment of the invention relates to stents consisting of a biologically degradable magnesium alloy comprising or consisting the following components:

| | |
|---|---|
| 88% by wt. | magnesium |
| 10% by wt. | dysprosium |
| 1% by wt. | neodymium |
| 1% by wt. | zirconium | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A preferred embodiment of the invention relates to stents consisting of a biologically degradable magnesium alloy comprising or consisting of the following components:

| | |
|---|---|
| 80.0% by wt.-99.45% by wt. | magnesium |
| 0.1% by wt.-13.0% by wt. | dysprosium |
| 0.2% by wt.-4.0% by wt. | neodymium |
| 0.2% by wt.-2.0% by wt. | zinc |
| 0.05% by wt.-1.0% by wt. | zirconium | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A particularly preferred embodiment of the invention relates to stents consisting of a biologically degradable magnesium alloy comprising or consisting of the following components:

| | |
|---|---|
| 87% by wt. | magnesium |
| 10% by wt. | dysprosium |
| 1% by wt. | neodymium |
| 1% by wt. | zinc |
| 1% by wt. | zirconium | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A preferred embodiment of the invention relates to stents consisting of a biologically degradable magnesium alloy comprising or consisting of the following components:

| | |
|---|---|
| 80.0% by wt.-99.4% by wt. | magnesium |
| 0.1% by wt.-13.0% by wt. | dysprosium |
| 0.2% by wt.-3.5% by wt. | neodymium |
| 0.2% by wt.-1.0% by wt. | zinc |
| 0.1% by wt.-2.5% by wt. | impurities such as other metals, metal salts and non metals, | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A preferred embodiment of the invention relates to stents consisting of a biologically degradable magnesium alloy comprising or consisting of the following components:

| | |
|---|---|
| 80.0% by wt.-99.6% by wt. | magnesium |
| 0.1% by wt.-13.0% by wt. | dysprosium |
| 0.1% by wt.-3.0% by wt. | neodymium |
| 0.1% by wt.-2.0% by wt. | zinc |
| 0.1% by wt.-2.0% by wt. | impurities such as other metals, metal salts and non metals, | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A further preferred embodiment of the invention relates to stents consisting of a biologically degradable magnesium alloy comprising or consisting of the following components:

| 80.55% by wt. - | 99.6% by wt.  | magnesium |
| 0.1% by wt. -   | 13.0% by wt.  | dysprosium |
| 0.1% by wt. -   | 3.2% by wt.   | neodymium |
| 0.1% by wt. -   | 0.75% by wt.  | zirconium |
| 0.1% by wt. -   | 2.5% by wt.   | impurities such as other metals, metal salts and non metals, | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A further preferred embodiment of the invention relates to stents consisting of a biologically degradable magnesium alloy comprising or consisting of the following components:

| 80.55% by wt. - | 99.5% by wt.  | magnesium |
| 0.1% by wt. -   | 11.0% by wt.  | dysprosium |
| 0.1% by wt. -   | 3.2% by wt.   | neodymium |
| 0.1% by wt. -   | 2.0% by wt.   | zinc |
| 0.1% by wt. -   | 0.75% by wt.  | zirconium |
| 0.1% by wt. -   | 2.5% by wt.   | impurities such as other metals, metal salts and non metals, | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A further preferred embodiment of the invention relates to stents consisting of a biologically degradable magnesium alloy comprising or consisting of the following components:

| 80.25% by wt. - | 94.6% by wt.  | magnesium |
| 5.0% by wt. -   | 12.5% by wt.  | dysprosium |
| 0.1% by wt. -   | 2.0% by wt.   | europium |
| 0.1% by wt. -   | 2.0% by wt.   | zinc |
| 0.1% by wt. -   | 0.75% by wt.  | zirconium |
| 0.1% by wt. -   | 2.5% by wt.   | impurities such as other metals, metal salts and non metals, | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A further preferred embodiment of the invention relates to stents consisting of a biologically degradable magnesium alloy comprising or consisting of the following components:

| 80.0% by wt. - | 99.4% by wt.  | magnesium |
| 0.1% by wt. -  | 11.0% by wt.  | dysprosium |
| 0.1% by wt. -  | 2.0% by wt.   | europium |
| 0.1% by wt. -  | 3.0% by wt.   | neodymium |
| 0.1% by wt. -  | 2.0% by wt.   | zinc |
| 0.1% by wt. -  | 1.0% by wt.   | zirconium |
| 0.1% by wt. -  | 1.0% by wt.   | impurities such as other metals, metal salts and non metals, | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A further preferred embodiment of the invention relates to stents consisting of a biologically degradable magnesium alloy comprising or consisting of the following components:

| 80.0% by wt. -  | 99.65% by wt. | magnesium |
| 0.1% by wt. -   | 15.0% by wt.  | dysprosium |
| 0.1% by wt. -   | 3.0% by wt.   | europium |
| 0.05% by wt. -  | 2.0% by wt.   | zirconium | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A further preferred embodiment of the invention relates to stents consisting of a biologically degradable magnesium alloy comprising or consisting of the following components:

| 88% by wt.  | magnesium |
| 10% by wt.  | dysprosium |
| 1% by wt.   | europium |
| 1% by wt.   | zirconium | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A further preferred embodiment of the invention relates to stents consisting of a biologically degradable magnesium alloy comprising or consisting of the following components:

| 80.0% by wt. -  | 94.75% by wt. | magnesium |
| 0.1% by wt. -   | 15.0% by wt.  | dysprosium |
| 0.2% by wt. -   | 4.0% by wt.   | europium |
| 0.05% by wt. -  | 4.0% by wt.   | zinc | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A further preferred embodiment of the invention relates to stents consisting of a biologically degradable magnesium alloy comprising or consisting of the following components:

| 88% by wt.  | magnesium |
| 10% by wt.  | dysprosium |
| 1% by wt.   | europium |
| 1% by wt.   | zinc | wherein the stent has an inorganic coating comprising or consisting of at least one inorganic compound, wherein the at least one inorganic compound contains fluoride ions and preferable magnesium fluoride.

A further preferred embodiment of the invention relates to stents consisting of a biologically degradable magnesium alloy comprising or consisting of the following components:

| 80.0% by wt. -  | 99.6% by wt.  | magnesium |
| 0.1% by wt. -   | 14.0% by wt.  | dysprosium |
| 0.2% by wt. -   | 2.0% by wt.   | europium |

| | | |
|---|---|---|
| 0.05% by wt. - | 2.0% by wt. | zinc |
| 0.05% by wt. - | 2.0% by wt. | zirconium | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A further preferred embodiment of the invention relates to stents consisting of a biologically degradable magnesium alloy comprising or consisting of the following components:

| | |
|---|---|
| 87% by wt. | magnesium |
| 10% by wt. | dysprosium |
| 1% by wt. | europium |
| 1% by wt. | zinc |
| 1% by wt. | zirconium | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A particularly preferred embodiment of the invention relates to stents consisting of a biologically degradable magnesium alloy, comprising or consisting of the following components:

| | |
|---|---|
| 87.8% by wt. | magnesium |
| 10% by wt. | dysprosium |
| 1% by wt. | europium |
| 1% by wt. | zinc |
| 0.2% by wt. | zirconium | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A further preferred embodiment of the invention relates to stents consisting of a biologically degradable magnesium alloy comprising or consisting of the following components:

| | |
|---|---|
| 86.8% by wt. | magnesium |
| 10% by wt. | dysprosium |
| 1% by wt. | europium |
| 1% by wt. | zinc |
| 0.2% by wt. | zirconium | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A further particularly preferred embodiment of the invention relates to stents consisting of a biologically degradable magnesium alloy comprising or consisting of the following components:

| | |
|---|---|
| 87.8% by wt. | magnesium |
| 10% by wt. | dysprosium |
| 1% by wt. | neodymium |
| 1% by wt. | europium |
| 1% by wt. | zinc |
| 0.2% by wt. | zirconium | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

Consequently, a further preferred embodiment of the invention relates to stents consisting of a biologically degradable magnesium alloy, comprising or consisting of the following components:

| | | |
|---|---|---|
| 93.0% by wt. - | 94.0% by wt. | magnesium |
| 0.3% by wt. - | 0.4% by wt. | dysprosium |
| 2.0% by wt. - | 2.1% by wt. | neodymium |
| 0.3% by wt. - | 0.5% by wt. | gadolinium |
| 0.3% by wt. - | 0.4% by wt. | zirconium |
| 3.4% by wt. - | 3.8% by wt. | yttrium |
| 0.0% by wt. - | 0.02% by wt. | erbium | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A further preferred embodiment of the invention relates to stents consisting of a biologically degradable magnesium alloy comprising or consisting of the following components:

| | | |
|---|---|---|
| 92.0% by wt. - | 93.0% by wt. | magnesium |
| 0.9% by wt. - | 1.1% by wt. | dysprosium and gadolinium together |
| 2.1% by wt. - | 2.3% by wt. | neodymium |
| 0.4% by wt. - | 0.6% by wt. | zirconium |
| 3.9% by wt. - | 4.3% by wt. | yttrium | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A further preferred embodiment of the invention relates to stents consisting of a biologically degradable magnesium alloy comprising or consisting of the following components:

| | | |
|---|---|---|
| 91.0% by wt. - | 92.0% by wt. | magnesium |
| 0.7% by wt. - | 0.8% by wt. | dysprosium |
| 0.6% by wt. - | 0.8% by wt. | gadolinium |
| 1.9% by wt. - | 2.1% by wt. | neodymium |
| 0.6% by wt. - | 0.8% by wt. | zirconium |
| 3.9% by wt. - | 4.2% by wt. | yttrium | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

Moreover, a further preferred embodiment of the invention relates to stents consisting of a biologically degradable magnesium alloy comprising or consisting of the following components:

| | | |
|---|---|---|
| 91.0% by wt. - | 92.0% by wt. | magnesium |
| 0.7% by wt. - | 0.8% by wt. | dysprosium |
| 0.6 % by wt. - | 0.8% by wt. | gadolinium |
| 1.9% by wt. - | 2.1% by wt. | neodymium |
| 0.6% by wt. - | 0.8% by wt. | zirconium |
| 3.9% by wt. - | 4.2% by wt. | yttrium | wherein the stent contains a magnesium fluoride coating and an organic coating of poly(L-lactide) (PLLA).

A further preferred embodiment of the invention relates to stents consisting of a biologically degradable yttrium free magnesium alloy comprising or consisting of the following components:

| | | |
|---|---|---|
| 93.7% by wt. - | 96.2% by wt. | magnesium |
| 1.0% by wt. - | 1.5% by wt. | gadolinium |
| 2.0% by wt. - | 3.1% by wt. | neodymium |
| 0.5% by wt. - | 0.7% by wt. | zirconium |
| 0.1% by wt. - | 0.5% by wt. | calcium |
| 0.2% by wt. - | 0.5% by wt. | zinc | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A further preferred embodiment of the invention relates to stents consisting of a biologically degradable magnesium alloy comprising or consisting of the following components:

| | |
|---|---|
| 96.9% by wt. | magnesium |
| 2.5% by wt. | neodymium |
| 0.4% by wt. | zirconium |
| 0.2% by wt. | zinc | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A further preferred embodiment of the invention relates to stents consisting of a biologically degradable magnesium alloy comprising or consisting of the following components:

| | |
|---|---|
| 97.45% by wt. | magnesium |
| 0.75% by wt. | neodymium |
| 1.80% by wt. | manganese | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A further preferred embodiment of the invention relates to stents consisting of a biologically degradable magnesium alloy comprising or consisting of the following components:

| | |
|---|---|
| 97.45% by wt. | magnesium |
| 0.75% by wt. | cerium |
| 1.80% by wt. | manganese | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A further preferred embodiment of the invention relates to stents consisting of a biologically degradable magnesium alloy, comprising or consisting of the following components:

| | |
|---|---|
| 90.0% by wt. | magnesium |
| 3.0% by wt. | gadolinium |
| 2.4% by wt. | yttrium |
| 0.4% by wt. | zirconium |
| 4.2% by wt. | scandium | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A further preferred embodiment of the invention relates to stents consisting of a biologically degradable magnesium alloy, comprising or consisting of the following components:

| | |
|---|---|
| 90.0% by wt. | magnesium |
| 3.0% by wt. | neodymium |
| 2.4% by wt. | yttrium |
| 0.4% by wt. | zirconium |
| 5.2% by wt. | scandium |
| 2.0% by wt. | indium | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

A further preferred embodiment of the invention relates to stents consisting of a biologically degradable magnesium alloy, comprising or consisting of the following components:

| | |
|---|---|
| 96.0% by wt. | magnesium |
| 4.0% by wt. | lithium | wherein the stent contains a magnesium fluoride coating and an organic coating comprising one or more substances of the following group: poly-ε-caprolactone (PCL), poly(L-lactide-co-glycolide) (PLGA), poly(L-lactide) and parylene.

As organic coating the polymers poly-ε-caprolactone (PCL), poly(L-lactide-co-glycolide) (PLGA), poly(L-lactide) and parylene are preferred, whereby the following polymers provided comparable results in preliminary tests: polyvinyl pyrrolidone, polyhydroxyethyl methacrylates, polyhydroxybutyrate, polyvalerolactones, poly-ε-decalactones, poly(D,L-lactide-co-glycolide), polyglycolides, copolymers of polylactides and polyglycolides, polyhydroxyvalerates, polyhydroxy methacrylates, polycaprolactone dimethylacrylates, polycaprolactone butyl acrylates, polycaprolactone glycolides, polyurethanes, polymethyl methacrylate, polyvinyl ketones, polyvinyl ethers, polyvinyl aromatic compounds, polyvinyl esters, polyethylene terephthalate, polyvalerates, and polysulfones.

The present invention relates to stents of a biologically degradable magnesium alloy, as disclosed herein, having at least 80% by wt. magnesium, an inorganic coating comprising or consisting of magnesium fluoride and an organic coating.

The inorganic coating may comprise further inorganic as well as organic materials in addition to magnesium fluoride. Inorganic materials traditionally include the elements and all compounds that do not contain carbon. Additionally there are several exceptions of carbon compounds, which are structured exactly like typical inorganic materials or are historically allocated to the field of inorganic chemistry. These include the hydrogen-free chalcogenides of carbon, carbonic acid and carbonates, carbides as well as ionic cyanides, cyanates and thiocyanates. An inorganic coating as used herein refers to a layer applied on the struts of a stent, wherein the layer consists of magnesium fluoride and one of these inorganic compounds, mixtures thereof or contains at least magnesium fluoride as main component, i.e. at least 50%, preferably at least 80% and even more preferably at least 90%. A layer of an antirestenotic active agent or an organic layer of one or more organic compounds, preferably organic polymers, may be applied to the inorganic layer, wherein this organic layer may contain the antirestenotic active agent as well, so that no third active agent layer has to be applied. Thus, the layer of one or more organic compounds may contain one or more antirestenotic active agent(s) or the antirestenotic active agent may be applied to the layer of one or more organic compounds, wherein the in this case middle organic layer may contain no, the same or another or more than one antirestenotic active agents.

It may be advantageous that the abluminal coating (facing the vessel wall) dissolves more slowly than the luminal stent coating (facing the vessel lumen). In addition, a stent is preferred which only has micropores, holes, openings or channels in the luminal, inorganic, biologically degradable coating and the overlying luminal, organic coating. Hydrogen gas is formed during degradation of magnesium alloys. This is one reason why it is preferred that the lumen and blood flow side of the inorganic biodegradable coating and the organic coating contain micropores, holes, openings, channels or other structures that allow the outflow of gas, but the abluminal side of the coating not as in this case the gas is washed away and distributed with the blood flow and cannot accumulate between the stent and the vessel wall.

If not generated by the coating process itself, these micropores, holes, openings and/or channels may be mechanically, chemically, thermally or optically introduced in the inorganic coating after it has been applied to the stent. Furthermore micropores, holes, opening and/or channels may be mechanically, chemically, thermally or optically introduced in the organic coating applied to the inorganic coating. For example, this may done by mechanical treatment such as sandblasting, by chemical processes such as etching, by mechano-chemical processes such as polishing, by thermal processes such as melting or baking, or by optical processes such as laser treatment.

According to the invention, it is preferred that the inorganic coating and the organic coating are designed in such a way that the inner metallic scaffold can dissolve in the coating and that both hydrogen gas and the metal ions are mainly released into the blood on the luminal side of the coating, but not directly leaking into the surrounding tissue.

However, a stent of one of the herein described biodegradable magnesium alloys having at least 80% by weight magnesium is particularly preferred, wherein the inorganic coating and/or the organic coating have no micropores, holes, openings or channels. This applies in particular to inorganic or organic coatings without active agent. It is also preferred that a stent of one of the herein described biodegradable magnesium alloys having at least 80% by weight magnesium has an organic coating without micropores, holes, openings or channels.

It is preferred that the inner basic scaffold of the biologically degradable magnesium alloy is degraded under physiological condition before the inorganic coating and the outer organic coating are degraded, so that after degradation of the inner basic scaffold an empty shell, ingrown in the vessel wall, remains, which however is flexible and does not longer exerts any significant pressure on the vessel wall and even adapts well to the new course of the vessel. After complete dissolution of the inner metallic basic scaffold, the inorganic coating and the organic coating may also be degraded biologically, so that the stent is fully dissolved after several months. Thereby, the degradation of the inorganic coating and the organic coating should be uniform and without the risk of detaching fragments.

In general, the inorganic coating and the organic coating serve for the regulation of the rate of degradation of the metallic stent scaffold. The duration until dissolution of the basic scaffold may be affected by the choice of compounds or the mixture of compounds, which form the inorganic coating or the organic coating. Furthermore, the inorganic coating and the organic coating may serve as a protecting shell against fragments of the basic scaffold and the surface of the stent can be designed in a more biocompatible or hemocompatible manner respectively. This means that the inorganic coating and the organic coating of a stent according to the invention improve blood compatibility. This may be due to a better and uniform colonization of the surface with cells, particularly smooth muscle cells and preferably enthothelial cells. Blood clotting may also be triggered to a lesser extent by the stent surface due to the inorganic coating and the organic coating which may lead to a reduction of the risk of thrombosis.

In further embodiments, at least one antiinflammatory, antiproliferative, antiangiogenic, antirestenotic (anti-restenosis), antineoplastic, antimigrative and/or antithrombogenic active agent is present in or on the inorganic coating and below the organic coating. This active agent may be contained in covalently bound form or in adhesive or ionically bound form in the inorganic coating or be applied as additional layer. Coated endoprothesis as well as stents are thereby obtained, which have at least one active agent in the inorganic coating or which have an additional layer containing the active agent on the inorganic coating. Preferably, the at least one antiinflammatory, antiproliferative, antiangiogenic, antirestenotic, antineoplastic, antimigrative and/or antithrombogenic active agent is applied in the form of an additional active agent releasing layer (drug release system) to the surface of the inorganic coating of the stent.

In further preferred embodiments, at least one antirestenotic active agent such as an antiinflammatory, antiproliferative, antiangiogenic, antirestenotic, antineoplastic, antimigrative and/or antithrombogenic active agent is present in or on the outer polymeric organic coating. Suitable antirestenotic active agents were already explicitly mentioned above. Preferred are derivates of sirolimus ("limus" derivatives) as well as paclitaxel. Particularly preferred is sirolimus itself. The active agent can be contained in covalently bound form or in adhesive or ionically bound form in the polymeric organic coating or applied as additional layer. Coated endoprothesis as well as stents are thereby obtained, which have at least one active agent in the polymeric coating or which have an additional layer containing the active agent on the polymeric coating. Preferably, the at least one antiinflammatory, antiproliferative, antiangiogenic, antirestenotic, antineoplastic, antimigrative and/or antithrombogenic active agent is applied in form of an additional active agent releasing layer (drug release system) to the surface of the polymeric organic coating of the stent. This active agent releasing layer may be a pure active agent layer or a carrier layer of the aforementioned carrier materials or matrix materials or as well of a futher polymer.

The at least one used antiinflammatory, antiproliferative, antiangiogenic, antirestenotic, antineoplastic, antimigrative and/or antithrombogenic active agent is preferably selected from the group comprising or consisting of: abciximab, acemetacin, acetylvismione B, aclarubicin, ademetionine, adriamycin, aescin, afromosone, akagerine, aldesleukin, amidorone, aminoglutethimide, amsacrine, anakinra, anastrozole, anemonin, anopterine, antimycotics, antithrombotics, apocymarin, argatroban, aristolactam-AII, aristolochic acid, ascomycin, asparaginase, aspirin, atorvastatin, auranofin, azathioprine, azithromycin, baccatin, bafilomycin, basiliximab, bendamustine, benzocaine, berberine, betulin, betulinic acid, bilobol, bisparthenolidine, bleomycin, bombrestatin, boswellic acids and its derivatives, bruceanol A, B and C, bryophyllin A, busulfan, antithrombin, bivalirudin, cadherins, camptothecin, capecitabine, o-carbamoyl-phenoxyacetic acid, carboplatin, carmustine, celecoxib, cepharanthin, cerivastatin, CETP inhibitors, chlorambucil, chloroquine phosphate, cicutoxin, ciprofloxacin, cisplatin, cladri bine, clarithromycin, colchicine, concanamycin, coumadin, C-type natriuretic peptide (CNP), cudraisoflavone A, curcumin, cyclophosphamide, ciclosporin A, cytarabine, dacarbazine, daclizumab, dactinomycin, dapsone, daunorubicin, diclofenac, 1,11-dimethoxycanthin-6-one, docetaxel, doxorubicin, dunaimycin, epirubicin, epothilone A and B, erythromycin, estramustine, etoboside, everolimus, filgrastim, fluroblastin, fluvastatin, fludarabine, fludarabine-5'-dihydrogen phosphate, fluorouracil, folimycin, fosfestrol, gemcitabine, ghalakinoside, ginkgol, ginkgolic acid, glycoside 1a, 4-hydroxyoxycyclophosphamide, idarubicin, ifosfamide, josamycin, lapachol, lomustine, lovastatin, melphalan, midecamycin, mitoxantrone, nimustine, pitavastatin, pravastatin, procarbazine, mitomycin, methotrexate, mercaptopurine, thioguanine, oxaliplatin, irinotecan, topotecan, hydroxycarbamide, miltefosine, pentostatin, pegaspargase, exemestane, letrozole, formestane, mitoxanthrone, mycophenolate mofetil, β-lapachone, podophyllotoxin, podophyllic acid 2-ethyl hydrazide, molgramostim (rhuGM-CSF), peginterferon α-2b, lanograstim (r-HuG-CSF), macrogol, selectin (cytokine antagonist), cytokinin inhibitors, COX-2 inhibitor, angiopeptine, monoclonal antibodies inhibiting muscle cell proliferation, bFGF antagonists, probucol, prostaglandins, 1-hydroxy-11-methoxycanthin-6-one, scopolectin, NO donors, pentaerythritol tetranitrate and sydnonimines, S-nitroso derivatives, tamoxifen, staurosporine, ß-estradiol, α-estradiol, estriol, estrone, ethinyl estradiol, medroxyprogesterone, estradiol cypionates, estradiol benzoates, tranilast, kamebakaurin and other terpenoids used in cancer therapy, verapamil, tyrosine kinase inhibitors (tyrphostins), paclitaxel and its derivatives, 6-α-hydroxy-paclitaxel, taxoteres, mofebutazone, lonazolac, lidocaine, ketoprofen, mefenamic acid, piroxicam, meloxicam, penicillamine, hydroxychloroquine, sodium aurothiomalate, oxaceprol, β-sitosterol, myrtecaine, polidocanol, nonivamide, levomenthol, ellipticine, D-24851 (Calbiochem), colcemid, cytochalasin A-E, indanocine, nocodazole, bacitracin, vitronectin receptor antagonists, azelastine, guanidyl cyclase stimulator tissue inhibitor of metal proteinase-1 and -2, free nucleic acids, nucleic acids incorporated into virus transmitters, DNA and RNA fragments, plasminogen activator inhibitor 1, plasminogen activator inhibitor 2, antisense oligonucleotides, VEGF inhibitors, IGF 1, active agents from the group of antibiotics, cefadroxil, cefazolin, cefaclor, cefoxitin, tobramycin, gentamicin, penicillins, dicloxacillin, oxacillin, sulfonamides, metronidazole, enoxaparin, heparin, hirudin, PPACK, protamine, prourokinase, streptokinase, warfarin, urokinase, vasodilators, dipyramidole, trapidil, nitroprussides, PDGF antagonists, triazolopyrimidine, seramin, ACE inhibitors, captopril, cilazapril, lisinopril, enalapril, losartan, thioprotease inhibitors, prostacyclin, vapiprost, interferon α, β and γ, histamine antagonists, serotonin blockers, apoptosis inhibitors, apoptosis regulators, halofuginone, nifedipine, paracetamol, dexpanthenol, clopidogrel, acetylsalicylic acid derivatives, streptomycin, neomycin, framycetin, paromomycin, ribostamycin, kanamycin, amikacin, arbekacin, bekanamycin, dibekacin, spectinomycin, hygromycin b, paromomycinsulfate, netilmicin, sisomicin, isepamicin, verdamicin, astromicin, apramycin, geneticin, amoxicillin, ampicillin, bacampicillin, pivmecillinam, flucloxacillin, mezlocillin, piperacillin, azlocillin, temocillin, ticarcillin, amoxicillin, clavulanic add, ampicillin, sulbactam, piperacillin, tazobactam, sulbactam, cefamandol, cefotiam, cefuroxim, cefmenoxim, cefodizim, cefoperazon, cefotaxim, ceftazidim, cefsulodin, ceftriaxon, cefepim, cefpirom, cefoxitin, cefotetan, cefalexin, cefuroxim axetil, cefixim, cefpodoxim, ceftibuten, imipenem, meropenem, ertapenem, doripenem, aztreonam, spiramycin, azithromycin, telithromycin, quinopristin, dalfopristin, clindamycin, tetracycline, doxycyclin, minocyclin, trimethoprim, sulfamethoxazol, sulfametrol, nitrofurantoin, lomefloxacin, norfloxacin, ciprofloxacin, ofloxacin, fleroxacin, levofloxacin, sparfloxacin, moxifloxacin, vancomycin, teicoplanin, linezolid, daptomycin, rifampicin, fusidic acid, fosfomycin, trometamol, chloramphenicol, metronidazol, colistin, mupirocin, bacitracin, neomycin, fluconazol, itraconazol, voriconazol, posaconazol, amphotericin B, 5-flucytosin, caspofungin, anidulafungin, tocopherol, tranilast, molsidomine, tea polyphenols, epicatechin gallate, epigallocatechin gallate, leflunomide, etanercept, sulfasalazine, etoposide, dicloxaclline, tetracycline, triamcinolone, mutamycin, procainimide, retinoic acid, quinidine, disopyrimide, flecainide, propafenone, sotolol, natural and synthetically produced steroids, inotodiol, maquiroside A, ghalakinoside, mansonine, strebloside, hydrocortisone, betamethasone, dexamethasone, non-steroidal substances (NSAIDS), fenoprofen, ibuprofen, indomethacin, naproxen, phenylbutazone, antiviral agents, acyclovir, ganciclovir, zidovudine, clotrimazole, flucytosine, griseofulvin, ketoconazole, miconazole, nystatin, terbinafine, antiprozoal agents, chloroquine, mefloquine, quinine, natural terpenoids, hippocaesculin, barringtogenol-C21-angelate, 14-dehydroagrostistachin, agroskerin, agrostistachin, 17-hydroxyagrostistachin, ovatodiolids, 4,7-oxycycloanisomelic acid, baccharinoids B1, B2, B3 and B7, tubeimoside, bruceantinoside C, yadanziosides N and P, isodeoxyelephantopin, tomenphantopin A and B, coronarin A, B C and D, ursolic acid, hyptatic acid A, iso-iridogermanal, maytenfoliol, effusantin A, excisanin A and B, longikaurin B, sculponeatin C, kamebaunin, leukamenin A and B, 13,18-dehydro-6-alpha-senecioyloxychaparrin, taxamairin A and B, regenilol, triptolide, cymarin, hydroxyanopterine, protoanemonin, cheliburin chloride, sinococuline A and B, dihydronitidine, nitidine chloride, 12-beta-hydroxypregnadien-3,20-dione, helenalin, indicine, indicine-N-oxide, lasiocarpine, inotodiol, podophyllotoxin, justicidin A and B, larreatin, malloterin, mallotochromanol, isobutyrylmallotochromanol, maquiroside A, marchantin A, maytansin, lycoridicin, margetine, pancratistatin, liriodenine, bisparthenolidine, oxoushinsunine, periplocoside A, ursolic acid, deoxypsorospermin, psychorubin, ricin A, sanguinarine, manwu wheat acid, methylsorbifolin, chromones of spathelia, stizophyllin, mansonine, strebloside, dihydrousambaraensine, hydroxyusambarine, strychnopentamine, strychnophylline, usambarine, usambarensine, liriodenine, oxoushinsunine, daphnoretin, lariciresinol, methoxylariciresinol, syringaresinol, sirolimus (rapamycin) and its derivatives such as biolimus A9, everolimus, myolimus, novolimus, pimecrolimus, ridaforolimus, deoxorapamycin, tacrolimus FK 506, temsirolimus and zotarolimus, somatostatin, tacrolimus, roxithromycin, troleandomycin, simvastatin, rosuvastatin, vinblastine, vincristine, vindesine, teniposide, vinorelbine, trofosfamide, treosulfan, tremozolomide, thiotepa, tretinoin, spiramycin, umbelliferone, desacetylvismione A, vismione A and B, zeorin, and sulfur-containing amino acids such as cystine as well as salts, hydrates, solvates, enantiomers, racemates, mixtures of enantiomers, mixtures of diastereomers, metabolites, prodrugs and mixtures of the aforementioned active agents. The concentration per active agent is preferably in the range of 0.001-500 mg per $cm^2$ coated surface of the endoprosthesis. Especially preferred active agents according to the present invention are paclitaxel, rapamycin and their derivatives, such as 6-α-hydroxy-paclitaxel, baccatin or other taxoteres, biolimus A9, myolimus, novolimus, pimecrolimus, tacroliums, temsirolimus, zotarolimus, everolimus, ridaforolimus or further "limus"-derivatives, erythromycin, midecamycin, josamycin and triazolopyrimidines. Particularly preferred is sirolimus (rapamycin). Also preferred are paclitaxel and the "limus" derivatives biolimus A9, myolimus, novolimus, pimecrolimus, tacroliums, temsirolimus, zotarolimus, everolimus, ridaforolimus or further sirolimus derivatives. All of the aforementioned compounds are herein referred to as antirestenotic active agents for simplicity reasons.

According to a preferred embodiment, the stent has an inorganic coating covered by an organic coating containing at least one antiproliferative, antiphlogistic and/or antithrombigenic active agent.

In a particular preferred embodiment, the stent coating consists of a first inorganic coating comprising or consisting of magnesium fluoride covered by a second organic coating containing at least one antirestenotic active agent such as an antiproliferative, antiphlogistic and/or antithrombogenic active agent.

Between the inorganic coating and the organic coating containing the active agent, an additional adhesion-promoting layer may also be applied. Alternatively, a compound to support adhesion may be contained in the organic coating containing the active agent.

Thus, a preferred embodiment of the invention is a stent consisting of a basic scaffold of one of the herein disclosed biodegradable magnesium alloys having at least 80% by wt. magnesium, an inorganic coating comprising magnesium fluoride and an organic coating, optionally having at least one active agent.

Furthermore, it is preferred that the organic coating preferably consists of an organic polymer such as a parylene and contains an antirestenotic active agent and/or a third coating of the antirestenotic active agent present on this organic coating.

It is also possible that the active agent is applied to the stent after the inorganic coating has already been applied and before the organic coating is applied to the metallic basic scaffold and the active agent does not form an own layer, but rather penetrates into the already present inorganic coating. Then, it is preferred that the active agent is not penetrating the entire coating, but rather remains in the outer part and forms a concentration gradient, which decreases in direction to the basic scaffold.

The inorganic layer or coating of the stent itself preferably contains a maximum of 10% polymers and is even more preferably polymer-free. A layer of at least one antirestenotic active agent or an organic coating, for example of a polymer or a carrier substance or a matrix substance, with or without at least one antirestenotic active agent may be optionally present on the preferably polymer-free inorganic coating. Suitable carrier or matrices are described herein.

However, if the at least one active agent or combination of active agents is applied to the inorganic coating of stents, further substances may be applied as pharmacologically acceptable carriers or as matrix in combination with the at least one active agent or the combination of active agents. These carrier or matrices are also referred to as organic coatings or organic layers.

Polymers as wells as low molecular substances may serve as pharmacologically acceptable carriers, such as for example lactose, starch, sodium carboxymethyl starch, sorbitol, sucrose, magnesium stearate, dicalcium phosphate, calcium sulfate, talcum, mannitol, ethyl alcohol, polyvinyl alcohols, polyvinyl pyrrolidone, gelatine, naturally occurring sugars, naturally occurring as well as synthetic gums such as acacia gum or guar gum, sodium alginate, sodium benzoate, sodium acetate, glycerides, isopropyl myristates and palmitates, citrates, such as tributyl and triethyl citrates and their acetyl derivatives, phthalates such as dimethyl phthalate or dibutyl phthalate, etc. benzoic acid benzyl ester, triacetine, 2-pyrrolidone, boric acid, magnesium aluminium silicates, naturally occurring carob gum, gum karaya, guar, tragacanth, agar, cellulose, cellulose derivatives such as methyl cellulose, sodium carboxymethyl cellulose, hydroxypropyl methyl cellulose, microcrystalline cellulose as well as alginates, PLLA, parylene, polysulfones, shellac, aluminas and bentonites, polyethylene glycol and also waxes such as for example beeswax, carnauba wax, candelilla wax and the like can be used. The matrix substance of the second layer can also be identical to one inorganic compound of the first layer or to the entire composition of the first layer. The additional carrier or matrix substances can be used in a weight ratio of up to 70% by wt., preferably to 50% by wt. based on the used active agent(s).

A preferred embodiment is a stent of one of the herein disclosed magnesium alloys having at least 80% by wt. magnesium, an inorganic coating comprising magnesium fluoride and on the inorganic coating an organic coating of a parylene. Furthermore, it is preferred that the organic coating contains an antirestenotic active agent and/or that an antirestenotic agent is applied thereto, such as preferably paclitaxel, sirolimus, biolimus A9, myolimus, novolimus, pimecrolimus, tacrolimus, temsirolimus, zotarolimus, everolimus, redaforolimus, or another sirolimus derivate and particularly preferred sirolimus (rapamycin).

A preferred embodiment of the invention relates to stents consisting of a biologically degradable magnesium alloy, comprising or consisting of the following components:

| | | |
|---|---|---|
| 91.0% by wt. - | 92.0% by wt. | magnesium |
| 0.7% by wt. - | 0.8% by wt. | dysprosium |
| 0.6% by wt. - | 0.8% by wt. | gadolinium |
| 1.9% by wt. - | 2.1% by wt. | neodymium |
| 0.6% by wt. - | 0.8% by wt. | zirconium |
| 3.9% by wt. - | 4.2% by wt. | yttrium | wherein the stent contains a magnesium fluoride coating and an organic coating of poly(L-lactide) (PLLA) wherein at least one antiinflammatory, antiproliferative, antiangiogenic, antirestenotic, antineoplastic, antimigrative and/or antithrombogenic active agent is present therein or thereon.

A further preferred embodiment of the invention relates to stents consisting of a biologically degradable magnesium alloy, comprising or consisting of the following components:

| | | |
|---|---|---|
| 91.0% by wt. - | 92.0% by wt. | magnesium |
| 0.7% by wt. - | 0.8% by wt. | dysprosium |
| 0.6% by wt. - | 0.8% by wt. | gadolinium |
| 1.9% by wt. - | 2.1% by wt. | neodymium |
| 0.6% by wt. - | 0.8% by wt. | zirconium |
| 3.9% by wt. - | 4.2% by wt. | yttrium | wherein the stent contains a magnesium fluoride coating and an organic coating of poly(L-lactide) (PLLA), and the organic coating additionally contains the active agent sirolimus and/or it is present thereon.

The organic coating can generally be applied to the inorganic coating already present on the magnesium alloy of the basic scaffold, by means of known methods such as spraying, dipping, plasma, brushing, syringe or pipetting method. Therefore the stent according to the invention can be coated by spraying, pipetting, brushing, spraying, plasma or dipping, whereby the organic compound or mixtures of the compounds are dissolved in a solvent and this solution is applied to the implant. The solvent or solvent mixture is then removed by evaporation at room temperature or heating.

The coating of the stents according to the invention can be carried out both before and after crimping onto a catheter balloon. If the coating is at first applied after the stent has been attached to a catheter balloon, a dipping or spraying method is preferred.

The organic coating should be performed relatively uniformly. The organic coating can have a thickness of about 0.01 to 100 μm and preferably of 0.1-50 μm, further preferably of 0.2-20 μm and most preferably of 0.5-10 μm.

In case of parylene as an organic coating, the layer thickness may be lower and is in the range from 0.001 to 10 μm, preferably in the range from 0.01 to 5 μm and further preferably in the range from 0.05 to 1.0 μm.

Furthermore, it is preferred that the ratio of the layer thickness of the inorganic coating and the organic coating of the stents according to the invention is 500:1 to 1:1,000,000, more preferably 400:1 to 1:700,000, even more preferably 100:1 to 1:200,000 and most preferably 20:1 to 1:100,000.

It is also preferred that the ratio of the layer thickness of the inorganic coating and the organic coating of the stents according to the invention is 1:500,000 to 1:1,000, more preferably 1:100,000 to 1:5,000, even more preferably 1:50,000 to 1:10,000 (inorganic:organic).

The inorganic coating can generally be applied to the magnesium alloy of the basic scaffold by means of known methods such as spraying, dipping, plasma, brushing, syringe or pipetting method. The stent according to the invention can be coated by spraying, pipetting, brushing, injection, plasma or dipping, whereby the inorganic compound or the inorganic material or mixtures of the compounds are dissolved in a solvent and this solution is applied to the implant. The solvent or solvent mixture is then removed by evaporation at room temperature or heating.

The coating of the stents according to the invention can be carried out both before and after crimping onto a catheter balloon. If the coating is at first applied after the stent has been attached to a catheter balloon, a dipping or spraying method is preferred.

Various methods known in the art can be used to apply an inorganic coating to a stent. For example, suspensions of inorganic particles in water or organic solvents such as ethanol can be used to produce the inorganic coatings.

According to an aspect of the present disclosure, the application and drying of the inorganic coating may be repeated several times to form a multi-layer coating. Likewise, the application and drying of the organic coating can be repeated several times to form a multi-layer coating. Application in several layers facilitates the formation of the inorganic coating or organic coating with the desired thickness (e.g. in the order of μm). More active agent can be embedded in a thicker coating.

Ion implantation can also be used for inorganic coating of surface areas/edge areas of the stent according to the invention. Ion implantation is a method of introducing foreign atoms in the form of ions into the base material by bombarding the alloy with accelerated ions in a high vacuum. The ions are initially generated by means of an ion source, extracted by an electric field and then separated by a mass separator according to their mass. The ions are then accelerated and directed onto the alloy with an electric field. The ions are implanted into the alloy. Among the most important parameters of ion implantation are the acceleration energy with which the ions are accelerated, the ion type and the implantation dose. The first two parameters determine the penetration depth of the ions into the alloy and the implantation dose determines the concentration of the implanted ions. With ion implantation, different ions may be incorporated into the alloy, e.g. fluoride ions, oxygen ions, carbon ions. Implantation can cause damage to the crystal lattice of the alloy depending on the mass of the implanted ions and the implantation dose. In such cases, the alloy needs to be subjected to a high-temperature process after an implantation step in which the foreign atoms are incorporated into the lattice. This process is also referred to as healing. The healing process can, for example, be accomplished by a furnace process.

During the chemical transformation to the inorganic coating of the stents according to the invention, the surface of the magnesium alloy is transformed by a chemical reaction into the desired magnesium fluoride coating in the presence of a fluoride-containing aqueous solution. Depending on the composition of the initial alloy, the coating may contain dysprosium, europium, neodymium, zinc, zirconium, yttrium, erbium, gadolinium and calcium. Furthermore, the coatings may include Si, Ni, Fe, Cu as well as other metals and non-metals due to unavoidable impurities of the magnesium alloy used. Preferred reaction media are hydrofluoric acid, aqueous potassium fluoride solution and aqueous ammonium fluoride solution.

Electrochemical plasma oxidation and the sol-gel process are also suitable methods to produce an inorganic coating according to the invention. In plasma oxidation, oxide layers of up to 10 μm thickness are produced by applying voltages of up to several 100 V in aqueous electrolytes on the surface of the stent.

Sol-gel processes involve the formation of a colloidal suspension of so-called precursors. The starting materials for sol synthesis are often alcoholates of metals or non-metals. After the colloidal suspension has been formed, water, an acid, a base or a combination thereof is added to initiate hydrolysis and condensation. The hydrolysis of precursor molecules and the condensation between the resulting reactive species are the essential basic reactions of the sol-gel process. The processes involved and the properties of the precursor molecules have a decisive effect on the resulting material properties. After the coating has been applied to at least a part of the stent, the coating composition is heated, which is necessary for aging and removal of organic solvents.

The inorganic coating should be performed relatively uniformly. The inorganic coating can have a thickness of about 0.1 pm to 10 µm and preferably a thickness of 1 pm to about 100 nm, further preferred from 10 pm to about 1 nm. The desired layer thickness also depends on the respective inorganic compound, which may be contained in the inorganic coating in addition to magnesium fluoride, and can be achieved by repeated coating steps interrupted by drying steps. In particular, if the inorganic coating is deposited from a gas phase, the coating becomes impermeable over a longer period of time. In case of short coating times, leaks occur which permit the diffusion of water or gases.

In a suitable solvent, possibly also together with the inorganic compound, the at least one antiinflammatory, antiproliferative, antiangiogenic, antirestenotic (anti-restenosis), antineoplastic, antimigrative and/or antithrombogenic active agent to be applied can be dissolved, emulsified, suspended or dispersed. If a matrix or carrier substance is contained in the active agent layer, it can be dissolved and applied together with the active agent, or applied separately, preferably previously, in a spraying, pipetting or dipping process.

In a preferred embodiment, the inorganic coating is initially applied to the stent, dried, then an organic coating is applied to this coating, dried and finally an active agent is applied. A solution of at least one active agent and possibly a matrix or carrier substance in a volatile solvent is preferably applied to the organic coating of the stent. The solvent or solvent mixture is then removed by evaporation at room temperature.

Suitable solvents are water and preferably organic solvents such as chloroform, methylene chloride (dichloromethane), acetone, tetrahydrofuran (THF), diethyl ether, methanol, ethanol, propanol, isopropanol, diethyl ketone, dimethylformamide (DMF), dimethylacetamide, ethyl acetic acid ester, dimethylsulfoxide (DMSO), benzene, toluene, xylene, t-butylmethylether (MTBE), petroleum ether (PE), cyclohexane, pentane, hexane, heptane, wherein chloroform and methylene chloride are particularly preferred.

Another preferred embodiment of the stents according to the invention has three coatings. In such three-layer systems, the first coating is the one applied directly to the stent. The second coating is the coating that is applied to this first coating. The coating applied to the second coating is referred to as the third coating.

According to the three-layer implementation, the first coating consists of a pure inorganic coating comprising magnesium fluoride coated with a second coating containing at least one organic polymer or consisting of this polymer only. The second coating is covered by a third coating containing at least one antiproliferative, antiphlogistic and/or antithrombogenic active agent, i.e. an antirestenotic active agent or consisting of this active agent only.

Instead of this three-layer assembly, the outer active agent layer can also be omitted and the active agent can be embedded in the organic coating. Thus, in another preferred embodiment, the inorganic coating is initially applied to the stent, dried, then an organic coating together with an active agent is applied to this coating and dried.

Of course, it is also possible to apply the active agent as an outer third layer to the middle organic layer containing the active agent. The middle organic layer may contain the same active agent in a different or the same concentration or a different active agent or no active agent is used in the middle organic layer.

A preferred embodiment of the invention thus consists of a stent consisting of a basic scaffold of one of the herein disclosed biodegradable magnesium alloys having at least 80% by weight magnesium as, an inorganic coating comprising magnesium fluoride, an organic coating and a polymeric coating, optionally at least one antirestenotic agent.

If the at least one active agent or combination of active agents is applied to the polymeric coating of the stent, further substances can be applied in combination with the at least one active agent or combination of active agents as pharmacologically acceptable carriers or as a matrix.

The already above mentioned polymers as wells as low molecular substances may serve as pharmacologically acceptable carriers, such as for example lactose, starch, sodium carboxymethyl starch, sorbitol, sucrose, magnesium stearate, dicalcium phosphate, calcium sulfate, talcum, mannitol, ethyl alcohol, polyvinyl alcohols, polyvinyl pyrrolidone, gelatine, naturally occurring sugars, naturally occurring as well as synthetic gums such as acacia gum or guar gum, sodium alginate, sodium benzoate, sodium acetate, glycerides, isopropyl myristates and palmitates, citrates, such as tributyl and triethyl citrates and their acetyl derivatives, phthalates such as dimethyl phthalate or dibutyl phthalate, etc. benzoic acid benzyl ester, triacetine, 2-pyrrolidone, boric acid, magnesium aluminium silicates, naturally occurring carob gum, gum karaya, guar, tragacanth, agar, cellulose, cellulose derivatives such as methyl cellulose, sodium carboxymethyl cellulose, hydroxypropyl methyl cellulose, microcrystalline cellulose as well as alginates, aluminas and bentonites, polyethylene glycol and also waxes such as for example beeswax, carnauba wax, candelilla wax and the like can be used. The matrix substance of the second layer can be identical to the polymer of the first layer. The additional carrier or matrix substances can be used in a weight ratio of up to 70% by wt., preferably to 50% by wt. based on the used active agent(s).

By means of known methods such as spraying, dipping, plasma, brushing, syringe, electrospinning or pipetting methods the polymeric coating is applied to the inorganic coating, which is already contained on the magnesium alloy of the basic scaffold, and preferably also adheres firmly to it. Thus, the stent according to the invention may be coated by spraying, pipetting, brushing, injection, plasma deposition or immersion methods, electrospinning, wherein the polymeric substance or mixtures of substances are dissolved in a solvent and this solution is applied to the implant. The solvent or solvent mixture is then removed by evaporation at room temperature. The coating of the stents according to the invention can be performed both before and after crimping onto a catheter balloon. If the coating is at first applied after the stent was attached to a catheter balloon, a dipping or spraying process is preferred. Thereby, the catheter balloon may possibly also be coated beyond the ends of the stent. The polymer can also be preformed in form of a tube and applied to the outer or inner surface of the basic scaffold of the stents according to the invention provided with the inorganic coating. If a tube is applied or the polymeric coating is applied as a full-surface coating, i.e. a coating covering the entire interspace, it is preferred that this polymeric coating extends beyond the length of the stent or the vascular graft and does not terminate with the ends of the vascular graft. In a further step, the protruding ends of the coating are placed to the outside around the edges of the vascular graft and the resulting edges are integrated into the underlying polymer layer under pressure and increased temperature. This ensures a reinforced coating at the stent ends and reduces the risk of detachment at these weak points.

The polymeric coating should be preformed relatively uniformly and should have a layer thickness of 0.01 to 100 µm. The desired layer thickness also depends on the respective polymer and can be achieved by multiple coating steps interrupted by drying steps. The coating thickness can be used to adjust the density of the polymeric coating. Particularly when the polymer is deposited from a gas phase, the coating becomes impermeable over a longer coating period. In case of short coating times, leaks occur that permit the diffusion of water or gases. Layer thicknesses of the polymeric coating from 0.01 to 90 µm are particularly preferred, further preferred from 0.01 to 80 µm, further preferred from 0.01 to 70 µm, further preferred from 0.01 to 60 µm, further preferred from 0.01 to 50 µm, further preferred from 0.01 to 40 µm, more preferred from 0.01 to 30 µm, more preferred from 0.01 to 20 µm, more preferred from 0.01 to 10 µm, more preferred from 0.05 to 10 µm, more preferred from 0.1 to 10 µm and most preferred from 0.5 to 10 µm.

Suitable solvents are water and preferably organic solvents such as chloroform, methylene chloride (dichloromethane), acetone, tetrahydro-furan (THF), diethyl ether, methanol, ethanol, propanol, isopropanol, diethyl ketone, Dimethylformamide (DMF), dimethylacetamide, ethyl acetic acid ester, dimethylsulfoxide (DMSO), benzene, toluene, xylene, t-butylmethylether (MTBE), petroleum ether (PE), cyclohexane, pentane, hexane, heptane, wherein chloroform and methylene chloride are particularly preferred.

In a suitable solvent or also together with the polymer, the at least one antiinflammatory, antiproliferative, antiangiogenic, antirestenotic (anti-restenosis), antineoplastic, antimigrative and/or antithrombogenic active agent to be applied can also be dissolved, emulsified, suspended or dispersed. If a polymer is contained as a matrix substance in the organic coating, this polymer can be dissolved and applied together with the active agent, or applied separately, preferably previously, in a spraying, pipetting or dipping process.

In a preferred embodiment, inorganic coating is initially applied to the stent scaffold, then the polymeric coating is applied to the inorganic coating, dried, and then an active agent is applied to the polymeric coating. A solution of at least one active agent and possibly a carrier substance in a volatile solvent is preferably applied to the polymeric coating of the stents. The solvent or solvent mixture is then removed by evaporation at room temperature.

Sample B is a stent of magnesium alloy A (Mg10Dy1Nd1Zn0.2Zr) followed by oxygen ion implantation. During ion implantation, oxygen ions are shot (implanted) into the surface to form a magnesium oxide layer.

Sample C is a stent of magnesium alloy A (Mg10Dy1Nd1Zn0.2Zr) followed by surface transformation, wherein a magnesium fluoride ($MgF_2$) layer is formed. The average values of dissolved magnesium over the time of three equal stents of sample C are shown.

Figure 1:
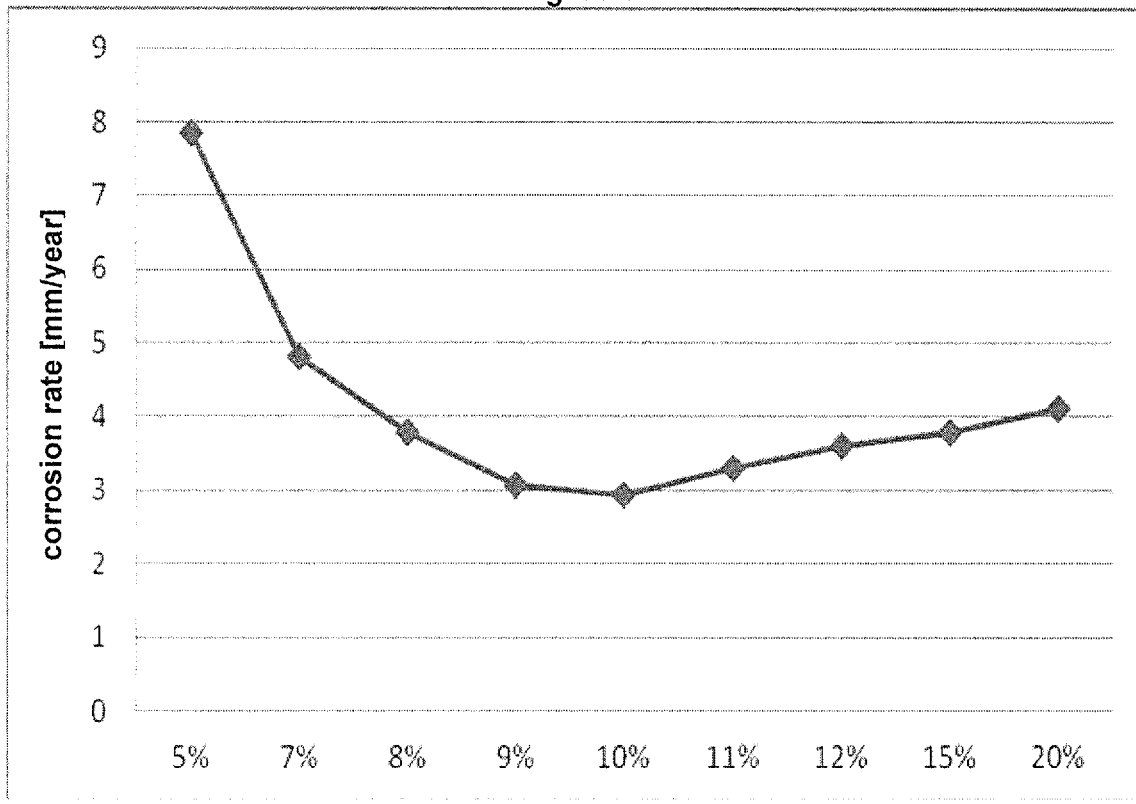
FIG. 1 shows a graphic representation of the results of the corrosion tests with binary magnesium alloys containing between 5 and 20% dysprosium and magnesium as balance. The corrosion was measured in 0.9% saline solution in a eudiometer. The data in % refer to the content of dysprosium in % by weight.
Figure 2:
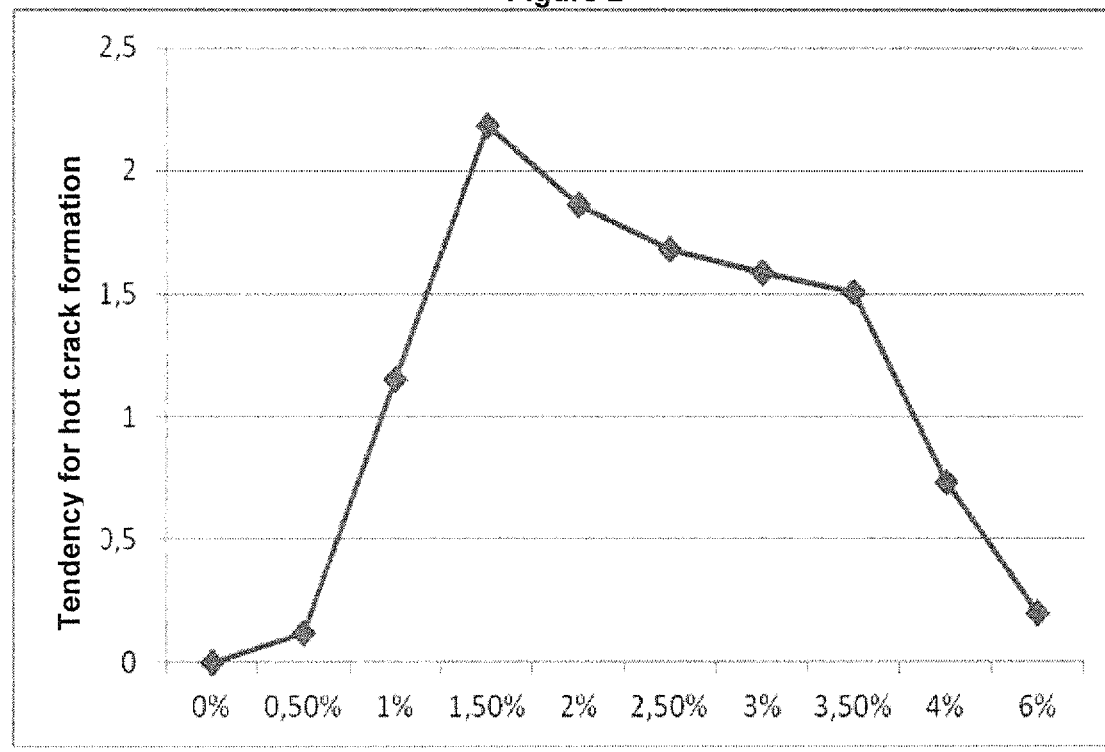
FIG. 2 shows a graphic representation of the dependence of the tendency for hot crack formation in connection with the amount of zinc in the alloy. Magnesium alloys containing 10% dysprosium, 1.0% by weight neodymium, increasing % by weight zinc, 0.2% by weight zirconium and the balance of magnesium were tested. The data in % refer to the content of zinc in % by weight.
Figure 3:
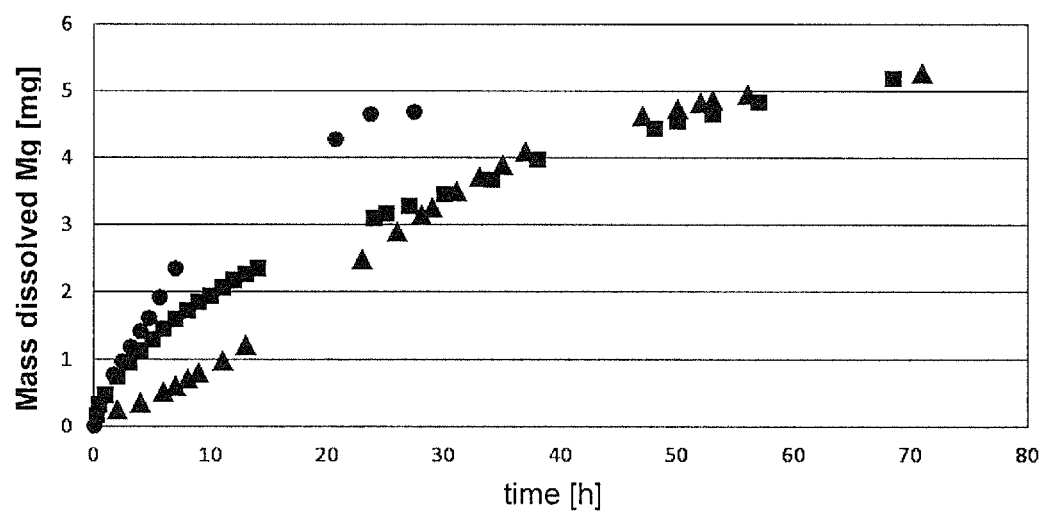
FIG. 3 shows a comparison of the photometric measurements to the degradation rates of the $O_2$ ion-implanted stent, stent of uncoated magnesium alloy A (bare metal stent (BMS)) and magnesium fluoride coated stent of magnesium alloy A. The dissolved masses of magnesium in PBS are applied over time. Sample A is a stent of magnesium alloy A (Mg10Dy1Nd1Zn0.2Zr) without further treatment. The average values of dissolved magnesium over the time of three equal stents of sample A are shown.
Figure 4:
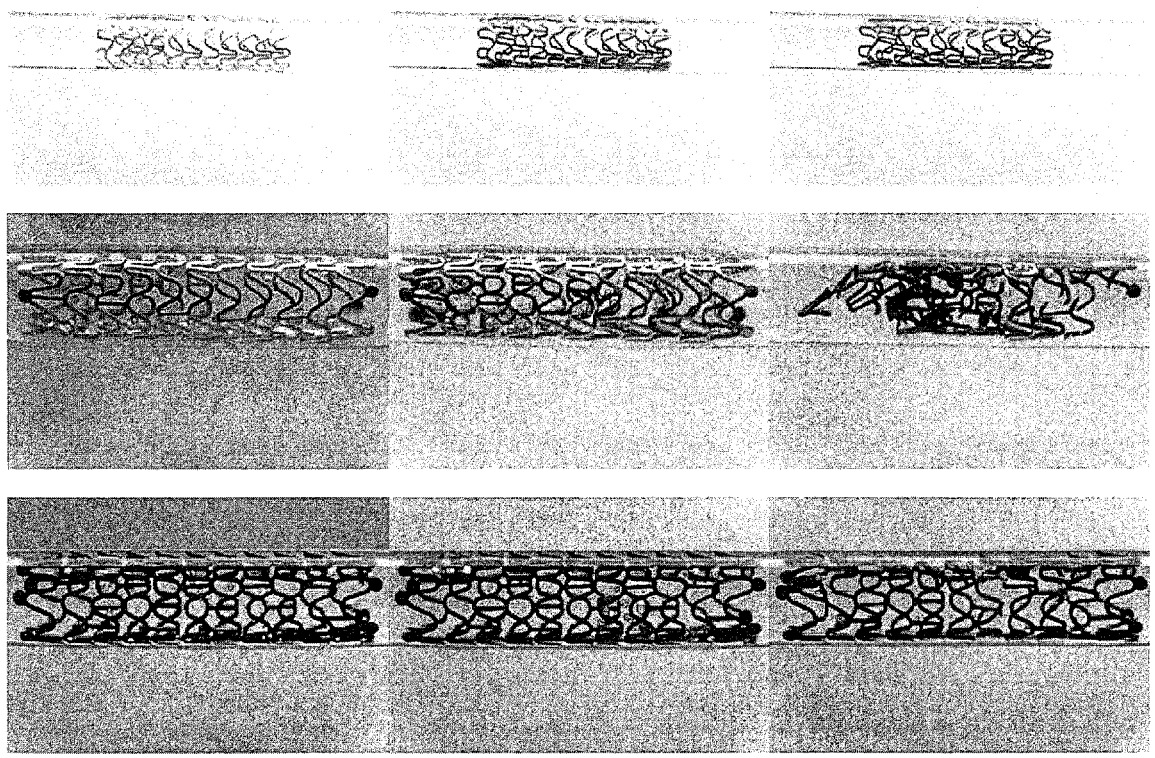

FIG. 4 shows camera images of the degradation of individual stents of samples A, B and C according to FIG. 3 and corresponding description.

The first line shows a stent of sample B (magnesium alloy A (Mg10Dy1Nd1Zn0.2Zr) and subsequent oxygen ion implantation). The first image (from left) is taken at the start of the degradation test. The second image shows the stent after 24 hours and the third image shows the stent after 36 hours in the PBS traversed tube.

The second line shows a stent of sample A (magnesium alloy A (Mg10Dy1Nd1Zn0.2Zr) without further treatment). The first image (from left) is taken at the start of the degradation test. The second image shows the stent after two hours and the third image shows the stent after six hours in the PBS traversed tube.

The third line shows a stent of sample C (magnesium alloy A (Mg10Dy1Nd1Zn0.2Zr) and subsequent surface transformation to produce $MgF_2$). The first image (from left) is taken at the start of the degradation test. The second image shows the stent after 13 hours and the third image shows the stent after 24 hours in the PBS traversed tube.

Figure 5:
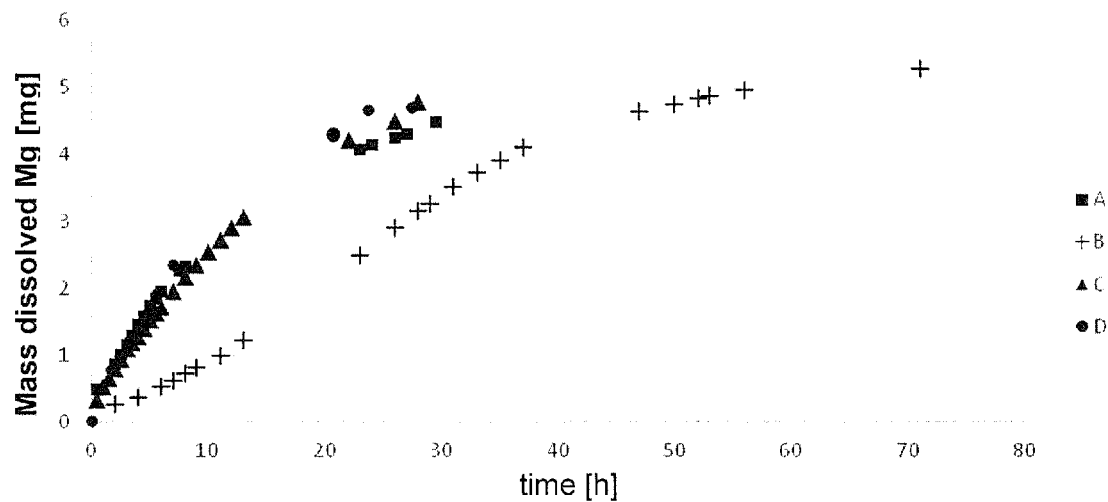

FIG. 5 shows a comparison of the photometric measurements to the degradation rates of $MgF_2$—, $MgCO_3$— and $Mg_3(PO_4)_2$ coated stents. The dissolved masses of magnesium in PBS are applied over time. Three stents with the same coating were measured and the average values of these measurements are shown in FIG. 5.

Sample A is a stent of magnesium alloy A (Mg10Dy1Nd1Zn0.2Zr) having a surface transformation for generation of a magnesium phosphate layer ($Mg_3(PO_4)_2$). For generation of this layer, the stent was immersed in a 10% sodium phosphate solution (50 ml) for 24 hours at a temperature below 50° C. The container with the sodium phosphate solution in turn was immersed in a heated water bath to ensure the temperature of 50° C. After 24 hours, the stent was removed and rinsed with deionized water and then dried in air. The average values of dissolved magnesium over the time of three equal stents of sample A are shown.

Sample B is a stent of magnesium alloy A (Mg10Dy1Nd1Zn0.2Zr) having a surface transformation for generation of a magnesium fluoride layer ($MgF_2$). For generation of this layer, the stent was immersed in a 40% hydrofluoric acid (50 ml) for 24 hours at a temperature below 50° C. The container with the hydrofluoric acid in turn was immersed in a heated water bath to ensure the temperature of 50° C. After 24 hours, the stent was removed and rinsed with deionized water and then dried in air. The average values of dissolved magnesium over the time of three equal stents of sample B are shown.

Sample C is a stent of magnesium alloy A (Mg10Dy1Nd1Zn0.2Zr) having a surface transformation for generation of a magnesium carbonate layer ($MgCO_3$). For generation of this layer, the stent was immersed in an alkaline 10% sodium carbonate solution (50 ml) for 26 hours at a temperature below 50° C. Sodium hydroxide was added to alkalize the solution. The container with the sodium carbonate solution in turn was immersed in a heated water bath to ensure the temperature of 50° C. After 26 hours, the stent was removed and rinsed with deionized water and then dried in air. The average values of dissolved magnesium over the time of three equal stents of sample B are shown.

Sample D is a stent of magnesium alloy A (Mg10Dy1Nd1Zn0.2Zr) without further treatment. The average values of dissolved magnesium over the time of three equal stents of sample D are shown.

Figure 6:
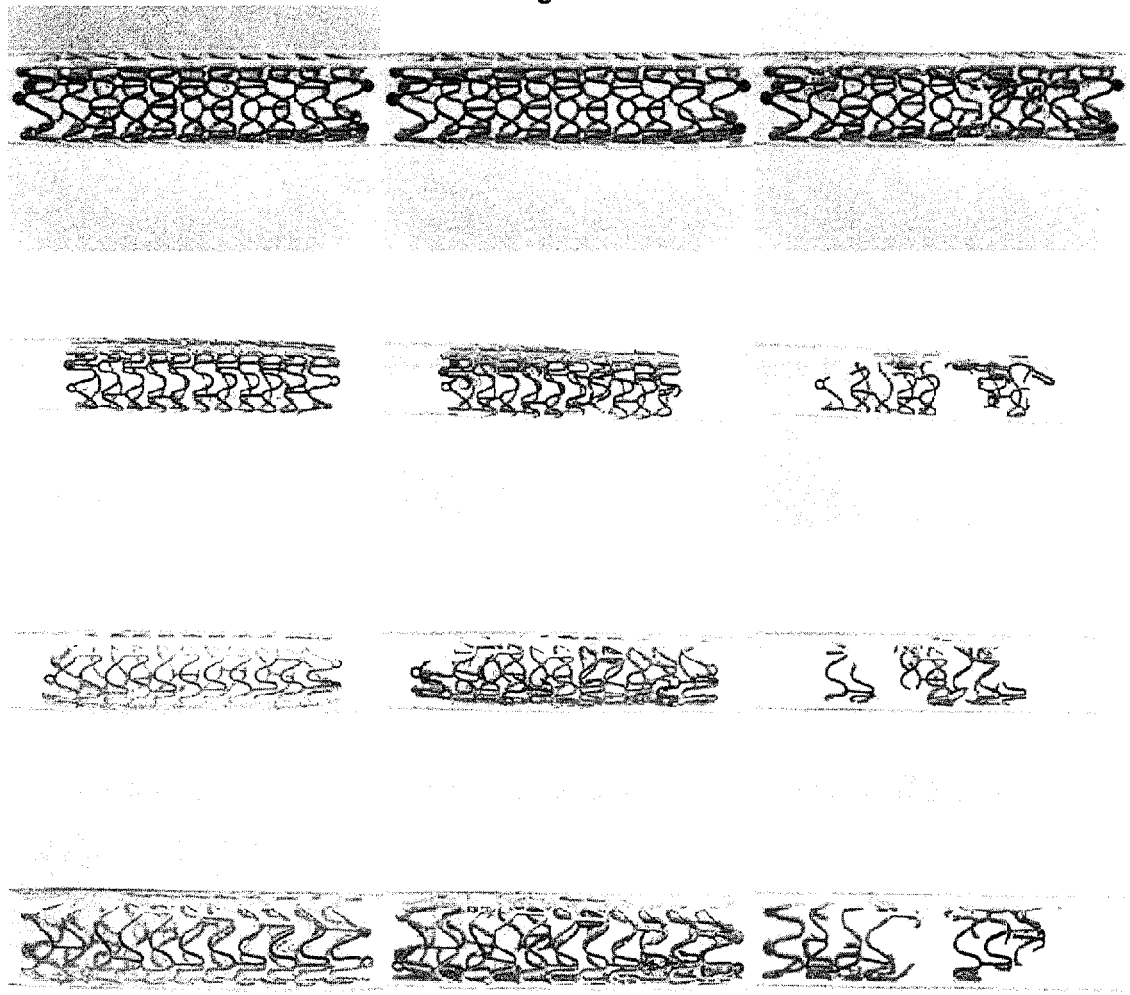

FIG. 6 shows individual stents of samples A, B, C and D according to FIG. 5 and corresponding description.

The first line shows a stent of sample B (magnesium alloy A (Mg10Dy1Nd1Zn0.2Zr) and subsequent $MgF_2$ surface transformation). The first image (from left) is taken at the start of the degradation test. The second image shows the stent after 10 hours and the third image shows the stent after 20 hours in the PBS traversed tube. The second line shows a stent of sample A (magnesium alloy A (Mg10Dy1Nd1Zn0.2Zr) and subsequent $Mg_3(PO_4)_2$ surface transformation). The first image (from left) is taken at the start of the degradation test. The second image shows the stent after ten hours and the third image shows the stent after 20 hours in the PBS traversed tube. The third line shows a stent of sample C (magnesium alloy A (Mg10Dy1Nd1Zn0.2Zr) and subsequent $MgCO_3$ surface transformation). The first image (from left) is taken at the start of the degradation test. The second image shows the stent after four hours and the third picture shows the stent after ten hours in the PBS traversed tube. The fourth line shows a stent of sample D (magnesium alloy A (Mg10Dy1Nd1Zn0.2Zr) without further treatment). The first image (from left) is taken at the start of the degradation test. The second image shows the stent after four hours and the third image shows the stent after ten hours in the PBS traversed tube.

FIG. 7 shows a comparison of photometric measurements to the degradation rates of $MgF_2$, $MgCO_3$ and $Mg_3(PO_4)_2$ coated stents as well as after a heat treatment, the annealing or an oxygen plasma treatment. The dissolved masses of magnesium in PBS are applied over time. The average values of two measurements (n=2) are shown.

Sample A is a stent of magnesium alloy A (Mg10Dy1Nd1Zn0.2Zr) having a surface transformation for generation of a magnesium fluoride layer ($MgF_2$). For generation of this layer, the stent was immersed in a 40% hydrofluoric acid (50 ml) for 24 hours at a temperature below 50° C. The container with the hydrofluoric acid in turn was immersed in a heated water bath to ensure the temperature of 50° C. After the 24 hours, the stent was removed and rinsed with deionized water and then dried in air. The stent was then annealed in air for 24.5 hours. The average values of dissolved magnesium over the time of two equal stents of sample A are shown.

Sample B is a stent of magnesium alloy A (Mg10Dy1Nd1Zn0.2Zr) having a surface transformation for generation of a magnesium oxide layer (MgO). For generation of this layer, the stent was placed in an oxygen plasma for 1.5 hours. The plasma is supposed to oxidize the surface of the stent to form a MgO layer. The stent was then annealed in air for 24.5 hours. The average values of dissolved magnesium over the time of two equal stents of sample B are shown.

The sample C is a stent of the magnesium alloy A (Mg10Dy1Nd1Zn0.2Zr) having a surface transformation for generation of a magnesium carbonate layer ($MgCO_3$). For generation of this layer, the stent was immersed for 24 hours at room temperature in an alkaline 10% sodium carbonate solution (50 ml). Sodium hydroxide was added to alkalize the solution. After the 24 hours the stent was removed and rinsed with deionized water and then dried in air. The stent was then annealed in air for 24.5 hours. The average values of dissolved magnesium over the time of two equal stents of sample C are shown.

Sample D is a stent of magnesium alloy A (Mg10Dy1Nd1Zn0.2Zr) having a surface transformation for generation of a magnesium phosphate layer ($Mg_3(PO_4)_2$). For generation of this layer, the stent was immersed for four days at room temperature in a 10% sodium phosphate solution (50 ml). After the four hours, the stent was removed and rinsed with deionized water and then dried in air. The stent was then annealed in air for 24.5 hours. The average values of dissolved magnesium over the time of two equal stents of sample D are shown.

Sample E is a stent of magnesium alloy A (Mg10Dy1Nd1Zn0.2Zr) having a plasma treatment for generation of a magnesium oxide layer (MgO) and subsequent surface transformation for generation of a $MgF_2$ layer. For generation of this layer, the stent was placed in an oxygen plasma for 1.5 hours. The plasma is supposed to oxidize the surface of the stent to form a MgO layer. Subsequently the stent was immersed in a 40% hydrofluoric acid (50 ml) for 24 hours at a temperature of below 50° C. The container with the hydrofluoric acid in turn was immersed in a heated water bath to ensure the temperature of 50° C. After the 24 hours, the stent was removed and rinsed with deionized water and then dried in air. The average values of dissolved magnesium over the time of two equal stents of sample E are shown.

Sample F is a stent of magnesium alloy A (Mg10Dy1Nd1Zn0.2Zr) without further treatment. The average values of dissolved magnesium over the time of three equal stents of sample F are shown.

FIG. 8 shows the degradation rate in PBS for an annealed $MgF_2$-coated stent and an annealed and plasma-treated stent. The dissolved masses of magnesium in PBS, which are photometrically determined, are applied over time.

Samples A and B are each stents of magnesium alloy A (Mg10Dy1Nd1Zn0.2Zr) having a surface transformation for generation of a magnesium fluoride layer ($MgF_2$). $MgF_2$ layer at 50° C. with hydrofluoric acid and then annealed.

Samples C and D are each stents of magnesium alloy A (Mg10Dy1Nd1Zn0.2Zr) having a plasma treatment for generation of a magnesium oxide layer (MgO) and then annealed.

Figure 9:
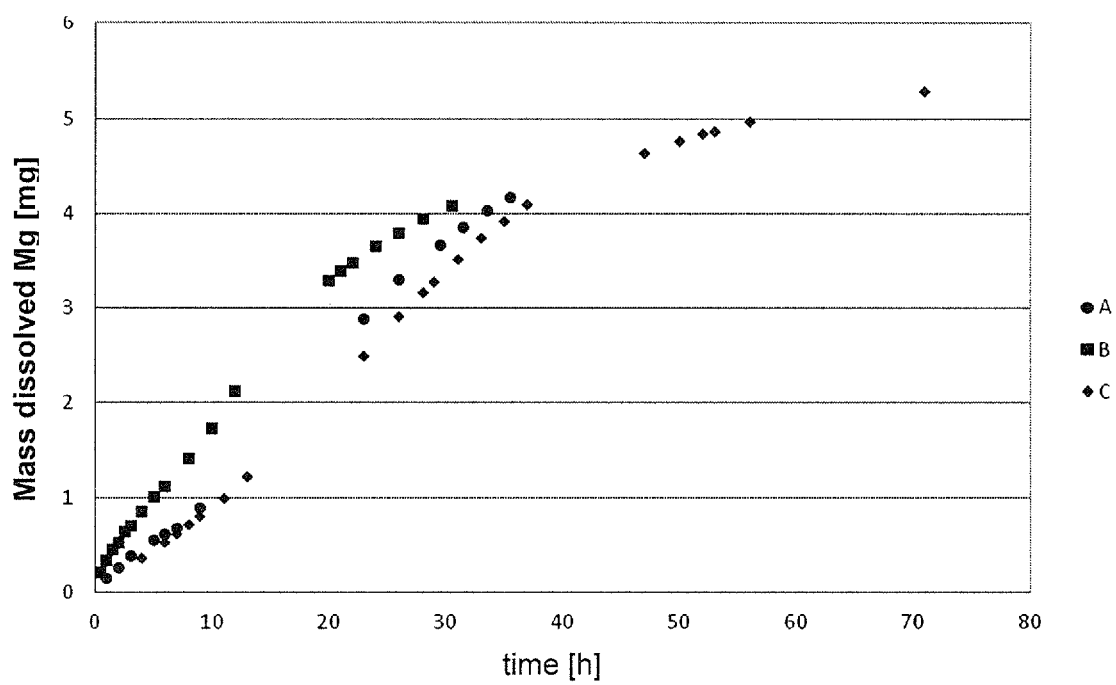

FIG. 9 shows the degradation rate in PBS for $MgF_2$-coated stents that are heat-treated, annealed or plasma-treated. The dissolved masses of magnesium in PBS, which are photometrically determined, are applied over time.

Sample A is a stent of magnesium alloy A (Mg10Dy1Nd1Zn0.2Zr) having a plasma treatment for generation of a magnesium oxide layer (MgO) and subsequent surface transformation for generation of an $MgF_2$ layer. For generation of this layer, the stent was placed in an oxygen plasma for 1.5 hours. The plasma is supposed to oxidize the surface of the stent to form a MgO layer. Subsequently the stent was immersed in a 40% hydrofluoric acid (50 ml) for 24 hours at a temperature of below 50° C. The container with the hydrofluoric acid in turn was immersed in a heated water bath to ensure the temperature of 50° C. After the 24 hours, the stent was removed and rinsed with deionized water and then dried in air. The average values of dissolved magnesium over the time of two equal stents of sample A are shown.

Sample B is a stent of magnesium alloy A (Mg10Dy1Nd1Zn0.2Zr) having a surface transformation for generation of a magnesium fluoride layer ($MgF_2$). For generation of this layer, the stent was immersed in a 40% hydrofluoric acid (50 ml) for 24 hours at a temperature below 50° C. The container with the hydrofluoric acid in turn was immersed in a heated water bath to ensure the temperature of 50° C. After the 24 hours, the stent was removed and rinsed with deionized water and then dried in air. The stent was then annealed in air for 24.5 hours. The average values of dissolved magnesium over the time of two equal stents of sample B are shown.

The sample C is a stent of the magnesium alloy A (Mg10Dy1Nd1Zn0.2Zr) and subsequent surface transformation, wherein a layer of magnesium fluoride ($MgF_2$) is formed. For generation of this layer, the stent was immersed in 40% hydrofluoric acid (50 ml) for 24 hours at a temperature of below 50° C. The container with the hydrofluoric acid in turn was immersed in a heated water bath to ensure the temperature of 50° C. After the 24 hours, the stent was removed and rinsed with deionized water and then dried in air. The average values of dissolved magnesium over the time of three equal stents of sample C are shown.

Figure 10:
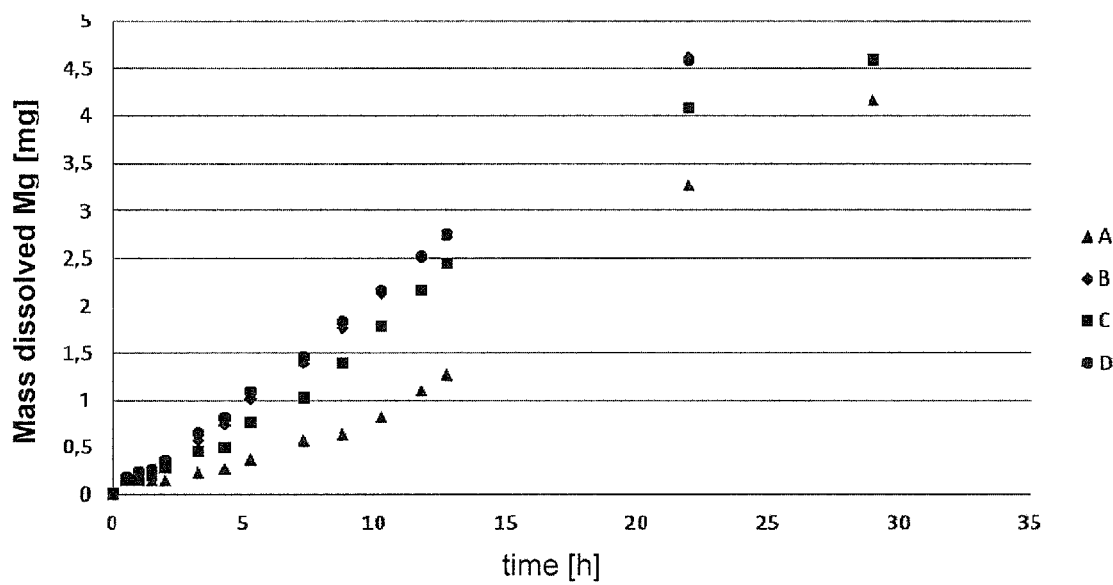

FIG. 10 shows the degradation rate in PBS for $MgF_2$-coated stents. The coating is produced under exposure of ammonium fluoride for 5 or 24 hours. On the other hand, 40% hydrofluoric acid for 5 and 24 hours is allowed to act on the stent to generate the coating. The dissolved masses of magnesium in PBS, which are photometrically determined, are applied over time. A=$MgF_2$-coated stent by treatment with hydrofluoric acid for 24 h; B=$MgF_2$-coated stent by treatment with ammonium fluoride for 24 h; C=$MgF_2$-coated stent by treatment with hydrofluoric acid for 5 h; B=$MgF_2$-coated stent by treatment with ammonium fluoride for 5 h.

Sample A is stent of magnesium alloy A (Mg10Dy1Nd1Zn0.2Zr) and subsequent surface transformation, wherein a magnesium fluoride ($MgF_2$) layer is formed. For generation of this layer, the stent was immersed in 40% hydrofluoric acid (50 ml) for 24 hours at a temperature of below 50° C. The container with the hydrofluoric acid in turn was immersed in a heated water bath to ensure the temperature of 50° C. After the 24 hours, the stent was removed and rinsed with deionized water and then dried in air. The measured values of dissolved magnesium over the time of a stent of sample A are shown.

Sample B is a stent of the magnesium alloy A (Mg10Dy1Nd1Zn0.2Zr) and subsequent surface transformation, wherein a layer of magnesium fluoride ($MgF_2$) is formed. For generation of this layer, the stent was immersed in a 10% ammonium fluoride solution (50 ml) for 24 hours at a temperature below 50° C. The container with the solution in turn was immersed in a heated water bath to ensure the temperature of 50° C. After the 24 hours, the stent was removed and rinsed with deionized water and then dried in air. The measured values of dissolved magnesium over the time of a stent of sample B are shown.

The sample C is a stent of the magnesium alloy A (Mg10Dy1Nd1Zn0.2Zr) and subsequent surface transformation, wherein a layer of magnesium fluoride ($MgF_2$) is formed. For generation of this layer, the stent was immersed in 40% hydrofluoric acid (50 ml) for five hours at a temperature below 50° C. The container with the hydrofluoric acid in turn was immersed in a heated water bath to ensure the temperature of 50° C. After five hours, the stent was removed and rinsed with deionized water and then dried in air. The measured values of dissolved magnesium over the time of a stent of sample C are shown.

The sample D is a stent of the magnesium alloy A (Mg10Dy1Nd1Zn0.2Zr) and subsequent surface transformation, wherein a layer of magnesium fluoride ($MgF_2$) is formed. For generation of this layer, the stent was immersed a 10% ammonium fluoride solution (50 ml) for five hours at a temperature below 50° C. The container with the solution in turn was immersed in a heated water bath to ensure the temperature of 50° C. After the five hours, the stent was removed and rinsed with deionized water and then dried in air. The measured values of dissolved magnesium over the time of a stent of sample D are shown.

Figure 11:
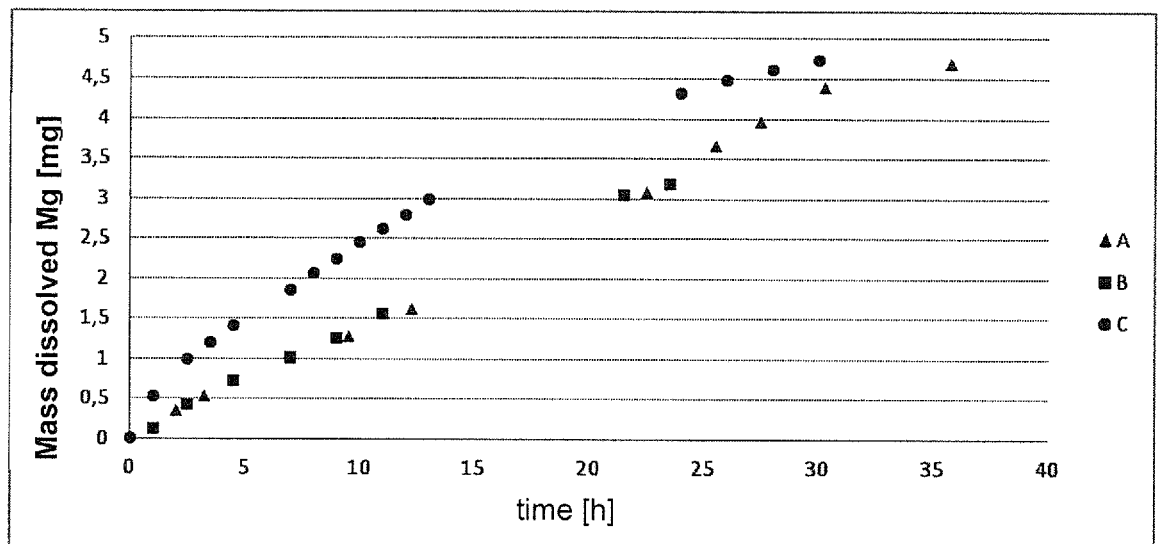

FIG. 11 shows the degradation rate of magnesium alloys treated by ion implantation (oxygen, fluorine and carbon).

Sample A is a stent of magnesium alloy A (Mg10Dy1Nd1Zn0.2Zr) having an oxygen implantation.

Sample B is stent of a magnesium alloy A (Mg10Dy1Nd1Zn0.2Zr) having a fluorine implantation.

Sample C is a stent of the uncoated magnesium alloy A (Mg10Dy1Nd1Zn0.2Zr).

Figure 12:
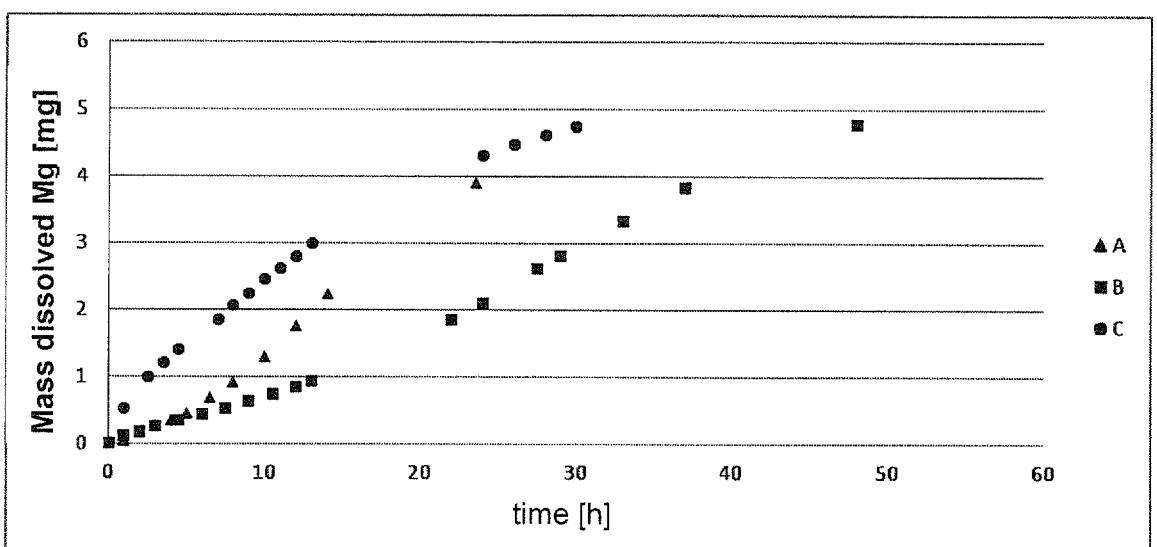

FIG. 12 shows the degradation rate of stents after additional heat treatment and subsequent fluoridation.

Group A: Previously additionally heat-treated stents of magnesium alloy A were treated with 38-40% hydrofluoric acid.

Group B: Previously heat-treated stents of magnesium alloy A were treated with 48% hydrofluoric acid.

Group C: Untreated stents of magnesium alloy A (Mg10Dy1Nd1Zn0.2Zr) with the same design and same material lot as group A and B.

Figure 13:
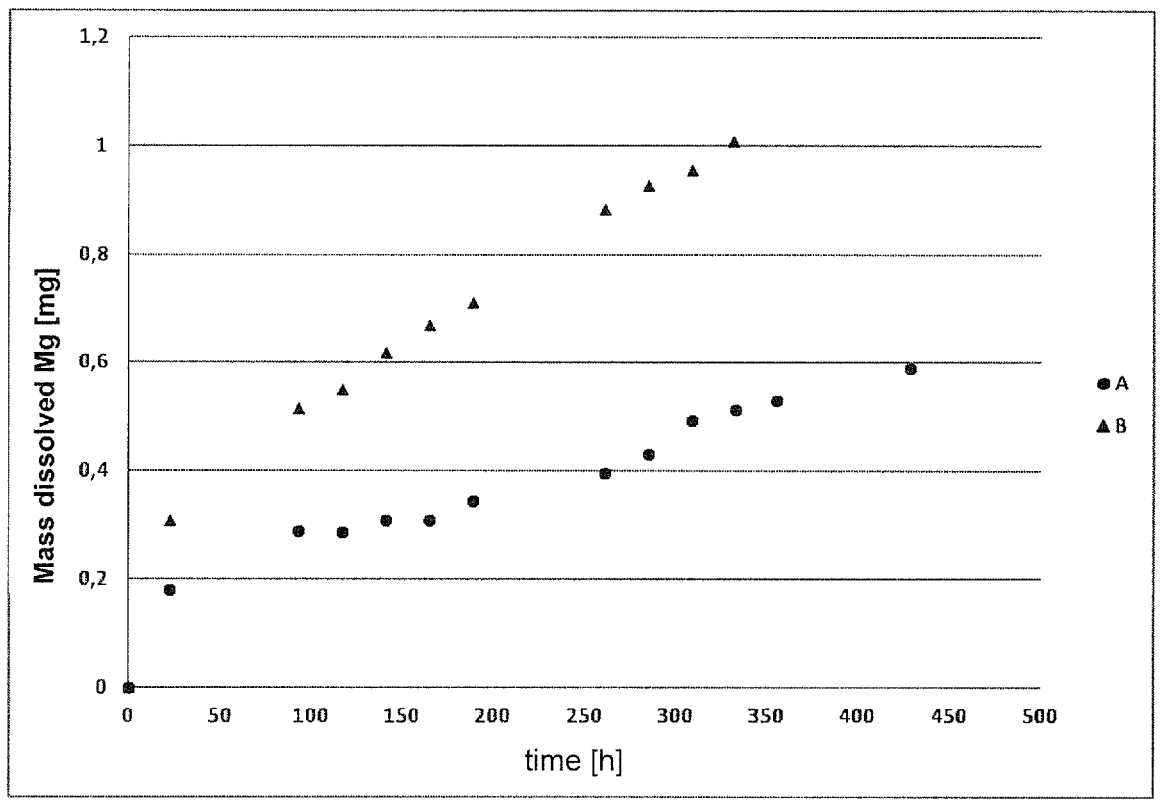

FIG. 13 shows the degradation rate of stents having an intermediate layer of magnesium fluoride and a further coating of parylene C.

Sample A: Stents of magnesium alloy A treated with hydrofluoric acid and then coated with parylene C polymer.

Sample B: Stents coated with parylene C polymer but not fluoridated.

Figure 14:
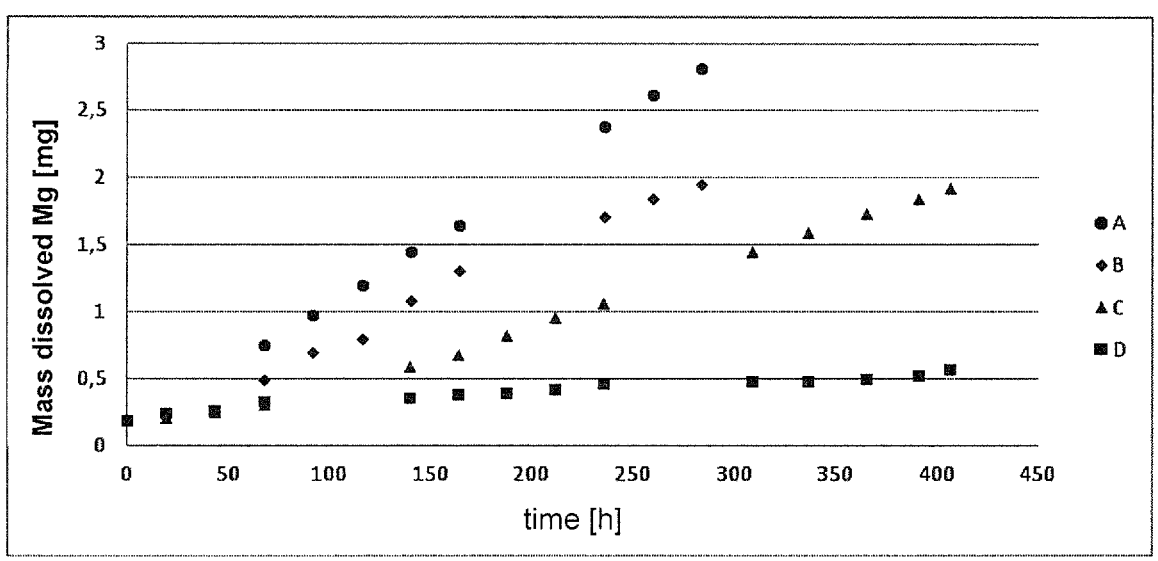

FIG. 14 Degradation tests of stents having an intermediate layer of magnesium fluoride and a further coating of a resorbable polymer Group A: Stents of magnesium alloy A (Mg10Dy1Nd1Zn0.2Zr) having a layer of poly(L-lactide) (PLLA), which was applied to the stent by spraying method.

Group B: Stents of magnesium alloy A (Mg10Dy1Nd1Zn0.2Zr) having a layer of poly-ε-caprolactone (PCL), which was applied to the stent by spraying method.

Group C: Stents of magnesium alloy A (Mg10Dy1Nd1Zn0.2Zr) having a layer of poly(L-lactide) (PLLA), which was applied to the stent by spraying method and an intermediate layer of magnesium fluoride. The magnesium fluoride layer was applied to the stents as in example 13 (group A).

Group D: Stents of magnesium alloy A (Mg10Dy1Nd1Zn0.2Zr) having a layer of poly-ε-caprolactone (PCL), which was applied to the stent by spraying method and an intermediate layer of magnesium fluoride. The magnesium fluoride layer was applied to the stents as in example 13 (group A).

Figure 15:
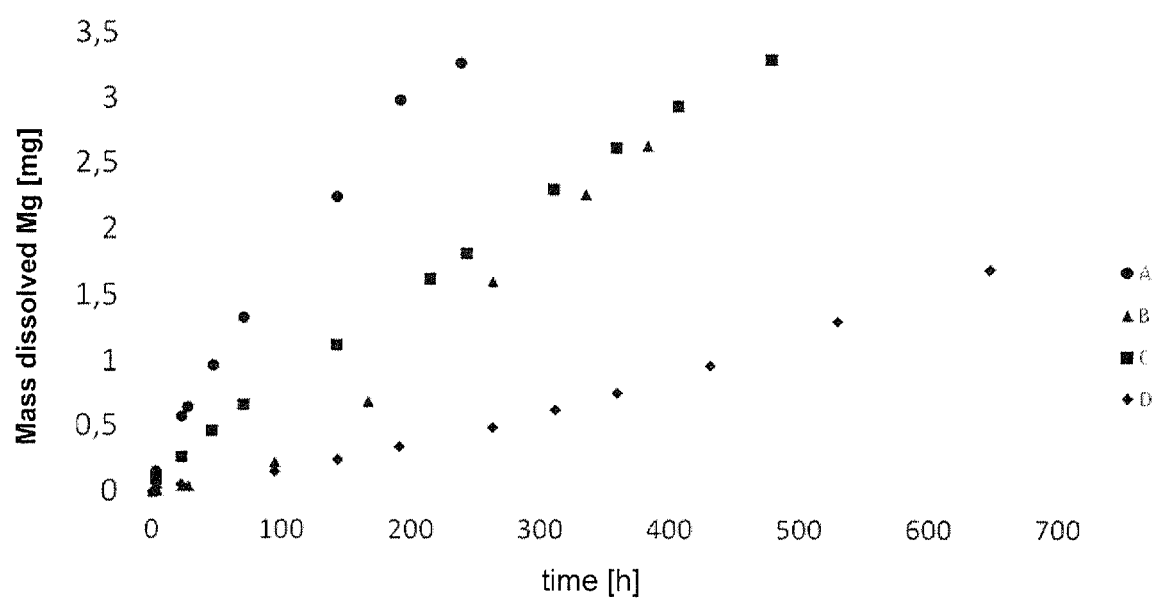

FIG. 15 shows the degradation rate of stents of magnesium alloy A (Mg10Dy1Nd1Zn0.2Zr) having an intermediate layer of magnesium fluoride and a further coating of bioresorbable polymer (PCL) of different layer thickness and introduced antirestenotic active agent (rapamycin).

Group A: Stents of magnesium alloy A (Mg10Dy1Nd1Zn0.2Zr) with a 4 μm layer of poly-ε-caprolactone (PCL), which was applied to the stent by spraying method.

Group B: Stents of magnesium alloy A (Mg10Dy1Nd1Zn0.2Zr) with a 7 μm layer of poly-ε-caprolactone (PCL), which was applied to the stent by spraying method.

Group C: Stents of magnesium alloy A (Mg10Dy1Nd1Zn0.2Zr) with a 4 μm layer of poly-ε-caprolactone (PCL), which was applied to the stent by spraying method and an intermediate layer of magnesium fluoride. The magnesium fluoride layer was applied to the stents as in example 13 (group A).

Group D: Stents of magnesium alloy A (Mg10Dy1Nd1Zn0.2Zr) with a 7 μm layer of poly-ε-caprolactone (PCL), which was applied to the stent by spraying method and an intermediate layer of magnesium fluoride. The magnesium fluoride layer was applied to the stents as in example 13 (group A).

Figure 16:
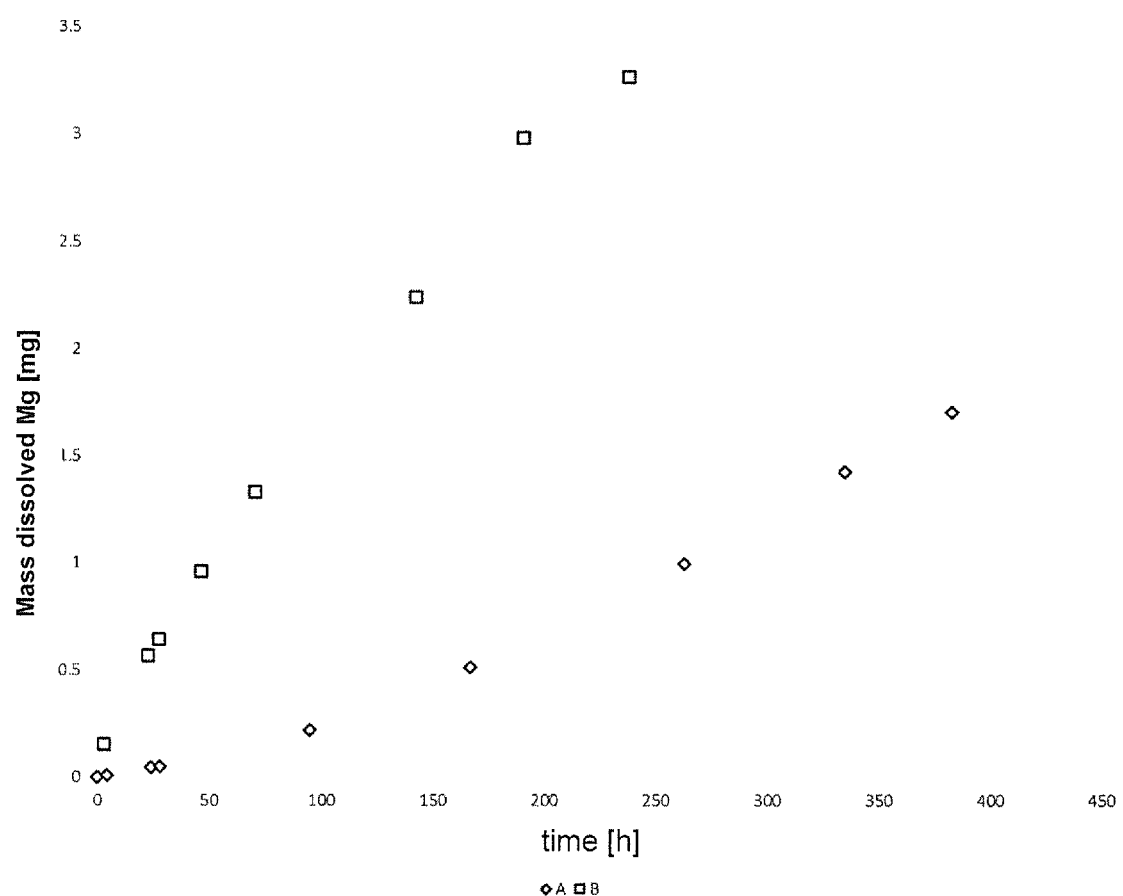

FIG. 16 shows the degradation rate of stents of magnesium alloy A (Mg10Dy1Nd1Zn0.2Zr) with and without an intermediate layer of magnesium fluoride and a further coating of bioresorbable polymer (PLLA) and introduced antirestenotic active agent (rapamycin).

Group A: Stents of magnesium alloy A (Mg10Dy1Nd1Zn0.2Zr) with a 7 μm layer of poly-L-lactide (PLLA) with introduced drug (rapamycin) applied by spraying method and an intermediate layer of magnesium fluoride.

Group B: Stents of magnesium alloy A (Mg10Dy1Nd1Zn0.2Zr) with a 7 μm layer of poly-L-lactide (PLLA) with introduced drug (rapamycin) applied to the stent by spraying method.

Figure 17:
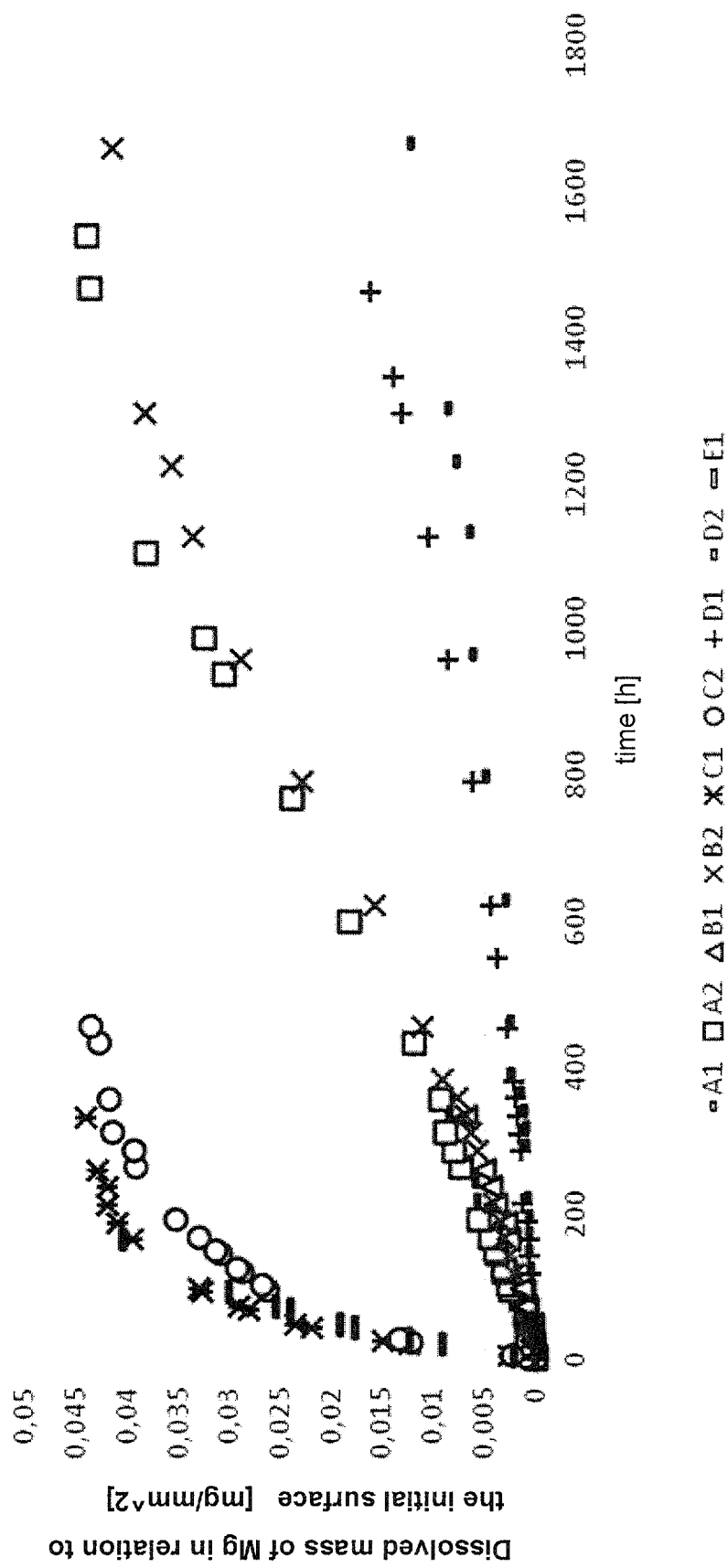

FIG. 17: shows the degradation rate of stents of magnesium alloy A (Mg10Dy1Nd1Zn0.2Zr) having an inorganic intermediate layer and a further coating of PLLA (with different composition of the inorganic intermediate layer).

Group A: Stents of magnesium alloy A (Mg10Dy1Nd1Zn0.2Zr) having an inorganic coating (surface transformation) of magnesium hydroxide and a 5 μm layer of poly-L-lactide (PLLA), which was applied by spraying method. The magnesium hydroxide surface was applied to the stents in a wet chemical process. For this purpose the polished stents were immersed for 2 min in 30% $H_2O_2$ solution at room temperature. Subsequently they were then rinsed with $H_2O$ and immersed in ethanol and dried at 80° C. for one hour in a drying chamber.

Group B: Stents of magnesium alloy A (Mg10Dy1Nd1Zn0.2Zr) having an inorganic coating (surface transformation) of magnesium carbonate/magnesium hydroxide and a 5 μm layer of poly-L-lactide (PLLA), which was applied by spraying method. The surface transformation was realized by means of a wet chemical process. Thereby the polished stents were immersed in saturated $NaHCO_3$ solution for 5 min and at 37° C. Subsequently the stents were then rinsed with $H_2O$ and immersed in ethanol. Afterwards the stents were dried at 100° C. for one hour in a drying chamber.

Group C: Stents of magnesium alloy A (Mg10Dy1Nd1Zn0.2Zr) having an inorganic coating (surface transformation) of magnesium phosphate/magnesium hydroxide and a 10 μm layer of poly-L-lactide (PLLA), which was applied by spraying method. The surface transformation was realized by means of a wet chemical process. Thereby the polished stents were immersed in saturated $Na_2HPO_4$ solution for one hour at 37° C. The stents were then rinsed with $H_2O$ and immersed in ethanol. This was followed by drying at 100° C. for one hour in a drying chamber.

Group D: Stents of magnesium alloy A (Mg10Dy1Nd1Zn0.2Zr) having an inorganic coating (surface transformation) of magnesium fluoride and a 5 μm layer of poly-L-lactide (PLLA), which was applied by spraying method. The magnesium fluoride layer was applied to the stents as in example 13 (group A).

Group E: Stent of magnesium alloy A (Mg10Dy1Nd1Zn0.2Zr) having an inorganic coating (surface transformation) of magnesium fluoride. The magnesium fluoride layer was applied to the stents as in example 13 (group A).

Figure 18:
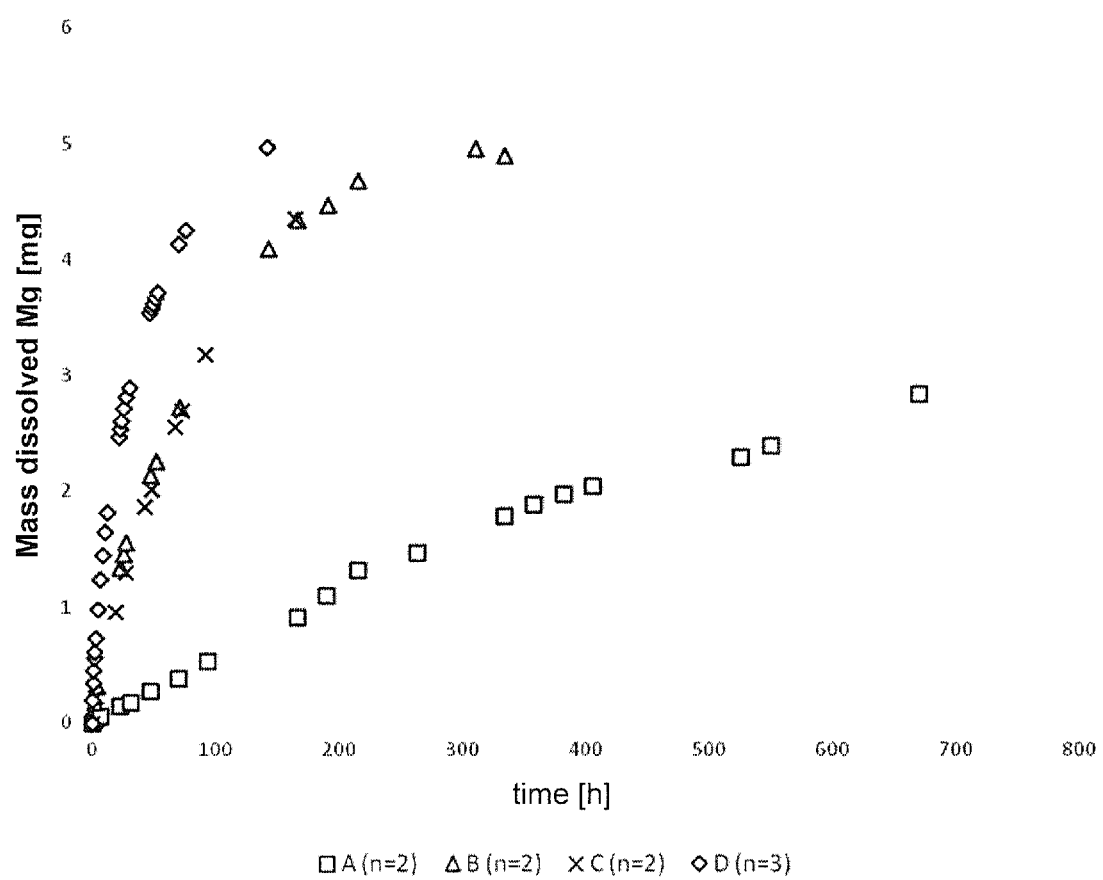

FIG. 18 shows the degradation rate of magnesium alloy A (Mg10Dy1Nd1Zn0.2Zr) stents with and without an inorganic intermediate layer and a further coating of parylene N.

Group A: Two stents of magnesium alloy A (Mg10Dy1Nd1Zn0.2Zr) were treated as in example 13 group B to obtain a magnesium fluoride layer. The stents were then coated with the polymer parylene N (poly-p-xylylene). Parylene N can be deposited directly from the gas phase by condensation on the substrate, resulting in a very uniform coating. The layer thickness can be varied over the duration of the treatment.

Group B: The two stents of group B were coated directly (thus without an intermediate layer of magnesium fluoride) with the polymer parylene N. The layer thickness of the polymer was the same as these were coated in the same coating cycle as the stents of group A.

Group C: The two stents were treated as in group A, but no polymer was applied.

Group D: The three stents had no coating (no magnesium fluoride layer and no polymer layer).

Figure 19:
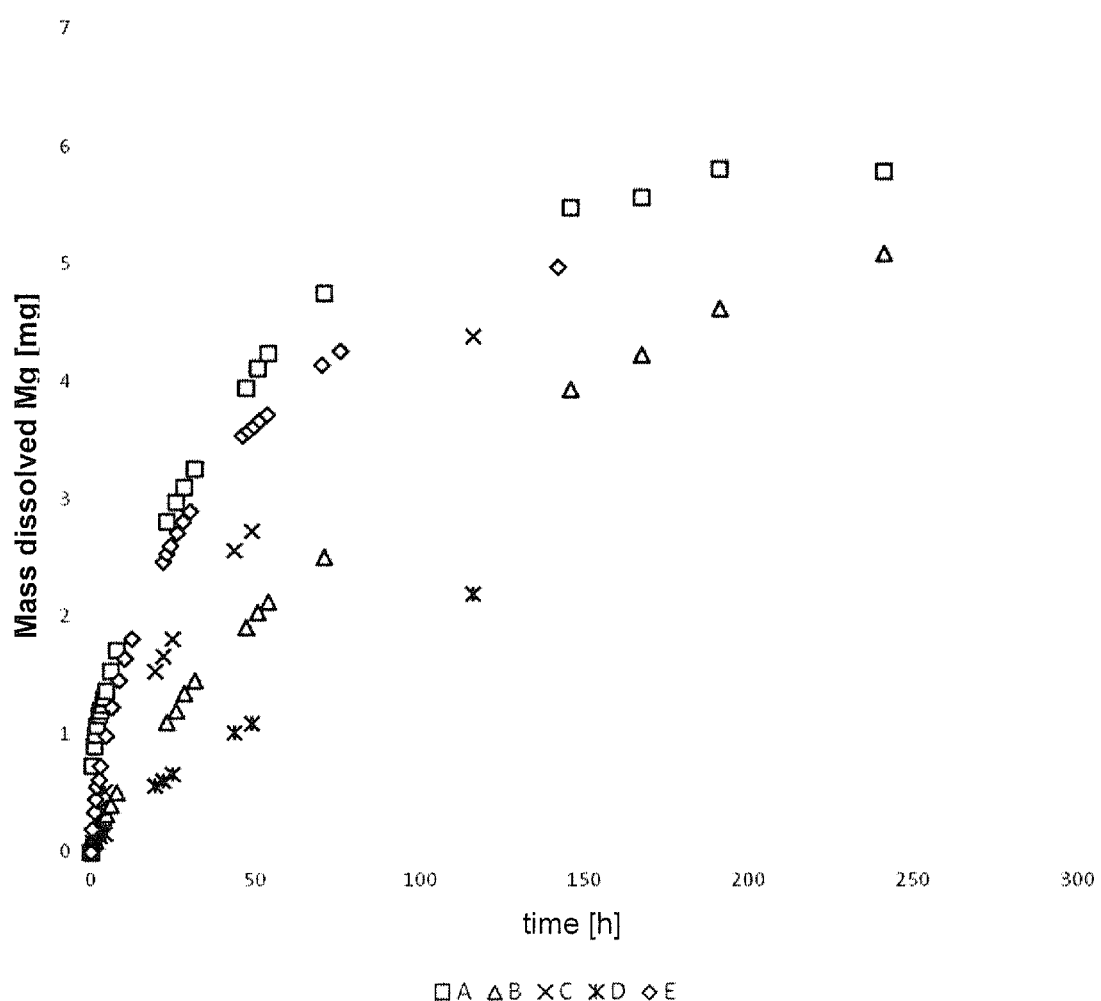

FIG. 19: shows the degradation rate of stents of magnesium alloy A (Mg10Dy1Nd1Zn0.2Zr) with and without an inorganic intermediate layer and a further double coating of polyethyleneimine (PEI) and polyacrylic acid (PAA).

Group A: A stent of magnesium alloy A (Mg10Dy1Nd1Zn0.2Zr) and a layer of PEI and PAA. The double layer of PEI and PAA was applied in a layer by layer process. The stent was immersed successively in an aqueous solution of 5 mg/ml PAA for two minutes, then in deionized water for one minute, then in an aqueous solution of 5 mg/ml PEI for two minutes and finally in deionized water for one minute. This sequence was repeated five times and the stent dried in air afterwards.

Group B: A stent of magnesium alloy A (Mg10Dy1Nd1Zn0.2Zr), which was treated as in example 13 Group B to generate an intermediate layer of magnesium fluoride. This was followed by the same coating sequence as for Stent A (5×PEI and PAA).

Group C: Similarly coated stent as stent A but with 10 coating rounds for generation of the PEI and PAA layer.

Group D: Similarly coated stent as stent B but with 10 coating rounds for generation of the PEI and PAA layer.

Group E: Stents of magnesium alloy A (Mg10Dy1Nd1Zn0.2Zr) without any further coating.

Figure 20:
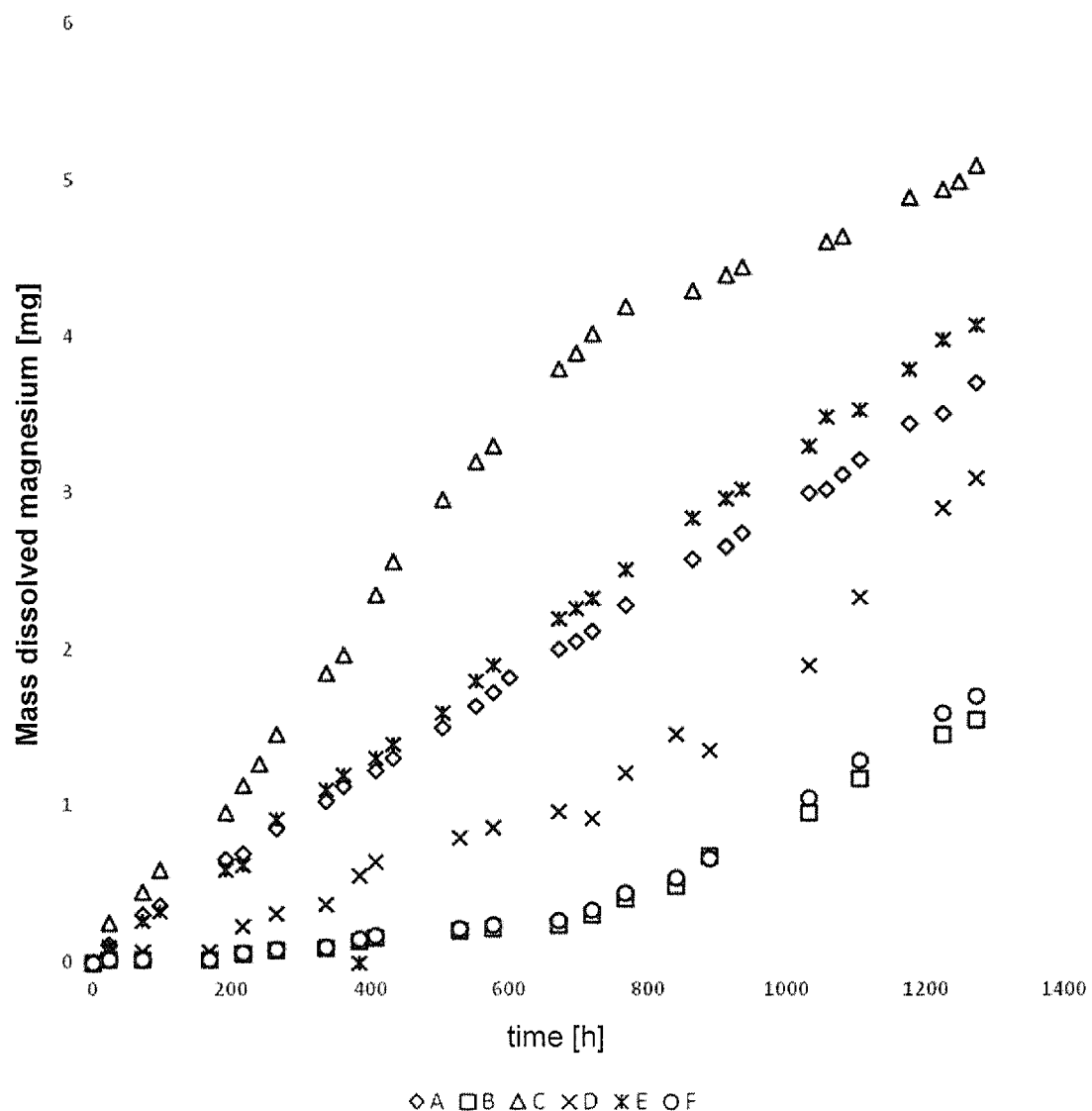

FIG. 20 shows the degradation rate of magnesium alloy A (Mg10Dy1Nd1Zn0.2Zr) stents with and without an inorganic intermediate layer and a further coating of poly-L-lactide (PLLA) compared to similarly coated stents of alloys L37 and AZ91 (Mg9Al1Zn).

Group A: Stents of magnesium alloy A (Mg10Dy1Nd1Zn0.2Zr) with a 5 μm layer of poly-L-lactide (PLLA), which was applied by spraying method.

Group B: Stents of magnesium alloy A (Mg10Dy1Nd1Zn0.2Zr) having an inorganic coating (surface transformation) of magnesium fluoride and a 5 μm layer of poly-L-lactide (PLLA), which was applied by spraying method. The magnesium fluoride layer was applied to the stents as in example 13 (group B).

Group C: Stents of magnesium alloy L37 with a 5 µm layer of Poly-L-Lactide (PLLA), which was applied by spraying method.

Group B: Stents of magnesium alloy L37 having an inorganic coating (surface transformation) of magnesium fluoride and a 5 µm layer of poly-L-lactide (PLLA), which was applied by spraying method. The magnesium fluoride layer was applied to the stents as in example 13 (group B).

Group E: Stents of magnesium alloy AZ91 with a 5 µm layer of poly-L-lactide (PLLA), which was applied by spraying method.

Group F: Stents of magnesium alloy AZ91 having an inorganic coating (surface transformation) of magnesium fluoride and a 5 µm layer of poly-L-lactide (PLLA), which was applied by spraying method. The magnesium fluoride layer was applied to the stents as in example 13 (group B).

Figure 21:
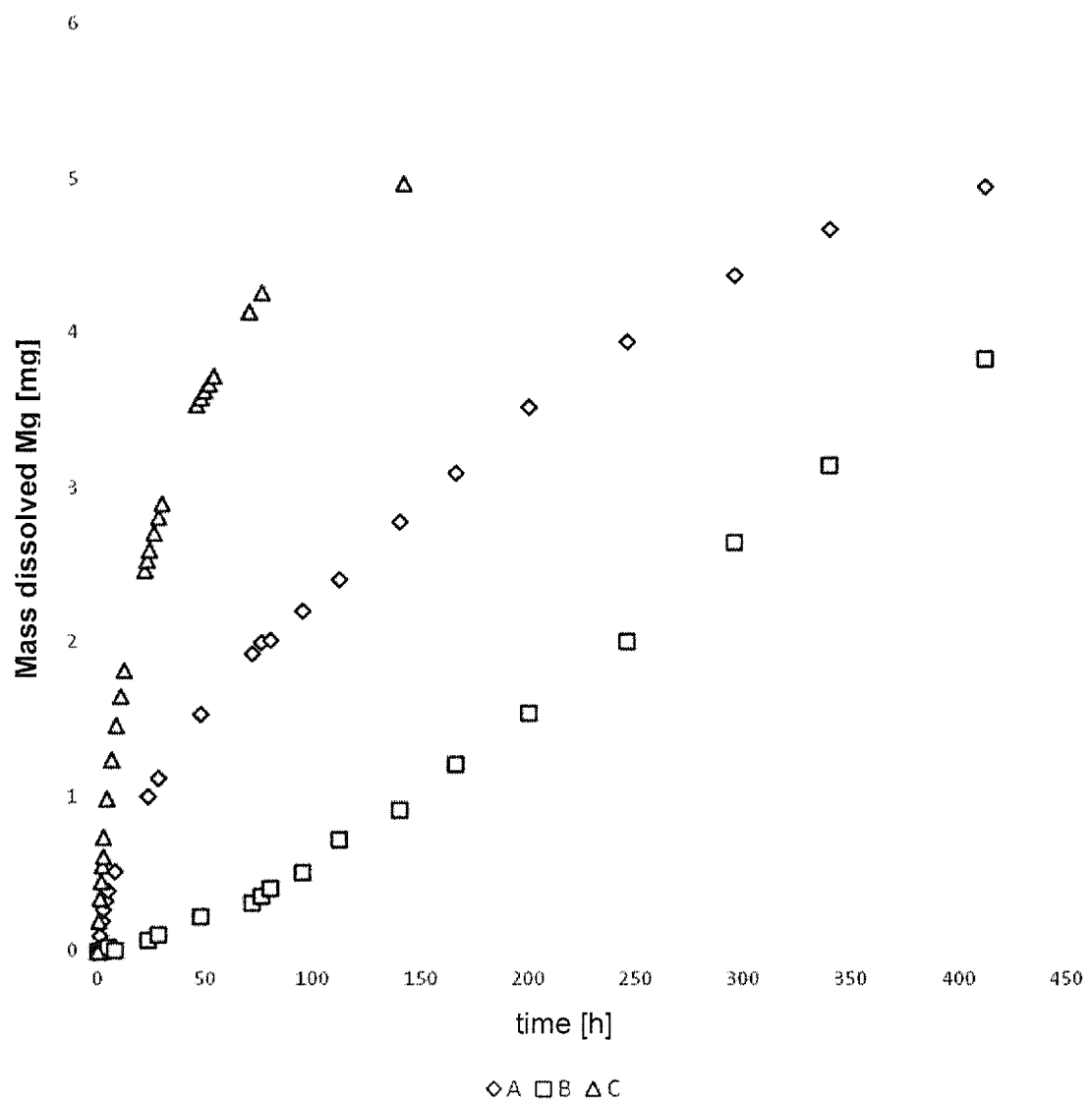

FIG. 21 shows the degradation rate of stents of magnesium alloy A (Mg10Dy1Nd1Zn0.2Zr) with and without an inorganic intermediate layer of magnesium fluoride and a further coating of poly(lactide-co-glycolide).

Group A: Stents of magnesium alloy A (Mg10Dy1Nd1Zn0.2Zr) having a layer of poly(lactid-co-glycolide) (PLGA), which was applied by dip coating. Thereby the stent was immersed in a solution of PLGA (85:15) and trichloromethane (5 mg/ml), pulled out of the solution at 20 mm/min and then dried in air at 40° C.

Group B: Stents of magnesium alloy A (Mg10Dy1Nd1Zn0.2Zr) having an inorganic coating (surface transformation) of magnesium fluoride and an overlying layer of PLGA. The magnesium fluoride coating has been applied as in example 13 group B. The PLGA coating was applied as in group A.

Group C: Stents of magnesium alloy A (Mg10Dy1Nd1Zn0.2Zr) without any coating.

Figure 22:
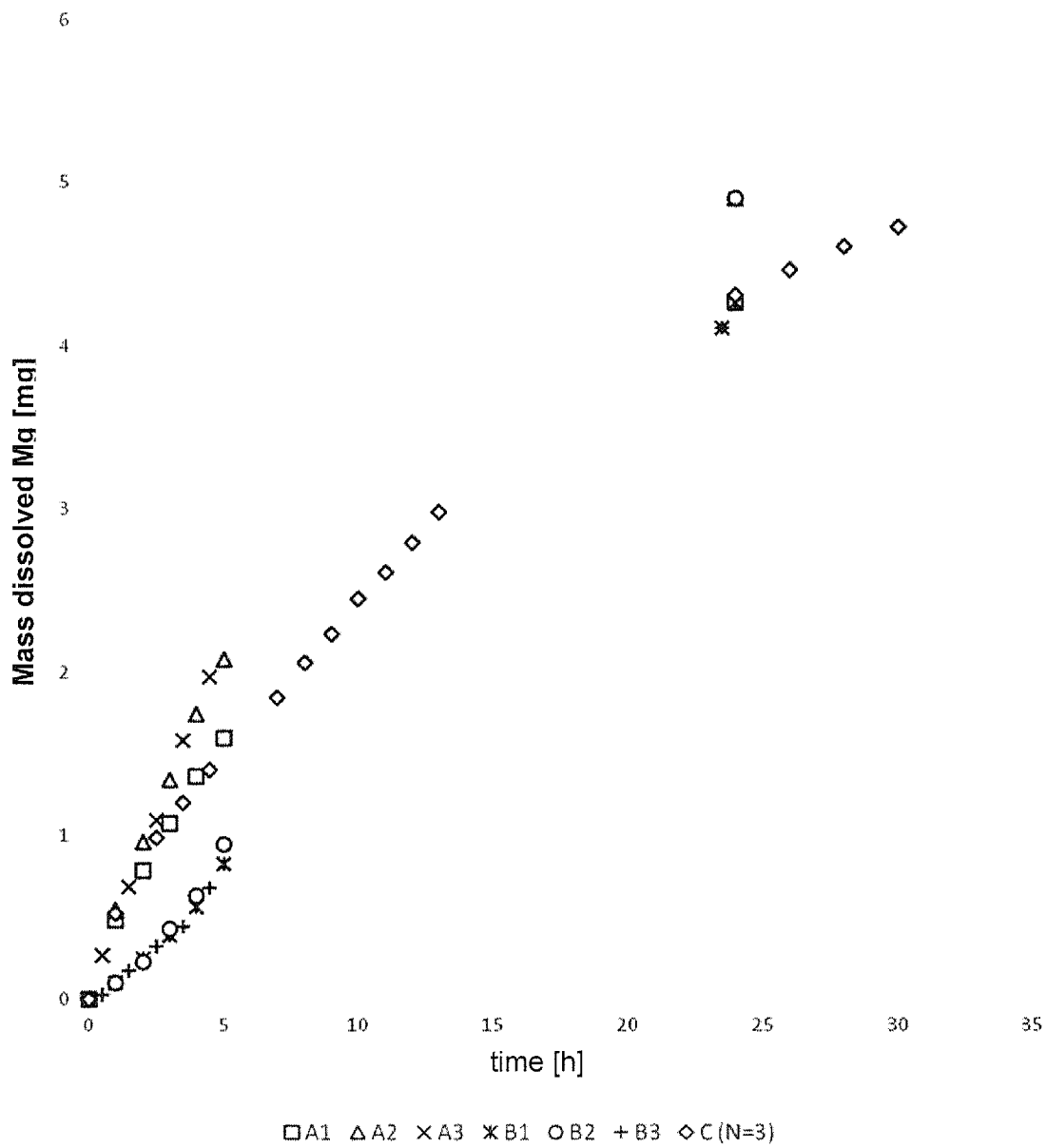

FIG. 22 shows the degradation rate of stents of magnesium alloy A (Mg10Dy1Nd1Zn0.2Zr) with and without an inorganic intermediate layer of magnesium fluoride and a further coating of polymethacrylamide (PMAA) in comparison to uncoated stents.

Group A: Three stents of magnesium alloy A (Mg10Dy1Nd1Zn0.2Zr) having a layer of PMAA, which was applied by dip coating (A1, A2, A3).

Group B: Stents of magnesium alloy A (Mg10Dy1Nd1Zn0.2Zr) having an inorganic coating (surface transformation) of magnesium fluoride and an overlying layer of PMAA (B1, B2, B3).

Group C: Stents of magnesium alloy A (Mg10Dy1Nd1Zn0.2Zr) without any coating.

Figure 23:
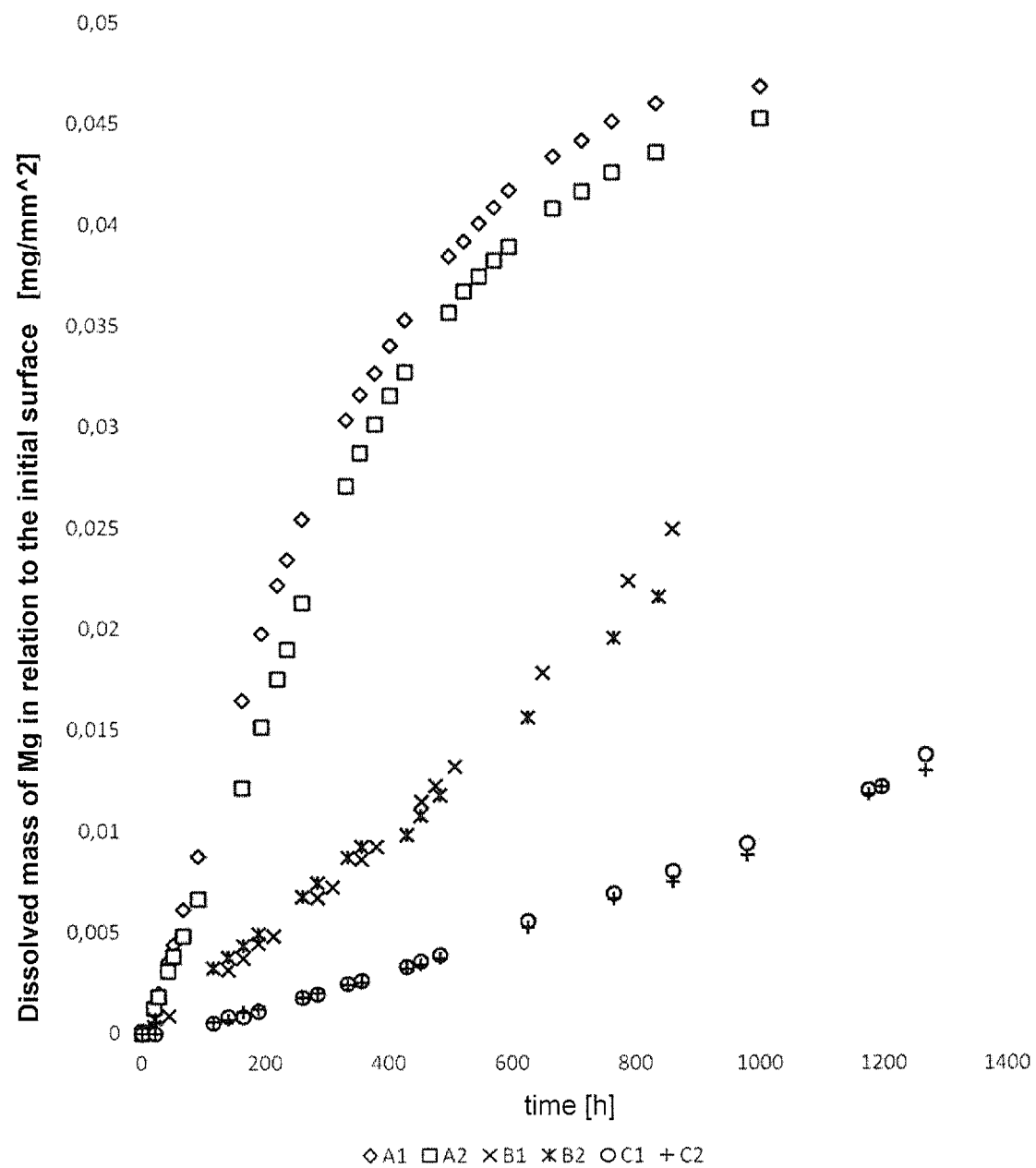

FIG. 23 shows the degradation rate of stents of magnesium alloy A (Mg10Dy1Nd1Zn0.2Zr) with and without an inorganic intermediate layer of magnesium fluoride and a further coating of poly-L-lactide (PLLA) with introduced drug (rapamycin, 1.4 µg/mm$^2$) in comparison to stents of alloy L37 and a coating of PLLA as well as introduced drug (sirolimus, 1.4 µg/mm$^2$).

Group A: Two stents (A1 and A2) of magnesium alloy L37 having a PLLA coating and an abluminal layer thickness of 6-12 µm.

Group B: Two stents (B1 and B2) of magnesium alloy A having a coating of 7.5 µm PLLA. The PLLA coating was applied by spraying method.

Group C: Two stents (C1 and 02) of magnesium alloy A having an inorganic coating (surface transformation) of magnesium fluoride and an overlying layer of 7.5 µm PLLA. The magnesium fluoride coating was applied as in example 13 group B. The PLLA coating was applied by spraying method.

EXAMPLES

Example 1: Production of the Alloys

The alloys were produced in the so-called permanent molt direct chill casting ("Tütengußverfahren"). This method serves for the production of precursors for the later extrusion and is characterized in that the material can be produced with a homogeneous microstructure and a homogeneous distribution of alloying elements in the ingot. Therefore it is exceptionally suitable to produce smaller quantities of high quality pins for the reshaping.

With this method, the magnesium alloys (L1, L2, . . . , L44) are melted in a smoothed steel crucible. As material of the crucible practically any nickel-free steel may be used. Graphite would be another possibility. All melting operations are carried out under inert gas. The temperatures of the molten bath are in the range of 660-740° C. Upon reaching the temperature of the molten bath, the alloying elements in form of pure elements or as master alloys were added. After addition of the alloying elements the melt was stirred mechanically. The stirring time depends on how long the elements or master alloys need to dissolve completely in the melt. After this preparation, the melt was transferred to a thin-walled coquille which was preheated to a temperature of 600° C. After a period of about 60 minutes, the coquille was immersed in a water bath having a temperature of 15-20° C. Due to the immersion the coquille completely solidified.

Prior to extrusion the surface of the cast part was turned to the diameter of the recipient of the extrusion press. In addition, prior to extrusion the casting pin was heated to a temperature of 250-500° C. and kept for 3-6 hours at this temperature to dissolve intermetallic phases or to homogenize segregations. This was followed by extrusion and the billet produced in this manner was cooled in air to room temperature. Wires were obtained which were then transformed into tubes.

The following alloys were prepared:

| Alloy L1: | |
|---|---|
| 87.8% by wt. | magnesium |
| 10.0% by wt. | dysprosium |
| 1.0% by wt. | neodymium |
| 1.0% by wt. | zinc |
| 0.2% by wt. | Impurities comprising Si, Ni, Fe, Cu and other metals and non-metals. |

| Alloy L2: | |
|---|---|
| 88.6% by wt. | magnesium |
| 10.0% by wt. | dysprosium |
| 1.0% by wt. | neodymium |
| 0.2% by wt. | zirconium |
| 0.2% by wt. | Impurities comprising Si, Ni, Fe, Cu and other metals and non-metals. |

| Alloy L3: | |
|---|---|
| 87.6% by wt. | magnesium |
| 10.0% by wt. | dysprosium |
| 1.0% by wt. | neodymium |
| 1.0% by wt. | zinc |
| 0.2% by wt. | zirconium |
| 0.2% by wt. | Impurities comprising Si, Ni, Fe, Cu and other metals and non-metals. |

-continued

Alloy L4:

| | |
|---|---|
| 89.7% by wt. | magnesium |
| 6.0% by wt. | dysprosium |
| 2.0% by wt. | neodymium |
| 2.0% by wt. | zinc |
| 0.3% by wt. | Impurities comprising Si, Ni, Fe, Cu and other metals and non-metals. |

Alloy L5:

| | |
|---|---|
| 90.7% by wt. | magnesium |
| 5.5% by wt. | dysprosium |
| 3.0% by wt. | neodymium |
| 0.5% by wt. | zirconium |
| 0.3% by wt. | Impurities comprising Si, Ni. Fe, Cu and other metals and non-metals. |

Alloy L6:

| | |
|---|---|
| 87.4% by wt. | magnesium |
| 8.0% by wt. | dysprosium |
| 2.2% by wt. | neodymium |
| 1.8% by wt. | zinc |
| 0.3% by wt. | zirconium |
| 0.3% by wt. | Impurities comprising Si, Ni, Fe, Cu and other metals and non-metals. |

Alloy L7:

| | |
|---|---|
| 82.7% by wt. | magnesium |
| 12.0% by wt. | dysprosium |
| 2.5% by wt. | neodymium |
| 2.5% by wt. | zinc |
| 0.3% by wt. | Impurities comprising Si, Ni, Fe, Cu and other metals and non-metals. |

Alloy L8:

| | |
|---|---|
| 85.2% by wt. | magnesium |
| 11.5% by wt. | dysprosium |
| 2.6% by wt. | neodymium |
| 0.4% by wt. | zirconium |
| 0.3% by wt. | Impurities comprising Si, Ni, Fe, Cu and other metals and non-metals. |

Alloy L9:

| | |
|---|---|
| 83.1% by wt. | magnesium |
| 15.2% by wt. | dysprosium |
| 1.2% by wt. | neodymium |
| 0.2% by wt. | zirconium |
| 0.3% by wt. | Impurities comprising Si, Ni, Fe, Cu and other metals and non-metals. |

Alloy L10:

| | |
|---|---|
| 88.9% by wt. | magnesium |
| 8.0% by wt. | dysprosium |
| 1.4% by wt. | neodymium |
| 1.2% by wt. | zinc |
| 0.2% by wt. | zirconium |
| 0.3% by wt. | Impurities comprising Si, Ni, Fe, Cu and other metals and non-metals. |

Alloy L11:

| | |
|---|---|
| 90.6% by wt. | magnesium |
| 8.0% by wt. | dysprosium |
| 1.0% by wt. | neodymium |
| 0.2% by wt. | zinc |
| 0.2% by wt. | zirconium |

Alloy L12:

| | |
|---|---|
| 89.3% by wt. | magnesium |
| 8.0% by wt. | dysprosium |
| 1.0% by wt. | neodymium |
| 1.0% by wt. | europium |
| 0.5% by wt. | zinc |
| 0.2% by wt. | zirconium |

Alloy L13:

| | |
|---|---|
| 86.0% by wt. | magnesium |
| 12.0% by wt. | dysprosium |
| 1.0% by wt. | neodymium |
| 0.8% by wt. | zinc |
| 0.2% by wt. | zirconium |

Alloy L14:

| | |
|---|---|
| 90.1% by wt. | magnesium |
| 6.0% by wt. | dysprosium |
| 1.0% by wt. | neodymium |
| 1.0% by wt. | europium |
| 1.5% by wt. | zinc |
| 0.4% by wt. | zirconium |

Alloy L15:

| | |
|---|---|
| 86.8% by wt. | magnesium |
| 10.0% by wt. | dysprosium |
| 1.0% by wt. | neodymium |
| 1.0% by wt. | europium |
| 1.0% by wt. | zinc |
| 0.2% by wt. | zirconium |

Alloy L16:

| | |
|---|---|
| 82.8% by wt. | magnesium |
| 14.0% by wt. | dysprosium |
| 0.5% by wt. | neodymium |
| v0.5% by wt. | europium |
| 2.0% by wt. | zinc |
| 0.2% by wt. | zirconium |

Alloy L17:

| | |
|---|---|
| 87.3% by wt. | magnesium |
| 10.0% by wt. | dysprosium |
| 1.5% by wt. | neodymium |
| 1.0% by wt. | zinc |
| 0.2% by wt. | zirconium |

Alloy L18:

| | |
|---|---|
| 87.45% by wt. | magnesium |
| 10.0% by wt. | dysprosium |
| 1.5% by wt. | neodymium |
| 1.0% by wt. | zinc |
| 0.05% by wt. | iron |

Alloy L19:

| | |
|---|---|
| 83.1% by wt. | magnesium |
| 15.0% by wt. | dysprosium |
| 0.9% by wt. | neodymium |
| 1.0% by wt. | zirconium |

Alloy L20:

| | |
|---|---|
| 95.0% by wt. | magnesium |
| 4.5% by wt. | dysprosium |
| 0.5% by wt. | neodymium |

Alloy L21:

| | |
|---|---|
| 83.7% by wt. | magnesium |
| 10.0% by wt. | dysprosium |
| 5.0% by wt. | neodymium |
| 1.0% by wt. | zinc |
| 0.3% by wt. | zirconium |

Alloy L22:

| | |
|---|---|
| 87.25% by wt. | magnesium |
| 10.0% by wt. | dysprosium |
| 1.5% by wt. | neodymium |
| 1.0% by wt. | zinc |
| 0.05% by wt. | iron |
| 0.2% by wt. | zirconium |

Alloy L23:

| | |
|---|---|
| 85.8% by wt. | magnesium |
| 12.0% by wt. | dysprosium |
| 1.0% by wt. | neodymium |
| 1.0% by wt. | zinc |
| 0.2% by wt. | zirconium |

Alloy L24:

| | |
|---|---|
| 82.1% by wt. | magnesium |
| 15.0% by wt. | dysprosium |
| 0.9% by wt. | neodymium |

|  |  |
|---|---|
| 1.0% by wt. | zinc |
| 1.0% by wt. | zirconium |

Alloy L25:

|  |  |
|---|---|
| 80.1% by wt. | magnesium |
| 19.0% by wt. | yttrium |
| 0.9% by wt | europium |

Alloy L26:

|  |  |
|---|---|
| 92.5% by wt. | magnesium |
| 5.0% by wt. | dysprosium |
| 2.5% by wt. | europium |

Alloy L27:

|  |  |
|---|---|
| 82.1% by wt. | magnesium |
| 15.5% by wt. | dysprosium |
| 1.2% by wt. | neodymium |
| 1.0% by wt. | zinc |
| 0.2% by wt. | zirconium |
| 0.001% by wt. | Impurities comprising Si, Ni, Fe, Cu and other metals and non-metals. |

Alloy L28:

|  |  |
|---|---|
| 82.0% by wt. | magnesium |
| 10.0% by wt. | gadolinium |
| 5.0% by wt. | neodymium |
| 1.0% by wt. | zinc |
| 2.0% by wt. | zirconium |

Alloy L29:

|  |  |
|---|---|
| 88.8% by wt. | magnesium |
| 6.0% by wt. | dysprosium |
| 4.0% by wt. | europium |
| 1.0% by wt. | zinc |
| 0.2% by wt. | zirconium |

Alloy L30:

|  |  |
|---|---|
| 89.8% by wt. | magnesium |
| 8.0% by wt. | dysprosium |
| 1.0% by wt. | europium |
| 1.0% by wt. | zinc |
| 0.2% by wt. | zirconium |

Alloy L31:

|  |  |
|---|---|
| 83.2% by wt. | magnesium |
| 15.0% by wt. | dysprosium |
| 0.4% by wt. | neodymium |
| 1.4% by wt. | europium |

Alloy L32:

|  |  |
|---|---|
| 87.4% by wt. | magnesium |
| 10.0% by wt. | dysprosium |
| 1.0% by wt. | europium |
| 0.5 by wt. | neodymium |
| 1.0% by wt. | zinc |
| 0.1% by wt. | zirconium |

Alloy L33:

|  |  |
|---|---|
| 87.0% by wt. | magnesium |
| 10.0% by wt. | dysprosium |
| 0.3% by wt. | europium |
| 1.5% by wt. | neodymium |
| 1.0% by wt. | zinc |
| 0.2% by wt. | zirconium |

Alloy L34:

|  |  |
|---|---|
| 86.0% by wt. | magnesium |
| 12.0% by wt. | dysprosium |
| 1.0% by wt. | europium |
| 0.8% by wt. | zinc |
| 0.2% by wt. | zirconium |

Alloy L35:

|  |  |
|---|---|
| 93.24% by wt. | magnesium |
| 0.35% by wt. | dysprosium |
| 2.05% by wt. | neodymium |
| 0.40% by wt. | gadolinium |
| 0.35% by wt. | zirconium |
| 3.60% by wt. | yttrium |
| 0.01% by wt. | erbium |

Alloy L36:

|  |  |
|---|---|
| 92.2% by wt. | magnesium |
| 0.5% by wt. | dysprosium |
| 0.5% by wt. | gadolinium |
| 2.2% by wt. | neodymium |
| 0.5% by wt. | zirconium |
| 4.1% by wt. | yttrium |

Alloy L37:

|  |  |
|---|---|
| 91.8% by wt. | magnesium |
| 0.7% by wt. | dysprosium |
| 0.7% by wt. | gadolinium |
| 2.0% by wt. | neodymium |
| 0.7% by wt. | zirconium |
| 4.1% by wt. | yttrium |

Alloy L38:

|  |  |
|---|---|
| 95.1% by wt. | magnesium |
| 1.2% by wt. | gadolinium |
| 2.5% by wt. | neodymium |
| 0.6% by wt. | zirconium |
| 0.3% by wt. | calcium |
| 0.3% by wt. | zinc |

Alloy L39:

|  |  |
|---|---|
| 96.9% by wt. | magnesium |
| 2.5% by wt. | neodymium |
| 0.4% by wt. | zirconium |
| 0.2% by wt. | zinc |

Alloy L40:

|  |  |
|---|---|
| 97.45% by wt. | magnesium |
| 0.75% by wt. | neodymium |
| 1.80% by wt. | manganese |

Alloy L41:

|  |  |
|---|---|
| 97.45% by wt. | magnesium |
| 0.75% by wt. | cerium |
| 1.80% by wt. | manganese |

Alloy L42:

|  |  |
|---|---|
| 90.0% by wt. | magnesium |
| 3.0% by wt. | gadolinium |
| 2.4% by wt. | yttrium |
| 0.4% by wt. | zirvonium |
| 4.2% by wt. | scandium |

Alloy L43:

|  |  |
|---|---|
| 90.0% by wt. | magnesium |
| 3.0% by wt. | neodymium |
| 2.4% by wt. | yttrium |
| 0.4% by wt. | zirconium |
| 5.2% by wt. | scandium |
| 2.0% by wt. | indium |

Alloy L44:

|  |  |
|---|---|
| 96.0% by wt. | magnesium |
| 4.0% by wt. | lithium |

The alloys L1 to L44 were produced with an inorganic magnesium fluoride coating on the one hand and with an inorganic magnesium fluoride coating and an organic parylene C coating on the other hand. All alloys L1 to L44 show a decelerated dissolution kinetics of the inorganic magnesium fluoride coated stents compared to the uncoated stents. Furthermore, stents having an inorganic magnesium fluoride coating and an organic parylene C coating show once again decelerated dissolution kinetics compared to stents having an inorganic magnesium fluoride coating and without an organic parylene C coating. In addition, the dissolution kinetics is significantly decelerated compared to a stent having an organic parylene C coating only. The presence of an antirestenotic active agent in or on the organic parylene C coating does not appear to have a noticeable effect on the resorption kinetics. The following examples exemplarily describe the production and investigation of such stents.

Example 2: Tube Production

From the alloys L1 to L10 according to example 1 extruded wires were prepared. In these extruded wires, a precision drill-hole is introduced in longitudinal direction, which already co-determines the wall thickness of the later stents. By several forming steps, a tube of predetermined diameter and certain wall thickness is made. Between the individual forming steps repeating heat treatment takes place.

Example 3: Stent Production

A tube produced according to Example 2 is fixed into an adapter in the laser machine. A pulsed solid-state laser (FKL) cuts the contours of the stent design out of the tube. The laser cutting is performed under an inert gas atmosphere.

The stent design is stored in a NC program (numerical control). This predefines the traverse path (cutting pattern) to the laser, after which the tube is structured. By the laser beam cutting burr formation occurs, especially on the inside of the tube, along the entire cutting contour. This can cause that off-cuts and cut-outs remain adhered to the contour after the termination of the cutting process. The off-cuts and cut-outs are mechanically removed and the stent is cleaned from manufacturing residues. In a first optical visual control an inspection of the cutting contour is performed.

In the following, the stent is electrochemically polished. The stent is anodically connected and immersed in an acid bath. Via a cathode fixed in the bath, an electric circuit is closed. The electric circuit is maintained for several minutes. The electropolishing is an inverted galvanic process where material is removed in a controlled manner from the surface of the anodically connected component. Due to the method ablation preferably takes place at sharp corners and edges. The stent obtains a smooth surface and rounded edges along the contours. After polishing, the stent is cleaned and freed from acid residues. During the final cleaning all still remaining manufacturing residues are removed from the stent surface. In a last optical visual control the stent geometry is measured and the surface is tested on purity Example 4: Determination of Grain Size The counting of the grain size was made using linear intercept method. Grains which are only half cut at the end of the line were hereby counted as half grains. The magnification was selected such that at least 50 grains were cut by the grid. At least 5 sites with a total of at least 250 points of intersection were evaluated on the sample.

Example 5: Determination of the Corrosion Rate

At room temperature, the corrosion rates of various alloys were determined for a period of 3 days in a physiological saline solution (see Table 1). An alloy was tested containing 90.8% by wt. Mg, 8% by wt. Dy, 1% by wt. Nd and 0.2% by wt. Zr, an alloy containing 89.8% by wt. Mg, 8% by wt. Dy, 1% by wt. Nd, 1% by wt. Eu and 0.2% by wt. Zr, an alloy containing 86.8% by wt. Mg, 12% by wt. Dy, 1% by wt. Nd, and 0.2% by wt. Zr, and an alloy containing 87.8% by wt. Mg, 10% by wt. Dy, 1% by wt. Nd, 1% by wt. Eu and 0.2% by wt. Zr. In addition alloys containing 1.0% by wt. neodymium, 1.0% by wt. zinc, 0.2% by wt. zirconium, between 5 and 20% dysprosium and the balance magnesium (see FIG. 7) were tested. Corrosion products were removed by immersion of the samples in chromic acid (180 WO for 20 min at room temperature. The average corrosion rate was calculated in millimeter per year by the following equation:

$$CR = \frac{8.76 \times 10^4 \times \Delta g}{A \cdot t \cdot \rho}$$

TABLE 1

Corrosion rate of alloys according to the invention, measured over 3 days at room temperature, and in 0.9% NaCl; the specification of the components of the alloys are in % by weight and Mg as major component adds always up to 100% of the alloy. The alloys were tested after casting, without heat treatment, the average values and standard deviations of the various alloys are listed.

| No. | Composition | Corrosion rate (mm/year) |
| --- | --- | --- |
| L11 | Mg8Dy1Nd0.2Zn0.2Zr | 9.25 ± 0.38 |
| L15 | Mg10Dy1Nd1Eu1Zn0.2Zr | 0.81 ± 0.06 |
| L23 | Mg12Dy1Nc1Zn0.2Zr | 2.94 ± 1.88 |
| L16 | Mg8Dy1Nd1Eu1Zn0.1Zr | 4.9 ± 1.62 |
| L14 | Mg6Dy1Nd1Eu1.5Zn0.4Zr | 9.56 ± 0.29 |
| L16 | Mg14Dy0.5Nd0.5Eu2Zn0.2Zr | 1.25 ± 0.12 |
| L18 | Mg10Dy1.5Nd1Zn0.05Fe | 12.41 ± 2.16 |
| L20 | Mg4.5Dy0.5Nd | 25.56 ± 2.34 |
| L24 | Mg15Dy0.9Nd1Zr1Zn | 2.98 ± 1.78 |
| L25 | Mg20Y0.9Eu | 44.71 ± 3.22 |
| L28 | My20Gd5Nd1Zn2Zr | 38.96 ± 1.34 |
| L30 | Mg8Dy1Eu1Zn0.2Zr | 3.88 ± 1.87 |
| L22 | Mg10Dy1.5Nd1Zn0.2Zr0.05Fe | 4.47 ± 2.11 |
| L34 | Mg12Dy1Eu0.8Zn0.2Zr | 5.46 ± 1.22 |
| L29 | Mg6Dy4Eu1Zn0.2Zr | 12.20 ± 11.36 |
| L33 | Mg10Dy0.3Eu1.5Nd1Zn0.2Zr | 1.25 ± 0.67 |
| L26 | Mg5Dy2.5Eu | 23.56 ± 1.56 |
| L31 | Mg25Dy0.4Nd1.4Eu | 48.71 ± 1.87 |

Example 6: Mechanical Characteristics of the Alloys

The alloys and cast parts were produced according to Example 1 and extruded. The heat treatment T4 was carried out at 510° C. over 8 hours and eventually afterwards the heat treatment T6 at 200° C. over a period of time of 72 hours. After the T4 heat treatment the samples were immediately quenched in water. All samples were taken from the same position of the blocks.

The tensile tests were performed at room temperature according to DIN EN 10002-1 (corresponds to ISO 6892 and ASTM E8) and pressure tests were performed at room temperature according to DIN 50106 (corresponds to ISO 604 and ASTM D695). At least 3 samples were tested for each value. The tensile strength was calculated in terms of the maximum tensile force achieved in the tensile test in regard to the initial cross-section of the sample.

TABLE 2

Mechanical characteristic values of inventive alloys. Alloys were tested as a sample after the extrusion (ST, without heat treatment) and after different heat treatments, T4 (solution annealed), and T6 (a further heat treatment after T4, also known as "aging"). The information on the components of the alloys are given in % by wt. and Mg as the main component always fills the quantity up to 100% of the alloy. SD means standard deviation of the average values, which are indicated in the left column (n = 3).

|    | Composition | Yield strength (MPa) | SD | Tensile strength (MPa) | SD | elongation at break (%) | SD |
|----|---|---|---|---|---|---|---|
| ST | Mg8Dy1Nd0.2Zn0.2Zr | 107.33 | 1.8 | 208.5 | 0.85 | 28.12 | 3.41 |
| T4 |  | 87.54 | 0.46 | 176.84 | 2.03 | 18.83 | 1.79 |
| T6 |  | 97.95 | 1.67 | 194.11 | 1.1 | 19.33 | 0.68 |
| ST | Mg10Dy1Nd1Eu1Zn0.2Zr | 169.30 | 0.74 | 283.89 | 0.68 | 16.96 | 1 |
| T4 |  | 151.97 | 1.77 | 259.50 | 2.57 | 18.02 | 0.29 |
| T6 |  | 159.23 | 2.23 | 275.55 | 1.78 | 18.15 | 2.77 |
| ST | Mg12Dy1Nd1 Zn0.2Zr | 126.07 | 11.8 | 226.04 | 0.35 | 28.55 | 0.08 |
| T4 |  | 98.38 | 0.43 | 188.45 | 0.5 | 20.47 | 0.91 |
| T6 |  | 114.6 | 1.69 | 205.2 | 1.25 | 17.99 | 0.79 |
| ST | Mg8Dy1Nd1Eu1Zn0.1Zr | 132.24 | 1.1 | 227.21 | 0.59 | 19.75 | 1.11 |
| T4 |  | 114.93 | 1.25 | 210.73 | 1.51 | 20.89 | 1.01 |
| T6 |  | 136.77 | 1.77 | 223.28 | 0.67 | 23.64 | 2.01 |
| ST | Mg6Dy1Nd1Eu1.5Zn0.4Zr | 128.14 | 8.02 | 202.74 | 2.91 | 24.62 | 2.09 |
| T4 |  | 80.97 | 2.27 | 173.47 | 2.02 | 23.78 | 3.52 |
| T6 |  | 84.26 | 2.57 | 178.26 | 1.35 | 26.32 | 2.5 |
| ST | Mg14Dy0.5Nd0.5Eu2Zn0.2Zr | 165.64 | 4.95 | 218.17 | 3.07 | 18.9 | 1.14 |
| T4 |  | 110.78 | 1.87 | 201.28 | 1.19 | 21.62 | 1.07 |
| T6 |  | 153.15 | 3.55 | 264.09 | 0.71 | 17.66 | 1.33 |
| ST | Mg10Dy1.5Nd1Zn0.05Fe | 145.46 | 3.55 | 237.21 | 0.75 | 28.9 | 1.73 |
| T4 |  | 102.78 | 4.38 | 193.36 | 5.84 | 27.57 | 0.88 |
| T6 |  | 108.84 | 1.68 | 200.16 | 2.97 | 25.56 | 1.66 |
| ST | Mg4.5Dy0.5Nd | 68.39 | 7.9 | 208.48 | 2.03 | 28.4 | 0.72 |
| T4 |  | 60.31 | 1.71 | 179.04 | 0.83 | 23.17 | 0.38 |
| T6 |  | 75.13 | 1.32 | 250.34 | 1.42 | 13.34 | 0.74 |
| ST | Mg15Dy0.9Nd1Zr1Zn | 136.93 | 1.6 | 227.07 | 0.42 | 22.9 | 3.03 |
| T4 |  | 95.79 | 1.94 | 200.59 | 2.59 | 21.57 | 0.34 |
| T6 |  | 112.09 | 0.41 | 206.11 | 0.19 | 19.56 | 0.66 |
| ST | Mg20Y0.9Eu | 159.75 | 11.99 | 238.55 | 0.76 | 11.57 | 0.58 |
| T4 |  | 123.19 | 4.83 | 214 | 1.42 | 19.62 | 2.74 |
| T6 |  | 144.08 | 4.37 | 220.2 | 2.58 | 15.58 | 0.94 |
| ST | Mg20Gd5Nd1Zn2Zr | 297.75 | 8.12 | 338.53 | 5.67 | 1.53 | 0.27 |
| T4 |  | 195.82 | 15.65 | 276.89 | 0.91 | 6.58 | 0.95 |
| T6 |  | 327.07 | 17.57 | 378.45 | 14.94 | 0.76 | 0.32 |
| ST | Mg8Dy1Eu1Zn0.2Zr | 112.85 | 1.15 | 198.9 | 0.43 | 24.07 | 1.05 |
| T4 |  | 93.5 | 1.01 | 182.38 | 0.91 | 24.02 | 0.81 |
| T6 |  | 99 | 0.99 | 185.7 | 0.4 | 25.9 | 1.16 |
| ST | Mg10Dy1.5Nd1Zn0.2Zr0.05Fe | 127.8 | 4.62 | 215.84 | 1 | 19.39 | 1.4 |
| T4 |  | 96.72 | 4.02 | 192.99 | 2.87 | 25.92 | 0.98 |
| T6 |  | 112.34 | 3.1 | 201.35 | 2.18 | 24.44 | 1.91 |
| ST | Mg12Dy1Eu0.8Zn0.2Zr | 182.30 | 1.52 | 293.62 | 1.37 | 22.39 | 2.06 |
| T4 |  | 164.48 | 1.44 | 268.66 | 0.45 | 23.70 | 1.63 |
| T6 |  | 172.34 | 2.12 | 271.35 | 1.82 | 23.34 | 1.79 |
| ST | Mg6Dy4Eu1Zn0.2Zr | 115.09 | 1.39 | 208.3 | 1.68 | 2.30 | 0.51 |
| T4 |  | 97.55 | 0.74 | 189.39 | 0.84 | 4.78 | 1.71 |
| T6 |  | 112.58 | 1.59 | 196.71 | 2.31 | 3.41 | 0.69 |
| ST | Mg10Dy0.3Eu1.5Nd1Zn0.2Zr | 168.54 | 6.15 | 277.11 | 2.09 | 16.46 | 2.33 |
| T4 |  | 136.36 | 5.11 | 244.89 | 2.37 | 20.67 | 3.15 |
| T6 |  | 152.22 | 2.42 | 253.91 | 2.33 | 18.56 | 1.87 |
| ST | Mg5Dy2.5Eu | 74.25 | 1.63 | 283.50 | 1.44 | 21.60 | 1.27 |
| T4 |  | 60.19 | 1.69 | 264.46 | 0.91 | 23.16 | 1.43 |
| T6 |  | 65.38 | 1.83 | 266.64 | 1.36 | 22.85 | 1.64 |
| ST | Mg25Dy0.4Nd1.4Eu | 106.34 | 2.98 | 211.15 | 1.65 | 18.90 | 1.55 |
| T4 |  | 88.74 | 1.69 | 178.56 | 2.03 | 20.03 | 2.31 |
| T6 |  | 94.21 | 1.34 | 191.25 | 1.67 | 19.54 | 1.99 |

Example 7: Animal Study 8 stents produced according to Example 2 and 3 were implanted in the coronary arteries of 4 domestic pigs. The stents had a diameter of 3.0 mm and a length of 14 mm (length of the catheter balloon 15 mm), were uncoated and were made of an alloy of the following composition:

| | |
|---|---|
| 87.8 Gew.-% | magnesium |
| 10.0 Gew.-% | dysprosium |
| 1.0 Gew.-% | neodymium |
| 1.0 Gew.-% | zinc |
| 0.2 Gew.-% | zirconium |

The "follow up" period for all 4 animals was 4 weeks after implantation. One day prior to stent implantation a single dose of clopidogrel (300 mg) and aspirin (250 mg) were administered orally to the pigs. Under general anaesthesia, an access to the femoral artery was surgically placed and a bolus of heparin sodium (10 000 IU) was administered. A 6F coronary guiding catheter was inserted through the femoral artery into the aorta descendens. Coronary angiography was performed by using hand injection of a non-ionic contrast agent to obtain the anatomic conditions for the performance of the procedure.

The stents were implanted in the ramus interventricularis anterior (RIVA or LAD) and ramus circumflexus (RCX or LCx). Dilatation pressure of the balloon for stent implantation was chosen to achieve a stent balloon to artery ratio of 1.2 to 1. The pigs were then allowed to recover. During the entire 4 weeks "follow up", the animals daily received orally a dose of 100 mg aspirin and 75 mg clopidogrel per 30 g body weight.

After 4 weeks "follow up", control angiography and optical coherence tomography (OCT) were performed.

In the OCT procedure a 0.014 inch guidewire is inserted into the LAD and the LCx and guided through the implanted stents into the distal part of the vessel. An OCT catheter was subsequently advanced distal to the stent over the guide wire. The injection pump was turned on to inject contrast agent at a speed of 3.0 ml/s and thus to temporarily displace the blood. The entire length of the lesion was imaged by using an automatic pullback device at 10 mm/s. After imaging, the OCT catheter was withdrawn, and the images were saved. The animals were then euthanized, and the coronary arteries were explanted.

The explanted arteries were fixed by perfusion with a pressure of 100 mmHg for 1 h using 7% formalin. The stents were processed for light microscopy. For light microscopy, the arteries were cut into 3 sections: proximal, mid and distal stent segments. These segments were embedded in methyl metacrylate (Technovit 9100). The segments of the stented arteries were cut into 4-6 μm slices using a rotary microtome, and stained with hematoxylin and eosin.

As part of the analysis details of the study were listed such as the stent position, the dilatation pressure and the dilatation time, as well as any complications during the implantation.

Quantitative Coronary Angioplasty (QCA)

A QCA was performed to analyze the in-stent restenosis. Thereby, the following parameters were determined: vessel diameter pre and post stent implantation, minimal lumen diameter (MLD) after stent implantation and at follow up and the diameter of a reference segment (RD) at follow up. Here, the minimal lumen diameter is the smallest absolute internal vessel diameter in the region of the dilated segment, averaged from the two orthogonal projection planes. LLL (late lumen loss) is a measure of the narrowing of the lumen by neointimal hyperplasia. The lumen diameter is measured directly after the intervention and 4 weeks post interventional, the difference between the two is given as LLL. The length of the stenosed or dilated segment was monitored and the stenosis in percent was calculated.

Optical Coherence Tomography (OCT)

The images of the optical coherence tomography were analyzed in accordance with the relevant guideline (JACC, 2012). The following parameters were gathered: stent malapposition, stent strut coverage, tissue protrusion, the arterial dissection, thrombosis. The quantitative analysis of the OCT images comprises the minimal and maximal stent diameter and the lumen area. The following parameters were calculated: maximal area stenosis and stent symmetry. For the quantitative analysis the "worst" cross-section per test group was determined.

Calculation of Area Stenosis (% AS):

$$\% \text{ AS} = \text{intimal area}/\text{stent area} = (\text{stent area} - \text{lumen area})/\text{stent area}$$

Calculation of Stent Symmetry:

$$\text{Stent symmetry} = (\text{maximal stent diameter} - \text{minimal stent diameter})/\text{maximal stent diameter}$$

Fibrin deposition, degree of inflammation (intima and adventitia), haemorrhages and necrosis were analyzed in accordance with the published guidelines.

Histomorphometry

Histomorphometry was carried out by using computer-assisted planimetry. The lumen, the area of the internal elastic lamina and external elastic lamina and the maximum neointimal thickness were measured. The extension of the neointima and the tunica media as well as the percentage of stenosis was calculated.

Results

The dilatation pressure used was between 12 and 18 atm. The balloon inflation took 30 sec. In general, the handling of the stents and balloons were excellent; very good pushability and very short deflation time was recorded.

TABLE 3

Results of the quantitative coronary angioplasty (QCA), the average values and standard deviations (SD); MLD = minimal lumen diameter, RD = diameter of a reference segment, % DS = percentage of diameter of stenosis, FUP = follow-up, LLL = late lumen loss

| | Pre-MLD (mm) | Post-MLD (mm) | FUP-MLD mm | FUP-RD (mm) | FUP-% DS (%) | LLL mm |
|---|---|---|---|---|---|---|
| Uncoated Stents (BMS) | 2.68 | 2.93 | 2.08 | 2.92 | 28.75 | 0.85 |
| SD | 0.11 | 0.07 | 0.53 | 0.20 | 16.79 | 0.47 |

TABLE 4

Qualitative analysis of the optical coherence tomography (OCT) per implanted stent

| animal No. | artery | group | stent-malapposition | tissue protrusion | in-stent thrombosis | in-stent dissection | edge dissection | endothelial-ization |
|---|---|---|---|---|---|---|---|---|
| MEKO-1 | LAD | BMS | 0 | 0 | 0 | 0 | 0 | complete |
| MEKO-1 | LCx | BMS | 0 | 0 | 0 | 0 | 0 | incomplete |
| MEKO-2 | LAD | BMS | 0 | 0 | 0 | 0 | 0 | complete |
| MEKO-2 | LCx | BMS | 0 | 0 | 0 | 0 | 0 | complete |
| MEKO-3 | LAD | BMS | 0 | 0 | 0 | 0 | 0 | complete |
| MEKO-3 | LCx | BMS | 0 | 0 | 0 | 0 | 0 | complete |
| MEKO-4 | LAD | BMS | 0 | 0 | 0 | 0 | 0 | complete |
| MEKO-4 | LCx | BMS | 0 | 0 | 0 | 0 | 0 | complete |

TABLE 5

Qualitative analysis of the optical coherence tomography (OCT) in relation to the number of implanted stents (n = 8; all values in percent)

|  | stent-malapposition | tissue protrusion | in-stent thrombosis | in-stent dissection | edge dissection | endothelial-ization |
|---|---|---|---|---|---|---|
| BMS n = 8 | 0 | 0 | 0 | 0 | 0 | 87.5 |

From Tables 3, 4 and 5 can be obtained that on the one hand none of the tested complications occurred when using a stent according to the invention and, on the other hand, that an endothelialization was almost always completed after 4 weeks, which meant that the increased risk of in-stent thrombosis due to not completed endothelialization or inflammation reactions was no longer present. Comparable results were also obtained with stents of a magnesium alloy containing europium instead of neodymium.

TABLE 6

Further results of the qualitative analysis of the optical coherence tomography (OCT), listed are the average values and standard deviations (SD).

| Type | min. stent diameter (mm) | max. stent diameter r (mm) | stent area (mm$^2$) | lumen area (mm$^2$) | % AS (%) | stent symmetry |
|---|---|---|---|---|---|---|
| BMS n = 8 | 2.54 | 2.72 | 7.58 | 5.08 | 34.0 | 0.07 |
| SD | 0.34 | 0.35 | 1.80 | 1.69 | 13.2 | 0.02 |

Example 8: Coating of Stents According to the Invention by Surface Transformations Magnesium Fluoride Layer (MgF$_2$)

For generation of this layer, the stent was immersed in 40% hydrofluoric acid (50 ml) for 24 hours at a temperature below 50° C. The container with the hydrofluoric acid in turn was immersed in a heated water bath to ensure the temperature of 50° C. After the 24 hours, the stent was removed and rinsed with deionized water and then dried in air.

Magnesium Fluoride Layer (MgF2) and Annealing

For generation of this layer, the stent was immersed in 40% hydrofluoric acid (50 ml) for 24 hours at a temperature below 50° C. The container with the hydrofluoric acid in turn was immersed in a heated water bath to ensure the temperature of 50° C. After the 24 hours, the stent was removed and rinsed with deionized water and then dried in air. The stent was then annealed in air for 24.5 hours.

Magnesium Fluoride Layer (MgF$_2$)

For generation of this layer, the stent was placed in an oxygen plasma for 1.5 hours. The plasma is supposed to oxidize the surface of the stent to form a MgO layer. The stent was then immersed in a 40% hydrofluoric acid (50 ml) for 24 hours at a temperature below 50° C. The container with the hydrofluoric acid in turn was immersed in a heated water bath to ensure the temperature of 50° C. After the 24 hours, the stent was removed and rinsed with deionized water and then dried in air.

Magnesium Fluoride Layer (MgF$_2$) with an Ammonium Fluoride Solution

For generation of this layer, the stent was immersed in a 10% ammonium fluoride solution (50 ml) for 24 hours below 50° C. The container with the solution in turn was immersed in a heated water bath to ensure the temperature of 50° C. After the 24 hours, the stent was removed and rinsed with deionized water and then dried in air. The measured values of dissolved magnesium over the time of a stent of sample B are shown.

Example 9: Degradation Test of Stents Subjected to Oxygen Ion Implantation

The coated stents of example 8 were examined in a degradation test.

The degradation tests were carried out with a degradation test machine (DTM) from MeKo Laserstrahl-Materialbearbeitungen e.K. The DTM is equipped with a peristaltic pump, a temperature sensor, heating system, flow sensor and a camera system.

The coronary stent used for the tests was manufactured by MeKo Laserstrahl-Materialbearbeitungen e.K. The stent material is magnesium alloy A (Mg10Dy1Nd1Zn0.2Zr).

The stent of the magnesium alloy A was subjected to an oxygen ion implantation. Oxygen ions are shot into the surface, where they should modify the surface or form a magnesium oxide layer. The mass of the stent after ion implantation was 5.97 mg (measured with the Sartorius CPA225D precision scale (Serial Number: 31906122)).

The filling quantity of the test fluid PBS (phosphate buffered saline) was 300 ml. The temperature of the fluid is maintained at 37±2° C. The flow rate [ml/min], the temperature of the fluid [° C.] and the digital images [1 image/min] are continuously recorded and stored by the system. The test fluid PBS consists of: 8.0 [g/l] NaCl, 0.2 [g/l] KCl, 1.15 [g/l] $Na_2HPO_4$ and 0.2 [g/l] $KH_2PO_4$.

The pH values were measured at different times by using the Mettler Toledo SevenGo SG2, Serial No. B426752831 measuring instrument and the Mettler Toledo InLab 413 SG/2m IP67, No. 51340288 measuring probe.

The pH values were periodically adjusted to 7.40 by adding HCl or NaOH. Thus, these could be kept within the limits of 7.2 to 7.6.

Photometry Measurement

The photometry measurement for the concentration measurement of the magnesium concentrations over the test period was carried out with a spectrophotometer.

The measurement results are shown graphically in FIG. 3. Compared to the average of three uncoated stents of magnesium alloy A (BMS) the degradation was also shown to be decelerated. Initially (within the first two hours), about the same amount of magnesium dissolved in the $O_2$ ion implanted as well as in the BMS, after that less magnesium dissolved in the ion implanted. Furthermore, in comparison to the hydrofluoric acid treated stent a faster dissolution is shown for the ion-implanted stents.

The comparison of the camera images in FIG. 4 shows that the oxygen implantation (sample B, first line) makes the stent significantly more durable in the corrosive environment (PBS) than the untreated stent (sample A, second line). Also, the stent having $MgF_2$ surface (sample C, third line) degraded significantly slower than the untreated stent.

Camera Shots

The images in FIG. 4 confirm the photometric measurements. However, it cannot be derived from the pure measured values that the $O_2$ ion-implanted stent withstands so much longer before the first strut breaks (bare metal stent: after 2 hours; $MgF_2$ coated stent: 12 hours; $O_2$ ion-implanted stent: 25 hours) and until the stent is completely degraded in front of the camera.

One explanation could be that up to the protective oxide layer (magnesium oxide), which is generated by the implanted oxygen ions, the magnesium dissolves as quickly as in case of an untreated stent. Then, at the point the magnesium oxide layer has been reached, the magnesium dissolves much more slowly. Furthermore, the magnesium seems to dissolve much more homogeneously, i.e. over the entire stent surface. The magnesium oxide layer of a bare metal stent is probably much thinner. It constitutes only a kind of barrier for the first two hours. Subsequently, more and more struts break at arbitrary points.

The fluoride layer inhibits the degradation the strongest in the first time (up to approx. 25 hours). However, earlier strut fractures still occur. The magnesium fluoride layer is very brittle and can partially break when dilating the stent. At these sites the stent degrades faster.

Conclusion

In case of oxygen ion-implanted stents, magnesium goes into solution from the very beginning. However, this seems to be more homogeneous as the first strut fractures occur much later (after about 25 hours) than in case of comparable stents. For comparison: First strut fractures in bare metal stents occur after about 2 hours, in hydrofluoric acid treated stents after about 11-18 hours.

Example 10: Degradation Tests of Stents after Different Surface Treatments 3 stents of magnesium alloy A (Mg10Dy1 Nd1Zn0.2Zr) were treated in three solutions (38-40% HF solution, 10% $Na_2CO_3$ solution and 10% $Na_3PO_4$ solution).

Treatment in 38-40% hydrofluoric acid was performed as follows:

The 3 stents were each placed in a plastic container. The plastic containers with lids (made of PP) were each filled with 50 ml 38-40% hydrofluoric acid and then placed in a tempered water bath at a temperature of 50° C. The water was heated to 50° C. in a glass reservoir by a heating plate and kept at 50° C. during the treatment process. An agitator in the reservoir made it possible to easily move the plastic containers in the water bath. After 24 hours, the plastic containers were removed from the water bath.

The stents in turn were removed from the hydrofluoric acid, rinsed with deionized water, dried with compressed air and packed in a glass tube.

The treatment in 10% sodium carbonate ($Na_2CO_3$) solution was carried out as follows:

First, sodium carbonate ($Na_2CO_3$) was dissolved in deionized water to give a 10% solution. The pH was adjusted by adding sodium hydroxide (NaOH). The stents were then each placed in a plastic container with a lid (made of PP) and each filled with 50 ml of 10% $Na_2CO_3$ solution. The containers were also placed in a tempered water bath at a temperature of 50° C. and kept there for 26 hours. The further procedure is identical to the hydrofluoric acid treatment (see above).

The treatment in 10% sodium phosphate ($Na_3PO_4$) solution was carried out as follows:

First, sodium phosphate ($Na_3PO_4$) was dissolved in deionized water to give a 10% solution. The stents were then each placed in a plastic container with a lid (made of PP) and each filled with 50 ml of 10% $Na_3PO_4$ solution. The containers were also placed in a tempered water bath at 50° C. and kept there for 24 hours. The further procedure is identical to the hydrofluoric acid treatment (see above).

The degradation measurements were carried out as in example 9.

Photometric Measurement

The results of the photometric measurement are shown graphically in FIG. 5. The differences in the degradation rate in case of $MgCO_3$ or $Mg_3(PO_4)_2$ samples are rather small. A clear delay of the degradation could only be achieved by hydrofluoric acid treatment at 50° C. for 24 hours ($MgF_2$ samples).

It is also noticeable that the values of the dissolved masses of magnesium among each other in case of hydrofluoric acid treatment do not have a large scatter.

The samples treated in sodium phosphate show the strongest differences of the degradation rates among each other, which could already be assumed by examination of the microscope images before the beginning of degradation.

Camera Shots

FIG. 6 illustrates the degradation very well. Each line contains three camera shots of the same sample.

In principle, the observations from the photometric measurements are confirmed. The stent with hydrofluoric acid treatment (first line) dissolves much more slowly than the other stents. In this stent, the first strut fracture occurs after 11 to 19 hours. A sample of the $Mg_3(PO_4)_2$ group dissolved completely in front of the camera after 6 hours, which confirms the photometric measurement of this sample.

Conclusion

A significant improvement of the degradation rate could only be achieved with hydrofluoric acid treatment. The time until the first strut break could be increased at least fivefold (from 2 h to 11-19 h). The course of degradation of $MgF_2$ surface-treated stents is also better for maintaining the radial strength of the stent. Initially, the stents degrade slowly (compared to bare metal stents and $MgCO_3$ and $MgPO_4$ modifications).

The comparison of the images shows that due to the magnesium fluoride surface transformation (sample B, first line) the stent is significantly more durable in the corrosive environment (PBS) than the untreated stent (sample D, fourth line). The magnesium phosphate and magnesium carbonate layer does not seem to significantly slow down degradation, which is consistent with the photometric measurements of dissolved masses of magnesium over time (FIG. 5).

Example 11: Degradation Experiments of $MgF_2$ Coating, Produced with Ammonium Fluoride and Hydrofluoric Acid, Each with a Different Exposure Time The stents were treated in different ways (specifications are based on FIG. 10).

Sample A and C: Two stents of magnesium alloy A (Mg10Dy1Nd1Zn0.2Zr) were each placed in a plastic container. The plastic containers with lids (made of PP) were each filled with 50 ml 38-40% hydrofluoric acid and then placed in a tempered water bath at a temperature of 50° C. The water was heated to 50° C. in a glass reservoir by a heating plate and kept at 50° C. during the treatment process. An agitator in the reservoir allows to easily move the plastic containers in the water bath. After 5 hours (sample C) or after 24 hours (sample A), the plastic containers were removed from the water bath. The stents in turn were removed from the hydrofluoric acid, rinsed with deionized water, dried with compressed air, and packed in a glass tube.

Sample B and D: Ammonium fluoride ($NH_4F$) was first dissolved in deionized water to give a 10% solution. Then, the two stents of magnesium alloy A (Mg10Dy1Nd1Zn0.2Zr) were each placed in a plastic container with lid (made of PP) and each filled with 50 ml of 10% $NH_4F$ solution. The containers were also placed in a tempered water bath at 50° C. and kept there for 5 hours (sample D) or 24 hours (sample B). The further procedure is identical to the hydrofluoric acid treatment (see samples A and C).

Stents of magnesium alloy A were treated in two different solutions (40% hydrofluoric acid and 10% ammonium fluoride) at 50° C. for 5 and 24 hours respectively. The stents were stored in a closed plastic container and swivelled by means of a stirring plate.

Subsequently, the composition of the surface coating was determined with the scanning electron microscope (SEM) "Tescan Vega 3" with integrated EDX from Thermo Fischer. The surface layer was examined under an electron acceleration voltage of 15 kV.

Stents having the following surface coatings were obtained:

5 h with ammonium fluoride: 48.8% F, 32.4% Mg, 11.0% 0, 7.7% C 24 h with ammonium fluoride: 50.3% F, 24.5% Mg, 19.7% 0, 0.5% Dy, 5.1% C 5 h with hydrofluoric acid: 54.7% F, 24.6% Mg, 10.2% 0, 10.6% C 24 h with hydrofluoric acid: 57.8% F, 24.0% Mg, 9.5% 0, 8.8% C The degradation measurements were carried out as in example 9.

The results are shown in FIG. 10. The stent which was treated for 24 hours in hydrofluoric acid shows the slowest degradation in this comparison. In the first 10 hours only half amount of magnesium is dissolved as in the stent which was only treated for 5 hours. Stents treated with ammonium fluoride do not differ significantly from each other. In comparison to the 24-hour hydrofluoric acid treatment, the other treatments are less effective in decelerating the degradation.

Example 12: Degradation Tests with Ion-Implanted Stents

During ion implantation, ions (oxygen, fluorine and carbon) were introduced into stents of magnesium alloy A (Mg10Dy1Nd1Zn0.2Zr). The corresponding ions, which are generated by an ion source, are strongly accelerated by an electric field and shot into the substrate (in this case the stent) with high energy. In this way, a protective layer is supposed to be created to protect the stent from degradation.

For the degradation experiments, stents were bombarded with carbon, oxygen and fluorine ions. For the degradation comparison, the stents were divided into three groups. For the test, the same design and substrate material (magnesium alloy A) was always used for the stents. All stents were laser cut, heat treated and electropolished. The group specifications refer to FIG. 11:

Sample A: 3 stents having an oxygen implantation ($2 \times 10^{17}$ O-ions per $cm^2$)

Sample B: 2 stents having a fluorine implantation ($6 \times 10^{16}$ F ions per $cm^2$)

Sample C: 3 stents without any coating (reference)

Photometric Measurement

The degradation measurements were carried out as in example 9 and are shown in FIG. 11. The mean values (for group A: mean value of 3 measured values, for group B: mean value of 2 measured values) are shown at the corresponding times. Group C was used as a reference as in the previous examples.

Group A and group B show a delay of the degradation rates compared to the uncoated stents (group C).

Conclusion

Bombarding magnesium alloy A (Mg10Dy1Nd1Zn0.2Zr) stents with fluorine and oxygen ions (ion implantation) can significantly reduce degradation rates compared to uncoated stents.

Example 13: Degradation Tests of Stents after Additional Heat Treatment and Subsequent Fluoridation In contrast to example 10, in this method stents of magnesium alloy A (Mg10Dy1Nd1Zn0.2Zr) were first annealed and then treated with hydrofluoric acid. The same design and substrate material (magnesium alloy A) was used for all stents. All stents of the following groups were laser cut, heat treated and electropolished.

Five stents of magnesium alloy A (Mg10Dy1Nd1Zn0.2Zr) were first annealed (in addition to the first annealing) in air for four hours at 400° C. in a tube furnace. The stents were then divided into two groups and treated differently.

Group A: Two of the previously additionally heat-treated stents were each placed in a plastic container. The plastic containers with lids (made of PP) were each filled with 50 ml 38-40% hydrofluoric acid and closed. The plastic containers were fixed in a shaking incubator and shaken at 50° C. and for 24 hours at 120 rpm. After treatment, the stents were removed from the hydrofluoric acid, rinsed with deionized water and swivelled into ethanol. The stents were then dried in a drying chamber at 80° C. for 30 minutes.

Group B: Three of the previously additionally heat-treated stents were treated identically to the group A stents, but a 48% hydrofluoric acid was used for fluoridation.

Group C: Untreated stents of magnesium alloy A (Mg10Dy1Nd1Zn0.2Zr) with the same design and material lot as group A and B.

Photometric Measurement

The degradation measurements were carried out as in example 9 and are shown in FIG. 12. For sample specification A, the mean values were measured for the two stents treated as described above. Sample B is a reference for mean values from the measurements of three uncoated stents of the same design and magnesium alloy A (Mg10Dy1Nd1Zn0.2Zr).

The mass of magnesium ions dissolved over time (FIG. 12) shows that the fluoridated stents of group A and B have a significantly lower rate of degradation than the uncoated stents of Group C. Particularly within the first 5 hours is shown that the stents of group A and B released only about one third of the mass of magnesium ions than the uncoated stents. In addition, the degradation time of group B was significantly extended than that of group C as a whole.

Conclusion

Additional annealing in air and subsequent fluoridation could significantly reduce the degradation rate of the stents during the first hours, which could be advantageous with regard to the in vivo ingrowth of the stent. The fluoridation of the stents in 48% hydrofluoric acid not only reduced the initial degradation rate, but also slowed down the overall degradation time.

Example 14: Degradation Tests of Stents Having an Intermediate Layer of Magnesium Fluoride and a Further Coating of Parylene C The same design and substrate material (magnesium alloy A) was used for all stents. All stents of the following groups were laser cut, heat treated and electropolished.

The purpose of this experiment was to demonstrate the influence of a magnesium fluoride interlayer below a 2.5 µm parylene C layer.

Two groups of coated stents were compared:

Group A: Stents of magnesium alloy A (Mg10Dy1Nd1Zn0.2Zr) were placed in a plastic container. The plastic containers with lids (made of PP) were each filled with 50 ml 38-40% hydrofluoric acid and then placed in a tempered water bath at a temperature of 50° C. The water was heated to 50° C. in a glass reservoir by a heating plate and kept at 50° C. during the treatment process. An agitator in the reservoir allows to easily move the plastic containers in the water bath. After 24 hours, the plastic containers were removed from the water bath. The stents in turn were removed from the hydrofluoric acid, rinsed with deionized water, dried with compressed air and packed in a glass tube. The layer thickness of the fluoride layer was 1-2 µm.

The stents were then coated with chlorinated poly-p-xylylene (parylene C). Parylene C can be deposited directly from the gas phase on the substrate, resulting in a very uniform coating. The thickness of the coating can be varied over the duration of the treatment.

Group B: The stents of group B were coated directly (i.e. without an intermediate layer of magnesium fluoride) with the polymer parylene C. The layer thickness of the polymer was the same because they were coated in the same coating cycle as the stents of group A.

Photometric Measurement

The degradation measurements were carried out as in example 9 and are shown in FIG. 13. The sample specification A is the mean of the dissolved mass values of magnesium of two stents of group A.

Sample B is the mean value of the dissolved mass of magnesium of two stents of group B.

The measurement of dissolved magnesium ions shows that the stents of group A (stents having an intermediate layer of magnesium fluoride) degrade much more slowly than stents of group B (without an intermediate layer of magnesium fluoride). The degradation rate is roughly halved.

Conclusion

The layer thickness, the layer application and the layer homogeneity of the polymer were identical for both groups as these were coated in parallel in the same coating cycle. This means that the slower degradation rate of stents of group A compared to group B can be attributed solely to the magnesium fluoride interlayer. The magnesium fluoride layer is therefore also suitable as an intermediate layer for other coatings (such as polymer coatings).

Example 15: Degradation Tests of Stents Having an Intermediate Layer of Magnesium Fluoride and a Further Coating of an Resorbable Polymer The same design and substrate material (magnesium alloy A) was used for all stents. All stents of the following groups were laser cut, heat treated and electropolished. The layer thicknesses of the applied polymer were the same for all groups.

Group A: Stents of magnesium alloy A (Mg10Dy1Nd1Zn0.2Zr) having a layer of poly-L-lactide (PLLA), which was applied to the stent by spraying method.

Group B: Stents of magnesium alloy A (Mg10Dy1Nd1Zn0.2Zr) having a layer of poly-ε-caprolactone (PCL), which was applied to the stent by spraying method.

Group C: Stents of magnesium alloy A (Mg10Dy1Nd1Zn0.2Zr) having a layer of poly-L-lactide (PLLA), which was applied to the stent by spraying method and an intermediate layer of magnesium fluoride. The magnesium fluoride layer was applied to the stents as in example 13 (group A).

Group D: Stents of magnesium alloy A (Mg10Dy1Nd1Zn0.2Zr) having a layer of poly-ε-caprolactone (PCL), which was applied to the stent by spraying method and an intermediate layer of magnesium fluoride. The magnesium fluoride layer was applied to the stents as in example 13 (group A).

Photometric Measurement

The degradation measurements were carried out as in example 9 and are shown in FIG. 14. The sample specification A is the dissolved mass of magnesium of a stent of group A.

Sample B is the dissolved magnesium mass of a stent of group B.

Sample C is the mean value of the dissolved mass of magnesium of two stents of group C.

Sample D is the mean value of the dissolved mass of magnesium of two stents of group D.

The measurement of dissolved magnesium ions (FIG. 14) shows that the stents having an intermediate layer of magnesium fluoride (groups C and D) degrade much more slowly than the stents without an intermediate layer. The combination of magnesium fluoride and poly-ε-caprolactone (group D) shows the slowest degradation rate followed by magnesium fluoride and poly(L-lactide) (group C).

Conclusion

In this experiment, it could be shown that the degradation time of stents of magnesium alloy A having a resorbable polymer coating can considerably be further slowed down by an intermediate layer of magnesium fluoride. The layer thickness of the respective polymer was identical for all stents (10 μm). The intermediate layer of magnesium fluoride decelerated the degradation time both for PLLA-coated stents (group A vs. group C) and for PCL-coated stents (group B vs. group D).

A layer of magnesium fluoride on a stent of magnesium alloy A (Mg10Dy1Nd1Zn0.2Zr) is therefore also suitable as an intermediate layer for a resorbable polymer coating to significantly decelerate the rate of degradation.

Example 16: Degradation Tests of Stents Having an Intermediate Layer of Magnesium Fluoride and an Additional Coating of Poly(L-Lactide) (PLLA) and Introduced Drug The same design and substrate material (magnesium alloy A) was used for all stents. All stents of the following groups were laser cut, heat treated and electropolished.

Group A: Stents of magnesium alloy A (Mg10Dy1Nd1Zn0.2Zr) with a 7 μm layer of poly-L-lactide (PLLA) with an introduced drug (rapamycin), which was applied by spraying method and an intermediate layer of magnesium fluoride. The magnesium fluoride layer was applied to the stents as in example 13 (group A).

Group B: Stents of magnesium alloy A (Mg10Dy1Nd1Zn0.2Zr) with a 7 μm layer of poly-L-lactide (PLLA) with an introduced drug (rapamycin) applied to the stent by spraying method.

Photometric Measurement

The degradation measurements were carried out as in example 9 and are shown in FIG. 16. The sample specification A is the mean of the measurements of dissolved mass of magnesium of two stents of group A.

Sample B is the mean value of the dissolved mass of magnesium of three stents of group B.

The photometric concentration measurement (FIG. 16) shows that the stents having an intermediate layer of magnesium fluoride degrade more slowly than the stents without such a layer at same layer thickness of the polymer coating (7 μm).

Conclusion

In this experiment it could be shown that the degradation time of stents of magnesium alloy A having a resorbable polymer coating of poly-L-lactide (PLLA) and a layer thickness of 7 μm can considerably be slowed down by an intermediate layer of magnesium fluoride.

Example 17: Degradation Tests of Stents Having an Intermediate Layer of Magnesium Fluoride and a Further Coating of Poly-ε-Caprolactone (PCL) with Introduced Drug and Different Layer Thicknesses The same design and substrate material (magnesium alloy A) was used for all stents. All stents of the following groups were laser cut, heat treated, and electropolished.

Group A: Stents of magnesium alloy A (Mg10Dy1Nd1Zn0.2Zr) with a 4 μm layer of poly-ε-caprolactone (PCL), which was applied to the stent by spraying method.

Group B: Stents of magnesium alloy A (Mg10Dy1Nd1Zn0.2Zr) with a 7 μm layer of poly-ε-caprolactone (PCL), which was applied to the stent by spraying method.

Group C: Stents of magnesium alloy A (Mg10Dy1Nd1Zn0.2Zr) with a 4 μm layer of poly-ε-caprolactone (PCL), which was applied to the stent by spraying method and an intermediate layer of magnesium fluoride. The magnesium fluoride layer was applied to the stents as in example 13 (group A).

Group D: Stents of magnesium alloy A (Mg10Dy1Nd1Zn0.2Zr) with a 7 μm layer of poly-ε-caprolactone (PCL), which was applied to the stent by spraying method and an intermediate layer of magnesium fluoride. The magnesium fluoride layer was applied to the stents as in example 13 (group A).

Photometric Measurement

The degradation measurements were carried out as in example 9 and are shown in FIG. 15. The sample specification A is the dissolved mass of magnesium of a stent of group A.

Sample B is the dissolved magnesium mass of a stent of group B.

Sample C is the mean value of the dissolved mass of magnesium of two stents of group C.

Sample D is the mean value of the dissolved mass of magnesium of two stents of group D.

The photometric concentration measurement (FIG. 15) shows that the stents having an intermediate layer of magnesium fluoride degrade more slowly than the stents without such a layer at the same layer thickness of the polymer coating (4 μm or 7 μm).

Example 18: Degradation Tests of Stents Having an Inorganic and a Further Coating of an Resorbable Polymer with Different Composition of the Inorganic Coating The same design and substrate material (magnesium alloy A) was used for all stents. All stents of the following groups were laser cut, heat treated and electropolished.

Group A: Stents of magnesium alloy A (Mg10Dy1Nd1Zn0.2Zr) having an inorganic coating (surface transformation) of magnesium hydroxide and a 5 μm layer of poly-L-lactide (PLLA), which was applied by spraying method. The magnesium hydroxide surface was applied to the stents in a wet chemical process. The polished stents were immersed for 2 min in 30% $H_2O_2$ solution at room temperature. Afterwards these were rinsed with $H_2O$ and immersed in ethanol and dried at 80° C. for one hour in a drying chamber.

Group B: Stents of magnesium alloy A (Mg10Dy1Nd1Zn0.2Zr) having an inorganic coating (surface transformation) of magnesium carbonate/magnesium hydroxide and a 5 µm layer of poly-L-lactide (PLLA), which was applied by spraying method. The surface transformation was realized by means of a wet chemical process. Thereby the polished stents were immersed in saturated $NaHCO_3$ solution for 5 min and at 37° C. The stents were then rinsed with $H_2O$ and immersed in ethanol. Afterwards the stents were dried at 100° C. for one hour in a drying chamber.

Group C: Stents of magnesium alloy A (Mg10Dy1Nd1Zn0.2Zr) having an inorganic coating (surface transformation) of magnesium phosphate/magnesium hydroxide and a 10 µm layer of poly-L-lactide (PLLA), which was applied by spraying method.

The surface transformation was realized by means of a wet chemical process. Thereby the polished stents were immersed in saturated $Na_2HPO_4$ solution for one hour at 37° C. Afterwards the stents were rinsed with $H_2O$ and immersed in ethanol. The stents were then dried at 100° C. for one hour in a drying chamber.

Group D: Stents of magnesium alloy A (Mg10Dy1Nd1Zn0.2Zr) having an inorganic coating (surface transformation) of magnesium fluoride and a 5 µm layer of poly-L-lactide (PLLA), which was applied by spraying method. The magnesium fluoride layer was applied to the stents as in example 13 (group A).

Group E: Stent of magnesium alloy A (Mg10Dy1Nd1Zn0.2Zr) having an inorganic coating (surface transformation) of magnesium fluoride. The magnesium fluoride layer was applied to the stents as in example 13 (group A).

Photometric Measurement

The degradation measurements were carried out as in example 9 and are shown in FIG. 17. The sample specification A is the measurement of the dissolved mass of magnesium relative to the initial surface of a stent of group A (A1 and A2).

Sample B is the dissolved mass of magnesium relative to the initial surface of a stent of group B (B1 and B2).

Sample C is the dissolved mass of magnesium relative to the initial surface of two stents of group C (C1 and C2).

Sample D is a measurement of the dissolved mass of magnesium relative to the initial surface of two stents of group D (D1 and D2).

Sample E is a measurement of the dissolved mass of magnesium relative to the initial surface of a stent of group E.

The photometric concentration measurement (FIG. 17) shows that the stents having an intermediate layer of magnesium fluoride degrade more slowly than stents with other intermediate layers.

Conclusion

In this experiment it could be shown that an inorganic coating of magnesium fluoride on the stent significantly decelerates the degradation time of stents of magnesium alloy A having an resorbable polymer coating compared to inorganic coatings consisting of magnesium hydroxide, magnesium carbonate and magnesium phosphate.

A coating of magnesium fluoride and an overlying coating of poly-L-lactide (PLLA) on a stent of magnesium alloy A (Mg10Dy1Nd1Zn0.2Zr) is particularly suitable to decelerate the degradation rate considerably.

Example 19: Coating of Stents with a Bioresorbabie Polymer and an Overlying Magnesium Fluoride Layer The stents (magnesium alloy A) were laser cut, heat treated, and electropolished. The polymer (PLLA) was then applied with embedded drug (rapamycin, 1.4 µg/mm²) in a spraying method. The subsequent application of a magnesium fluoride layer was carried out with IBAD (ion beam assisted deposition). The IBAD process comprises a thin layer formation with simultaneous ion bombardment of this layer from an ion source. In this case the coating was formed by evaporating magnesium fluoride from a molybdenum crucible at a pressure of e.g. 1 E-05 Pa. The application rate can be varied and is e.g. between 0.3 and 1.5 nm/s. The layer thickness can also be adjusted over time. In the present case, the layer thickness was about 800 nm. The temperature of the sample always remained below 70° C. so that the properties of the polymer and the drug were not influenced. The magnesium fluoride layer proved to be brittle. During crimping of the stents from the initial diameter of 1.8 mm to 1.1 mm, cracks and even detachments of the $MgF_2$ layer were already detected by using light microscopes. During subsequent dilatation to a diameter of 3.2 mm, it was found that the $MgF_2$ layer detached from the polymer in areas of greatest deformation of the stent. It can therefore be assumed that this layer does not lead to a degradation delay in this combination. In addition, spalling of the $MgF_2$ layer from the polymer can lead to a local and thus non-uniform release of the drug. Flaking parts could also lead to an embolism.

Example 20: Degradation Tests of Stents Having an Intermediate Layer of Magnesium Fluoride and a Further Coating of Parylene N The same design and substrate material (magnesium alloy A) was used for all stents. All stents of the following groups were laser cut, heat treated and electropolished.

The purpose of this experiment was to demonstrate the influence of a magnesium fluoride interlayer below a 0.1 µm parylene N layer.

Two groups of coated stents were compared:

Group A: Two stents of magnesium alloy A (Mg10Dy1Nd1Zn0.2Zr) were treated as in example 13 group B to obtain a magnesium fluoride layer.

The stents were then coated with the polymer parylene N (poly-p-xylylene). Parylene N can be deposited directly from the gas phase by condensation on the substrate, resulting in a very uniform coating. The layer thickness can be varied over the duration of the treatment.

Group B: The two stents of group B were coated directly (i.e. without an intermediate layer of magnesium fluoride) with the polymer parylene N. The layer thickness of the polymer was the same as these were coated in the same coating cycle as the stents of group A.

Group C: The two stents were treated as in group A, but no polymer was applied.

Group D: The three stents had no coating (no magnesium fluoride layer and no polymer layer).

Photometric Measurement

The degradation measurements were carried out as in example 9 and are shown in FIG. 18. The sample designation A is the mean of the dissolved mass values of magnesium of two stents of group A.

Sample B is the mean value of the dissolved mass of magnesium of two stents of group B. Sample C is the mean value of the dissolved mass of magnesium of two stents of group C. Sample D is the mean value of the dissolved mass of magnesium of three stents of group D.

The measurement of the dissolved magnesium ions shows that the stents of group A (stents having an intermediate layer of magnesium fluoride) degrade much more slowly than stents of group B (without an intermediate layer of magnesium fluoride). The degradation rate is reduced by a factor of 2.5. The stents of group A degrade at about the same rate as the stents of group C. The stents of group D degrade the fastest.

Conclusion

The layer thickness, the layer application and the layer homogeneity of the polymer were identical for both groups as these were coated in parallel in the same coating cycle. This means that the slower degradation rate of the stents of group A compared to group B can be attributed solely to the magnesium fluoride interlayer. The comparison with uncoated stents and stents having only a magnesium fluoride layer shows that only the combination of the intermediate layer (magnesium fluoride) and the polymer (in this case parylene N) allows such a reduction in degradation. The individual coatings applied alone do not show the corresponding degradation inhibition.

Example 21: Degradation Tests of Stents Having an Intermediate Layer of Magnesium Fluoride and a Further Coating of Polyethyleneimine (PEI) and Polyacrylic Acid (PAA)

The same design and substrate material (magnesium alloy A) was used for all stents. All stents of the following groups were laser cut, heat treated and electropolished.

The aim of this experiment was to demonstrate the influence of an intermediate layer of magnesium fluoride below a double layer of polyethyleneimine (PEI, Mw 25,000) and polyacrylic acid (PAA, My 450,000). Stents with and without an intermediate layer of magnesium fluoride were compared. The magnesium fluoride layer was applied as in example 20 (group A).

The double layer of PEI and PAA was applied by a layer by layer method. The stents (uncoated and coated with magnesium fluoride) were successively immersed in an aqueous solution of 5 mg/ml PAA for two minutes, then in deionized water for one minute, then in an aqueous solution of 5 mg/ml PEI for two minutes and finally in deionized water for one minute. This sequence was repeated five and ten times, respectively, and the stents were then dried in air.

Group A: A stent of magnesium alloy A (Mg10Dy1Nd1Zn0.2Zr) and a layer of PEI and PAA. The double layer of PEI and PAA was applied by layer by layer method. The stent was immersed successively in an aqueous solution of 5 mg/ml PAA for two minutes, then in deionized water for one minute, then in an aqueous solution of 5 mg/ml PEI for two minutes and finally in deionized water for one minute. This sequence was repeated five times and the stent was dried in air afterwards.

Group B: A stent of magnesium alloy A (Mg10Dy1Nd1Zn0.2Zr), which was treated as in example 13 group B to generate an intermediate layer of magnesium fluoride. This was followed by the same coating sequence as for Stent A (5×PEI and PAA).

Group C: Similarly coated stent as in group A but with 10 coating rounds for generation of the PEI and PAA layer.

Group D: Similarly coated stent as in group B but with 10 coating rounds for generation of the PEI and PAA layer.

Group E: Stents of magnesium alloy A (Mg10Dy1Nd1Zn0.2Zr) without any further coating.

Photometric Measurement

The degradation measurements were carried out as in example 9 and are shown in FIG. 19. The specification of the measured values corresponds to those of the stent specifications. The values of group E are mean values from the values of three stents.

The stents having a triple coating of magnesium fluoride and PEI and PAA degrade more slowly than those with only a PEI and PAA layer.

Conclusion

In this experiment it could be shown that an intermediate layer of magnesium fluoride also has an additional degradation-inhibiting effect, even if polyacrylic acid and polyethyleneimine are used as coatings, when compared with stents without an intermediate layer of magnesium fluoride.

Example 22: Degradation Tests of Stents of Different Alloys with and without an Intermediate Layer of Magnesium Fluoride and a Further Coating of Poly-L-Lactide For the experiment the same design was used for all stents. An stents of the following groups were laser cut, heat treated and electropolished. Some of the stents differed in the magnesium alloy used.

Group A: Stents of magnesium alloy A (Mg10Dy1Nd1Zn0.2Zr) with a 5 μm layer of poly-L-lactide (PLLA), which was applied by spraying method.

Group B: Stents of magnesium alloy A (Mg10Dy1Nd1Zn0.2Zr) having an inorganic coating (surface transformation) of magnesium fluoride and a 5 μm layer of poly-L-lactide (PLLA), which was applied by spraying method. The magnesium fluoride layer was applied to the stents as in example 13 (group B).

Group C: Stents of magnesium alloy L37 having a 5 μm layer of Poly-L-Lactide (PLLA), which was applied by spraying method.

Group D: Stents Magnesium alloy L37 having an inorganic coating (surface transformation) of magnesium fluoride and a 5 μm layer of poly-L-lactide (PLLA), which was applied by spraying method. The magnesium fluoride layer was applied to the stents as in example 13 (group B).

Group E: Stents of magnesium alloy AZ91 (Mg9Al1Zn) having a 5 μm layer of poly-L-lactide (PLLA), which was applied by spraying method.

Group F: Stents of magnesium alloy AZ91 (Mg9Al1Zn) having an inorganic coating (surface transformation) of magnesium fluoride and a 5 μm layer of poly-L-lactide (PLLA), which was applied by spraying method. The magnesium fluoride layer was applied to the stents as in example 13 (group B).

Photometric Measurement

The degradation measurements were carried out as in Example 9 and are shown in FIG. 20.

The sample specification A is the mean value of the dissolved mass of magnesium relative to the time of two samples from group A each.

The same applies to the other samples (B, C, D, E, F).

Here, for all alloys used, stents of this alloy corrode more slowly in case an intermediate layer of magnesium fluoride is applied (compare A and B, as well as C and D, and E and F). Stents of alloy L37 degraded faster than those of alloys A and AZ91 (Mg9Al1Zn).

Conclusion

In this experiment, it could be shown that an intermediate layer of magnesium fluoride in combination with an organic coating significantly decelerates the degradation even in case of different alloys as stent material. If no intermediate layer is applied, the degradation rate is significantly faster.

This experiment shows that an intermediate layer of magnesium fluoride can also be applied to magnesium alloys other than alloy A.

Example 23: Degradation Tests of Stents with and without an Intermediate Layer of Magnesium Fluoride and a Further Coating of Poly(Lactid-Co-Glycolide) (PLGA)

The same design and substrate material (magnesium alloy A) was used for all stents. All stents of the following groups were laser cut, heat treated and electropolished.

Group A: Stents of magnesium alloy A (Mg10Dy1Nd1Zn0.2Zr) having a layer of poly(lactid-co-glycolide) (PLGA), which was applied by dip coating. The stent was immersed in a solution of PLGA (85:15) and trichloromethane (5 mg/ml), pulled out of the solution at 20 mm/min and then dried in air at 40° C.

Group B: Stents of magnesium alloy A (Mg10Dy1Nd1Zn0.2Zr) having an inorganic coating (surface transformation) of magnesium fluoride and an overlying layer of poly(lactid-co-glycolide) (PLGA). The magnesium fluoride coating has been applied as in example 13 group B. The PLGA coating was applied in the same way as group A.

Group C: Stents of magnesium alloy A (Mg10Dy1Nd1Zn0.2Zr) without any coating.

Photometric Measurement

The degradation measurements were carried out as in Example 9 and are shown in FIG. 21.

The sample specification A is the mean value of the dissolved mass of magnesium relative to the time of two samples from group A each.

The same applies to the other samples (B,C).

The coated stents degrade more slowly than the uncoated ones, the ones with an intermediate layer of magnesium fluoride degrading most slowly.

Conclusion

In this experiment it could be shown that an intermediate layer of magnesium fluoride in combination with an organic coating (in this case PLGA) degrades much more slowly than stents without such or without any coating. The experiment shows that the combination of magnesium fluoride as intermediate layer and PLGA as overlying organic layer is particularly suitable to decelerate the degradation.

Example 24: Degradation Tests of Stents with and without an Intermediate Layer of Magnesium Fluoride and a Further Coating of Polymethacrylamide (PMAA)

The same design and substrate material (magnesium alloy A) was used for all stents. All stents of the following groups were laser cut, heat treated and electropolished.

Group A: Three stents of magnesium alloy A (Mg10Dy1Nd1Zn0.2Zr) having a layer of PMAA, which was applied by dip coating (A1, A2, A3).

Group B: Stents of magnesium alloy A (Mg10Dy1Nd1Zn0.2Zr) having an inorganic coating (surface transformation) of magnesium fluoride and an overlying layer of PMAA (B1, B2, B3).

Group C: Stents of magnesium alloy A (Mg10Dy1Nd1Zn0.2Zr) without any coating.

Photometric Measurement The degradation measurements were carried out as in Example 9 and are shown in FIG. 22.

The sample specification C is the mean value of the dissolved mass of magnesium relative to the time of three samples from group C.

The double-coated stents (magnesium fluoride and PMAA) degrade more slowly than the uncoated ones. The stents coated with PMAA only show no delay in degradation rate compared to uncoated stents.

Conclusion

In this experiment it could be shown that an intermediate layer of magnesium fluoride in combination with an organic coating (in this case PMAA) degrades more slowly than stents without such or without any coating. The experiment shows that the combination of magnesium fluoride as intermediate layer and PMAA as overlying organic layer is suitable to decelerate the degradation (at least in the first hours of the experiment). However, other polymers are more suitable as overlying layers.

Example 25: Degradation Tests of Stents with and without an Intermediate Layer of Magnesium Fluoride and a Further Coating of Poly-L-Lactide in Comparison to Stents of Alloy L37 Having a Coating of Poly-L-Lactide The same design and substrate material (magnesium alloy A) was used for all stents of groups B and C for the experiment. The material used for the stents of group A was L37 alloy. All stents were laser cut, heat treated and electropolished and then coated.

Group A: Two stents of L37 magnesium alloy having a PLLA coating and an abluminal layer thickness of 6-12 µm.

Group B: Two stents of magnesium alloy A (Mg10Dy1Nd1Zn0.2Zr) having a coating of 7.5 µm PLLA and an introduced drug (rapamycin, 1.4 µg/mm$^2$). The PLLA coating was applied by spraying method.

Group C: Stents of magnesium alloy A (Mg10Dy1Nd1Zn0.2Zr) having an inorganic coating (surface transformation) of magnesium fluoride and an overlying layer of 7.5 µm PLLA with introduced drug (rapamycin, 1.4 µg/mm$^2$). The magnesium fluoride coating was applied as in example 13, group B. The PLLA coating was applied by spraying method.

Photometric Measurement

The degradation measurements were carried out as in example 9 and are shown in FIG. 23. Since stents with different designs were compared, the mass of dissolved Mg ions was related to the initial surface of the respective stents.

The specifications A1 and A2 refer to the measured values of the two stents in group A. The same applies to groups B and C.

Both stents of group B and stents of group C degrade much more slowly than stents of group A. Stents having an intermediate layer of magnesium fluoride (group C) degrade the slowest.

Conclusion

In this experiment it was shown that stents of magnesium alloy A having an intermediate layer of magnesium fluoride in combination with an organic coating (in this case PLLA) with an introduced drug degrade more slowly than stents without such an intermediate layer. In addition, stents of magnesium alloy A degrade much more slowly than stents of alloy L37 having a comparable coating without an intermediate layer. The experiment shows that the combination of magnesium fluoride as the intermediate layer and PLLA as the overlying organic layer is suitable to significantly decelerate degradation. The measured values within group C scatter the least in this comparison, which indicates a very homogeneous layer (double layer).

The invention claimed is:

1. A stent of biodegradable magnesium alloy having two coatings, wherein the first coating is an inorganic coating comprising magnesium fluoride and the second coating is an organic coating, the magnesium alloy containing at least 80% by weight magnesium, and wherein the inorganic coating covers the stent and the organic coating covers the inorganic coating, wherein the organic coating comprises one or more substances of the following group: poly(ε-caprolactone), poly(L-lactide-co-glycolide), poly(L-lactide), and parylene, wherein the organic coating is metal-free and does not contain metal-containing compounds and/or organometallic compounds, metal alkoxides or polymeric metal alkoxides, wherein the layer thickness of the organic coating is 0.5 μm to 10 μm; or in case of parylene, wherein the layer thickness of the organic coating is 0.001 μm to 10 μm; and wherein the layer thickness of the inorganic coating is 0.1 pm to 10 μm;

wherein the biodegradable magnesium alloy comprises
        5.0% by wt.-13.0% by wt. dysprosium,
        0.01% by wt.-1.5% by wt. neodymium and/or europium,
        0.0% by wt.-2.0% by wt. zinc,
        0.0% by wt.-1.0% by wt. zirconium, and
        at least 80.0% by wt. magnesium.

2. The stent according to claim 1, wherein the organic coating has no micropores, holes, openings or channels.

3. The stent according to claim 1, wherein at least one anti-inflammatory, antiproliferative, antiangiogenic, antirestenotic, antineoplastic, antimigrative and/or antithrombogenic active agent is present in or on the organic coating.

4. The stent according to claim 3, wherein the at least one anti-inflammatory, antiproliferative, antiangiogenic, antirestenotic, antineoplastic, antimigrative and/or antithrombogenic active agent is selected from the group consisting of paclitaxel, sirolimus, biolimus A9, myolimus, novolimus, pimecrolimus, tacrolimus, temsirolimus, zotarolimus, everolimus and ridaforolimus.

5. The stent according to claim 1, wherein the stent is a stent for blood vessels, urinary tracts, respiratory tracts, biliary tracts or digestive tract.

6. The stent according to claim 1, wherein the stent is a stent for blood vessels, urinary tracts, respiratory tracts, biliary tracts or digestive tract.

7. A stent of biodegradable magnesium alloy, comprising:
an inorganic coating comprising magnesium fluoride; and
an organic coating,
the magnesium alloy containing at least 80% by weight magnesium,
wherein the inorganic coating covers the stent and the organic coating covers the inorganic coating,
wherein the organic coating comprises an organic polymer selected from the group consisting of:
polyvinyl pyrrolidone, poly hydroxyethyl methacrylates, polyethylene glycol, polypropylene glycol, polyvinyl alcohol, polyvalerolactones, poly-ε-decalactones, poly-lactonic acid, poly(glycolic acid), polylactides, poly(L-lactide), poly(D,L-lactide), and copolymers, poly(L-lactide-co-glycolide), poly(D,L-lactide-co-glycolide), poly(L-lactide-co-D,L-lactide), poly(L-lactide-co-trimethylene carbonate)] (PTMC), poly(ε-caprolactone), polyhydroxybutyric acid, polyhydroxyvalerates, polyhydroxybutyrate-co-valerates, poly(1,3-dioxane-2-one), poly(para-dioxanones), poly(maleic anhydrides), polyhydroxy methacrylates, fibrin, polycyanoacrylates, polycaprolactone dimethylacrylates, polycaprolactone butyl acrylates, polycaprolactone glycolides, poly(methyl methacrylate), poly(butyl methacrylate), polyacrylamide, polyamides, polyetheramides, polyethylene amine, polyimides, polycarbonates, polycarbourethanes, polyvinyl ketones, polyvinyl ethers, polyisobutylenes, polyvinyl aromatic compounds, polyvinyl esters, polyoxymethylenes, polytetramethylene oxide, polyethylene, polypropylene, polytetrafluoroethylene, polyurethanes, polyetherurethanes, polyolefin elastomers, parylene (poly-para-xylylene), parylene N, and parylene C, wherein the layer thickness of the organic coating is 0.001 μm to 10 μm in a case of the organic polymer being poly-para-xylylene (parylene), parylene N or parylene C, wherein the layer thickness of the organic coating is 0.5 μm to 10 μm in a case of the organic polymer being any other organic polymer; and wherein the biodegradable magnesium alloy comprises
91.0% by wt. to 92.0% by wt. of magnesium,
0.7% by wt. to 0.8% by wt. of dysprosium,
0.6% by wt. to 0.8% by wt. of gadolinium,
1.9% by wt. to 2.1% by wt. of neodymium,
0.6% by wt. to 0.8% by wt. of zirconium, and
3.9% by wt. to 4.2% by wt. of yttrium.

8. The stent according to claim 7, wherein the organic coating comprises one or more substances of the following group: poly(ε-caprolactone), poly(L-lactide-co-glycolide), poly(L-lactide) and parylene.

9. The stent according to claim 8, wherein the organic coating has no micropores, holes, openings or channels.

10. The stent according to claim 8, wherein at least one anti-inflammatory, antiproliferative, antiangiogenic, antirestenotic, antineoplastic, antimigrative and/or antithrombogenic active agent is present in or on the organic coating.

11. The stent according to claim 9, wherein the at least one anti-inflammatory, antiproliferative, antiangiogenic, antirestenotic, antineoplastic, antimigrative and/or antithrombogenic active agent is selected from the group consisting of paclitaxel, sirolimus, biolimus A9, myolimus, novolimus, pimecrolimus, tacrolimus, temsirolimus, zotarolimus, everolimus and ridaforolimus.

* * * * *